United States Patent
Yao et al.

(10) Patent No.: US 11,439,665 B2
(45) Date of Patent: *Sep. 13, 2022

(54) COMBINED CHIMERIC ANTIGEN RECEPTOR TARGETING CD19 AND CD20 AND APPLICATION THEREOF

(71) Applicant: CELLULAR BIOMEDICINE GROUP HK LIMITED, Hong Kong (CN)

(72) Inventors: Yihong Yao, Hong Kong (CN); Yanfeng Li, Hong Kong (CN); Yutian Wei, Hong Kong (CN); Shigui Zhu, Hong Kong (CN); Xin Yao, Hong Kong (CN); Jiaqi Huang, Hong Kong (CN)

(73) Assignee: CELLULAR BIOMEDICINE GROUP HK LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/475,766

(22) Filed: Sep. 15, 2021

(65) Prior Publication Data

US 2022/0031752 A1 Feb. 3, 2022

Related U.S. Application Data

(63) Continuation of application No. 16/877,069, filed on May 18, 2020, now Pat. No. 11,207,349.

(30) Foreign Application Priority Data

Mar. 17, 2020 (CN) .......................... 202010188038.1

(51) Int. Cl.
*A61K 35/17* (2015.01)
*C07K 14/705* (2006.01)
*A61P 35/00* (2006.01)

(52) U.S. Cl.
CPC .............. *A61K 35/17* (2013.01); *A61P 35/00* (2018.01); *C07K 14/70596* (2013.01)

(58) Field of Classification Search
None
See application file for complete search history.

(56) References Cited

U.S. PATENT DOCUMENTS 11,207,349 B2 * 12/2021 Yao ........................ A61K 35/17

FOREIGN PATENT DOCUMENTS

| CN | 109423495 A | 3/2019 |
| CN | 110606893 A | 12/2019 |
| CN | 112390891 A | 2/2021 |
| CN | 112608387 A | 4/2021 |

OTHER PUBLICATIONS

Makita et al. "Clinical development of anti-CD19 chimeric antigen receptor T-cell therapy for B-cell non-Hodgkin lymphoma'" Cancer Sci (2017) 108: 1109-1118.*
Martyniszyn et al. "CD20-CD19 Bispecific CAR T Cells for the Treatment of B-Cell Malignancies" Human Gene Therapy (2017) vol. 28, No. 12, pp. 1147-1157.*
Wang et al. "Effective response and delayed toxicities of refractory advanced diffuse large B-cell lymphoma treated by CD20-directed chimeric antigen receptor-modified T cells" Clinical Immunology (2014) 155, 160-175.*
Watanabe et al. "Target Antigen Density Governs the Efficacy of Anti-CD20-CD28-CD3z Chimeric Antigen Receptor—Modified Effector CD8+ T Cells" J Immunol 2015; 194: 911-920.*
Zah et al. "T cells expressing CD19/CD20 bi-specific chimeric antigen receptors prevent antigen escape by malignant B cells" Cancer Immunology Research (2016) vol. 4, No. 6, pp. 498-508.*
Zah et al. "Addendum: T cells expressing CD19/CD20 bi-specific chimeric antigen receptors prevent antigen escape by malignant B cells" Cancer Immunology Research (2016) vol. 4, No. 7, pp. 639-641.*
Zhou et al. "The efficacy and safety of anti-CD19/CD20 chimeric antigen receptor T cells immunotherapy in relapsed or refractory B-cell malignancies: a meta-analysis" BMC Cancer (2018) 18:929 (13 pages).*
Buehler et al, "Influence of Structural Variations on Biological Activity of Anti-PSMA scFv and Immunotoxins Targeting Prostate Cancer", AntiCancer Research, 30: 3373-3380 (2010).
Kim et al, "Improving the Productivity of Single-Chain Fv Antibody Against c-Met by Rearranging the Order of its Variable Domains", J. Microbiol. Biotechnol. (2008), 18(6), 1186-1190.
Kipriyanov et al, "Effect of Domain Order on the Activity of Bacterially Produced Bispecific Single-chain Fv Antibodies": J. Mol. Biol. (2003) 330, 99-111.

* cited by examiner

*Primary Examiner* — Ilia I Ouspenski
(74) *Attorney, Agent, or Firm* — Leason Ellis LLP

(57) ABSTRACT

The present invention provides a combined chimeric antigen receptor targeting CD19 and CD20 and application thereof. Specifically, the present invention provides a combined chimeric antigen receptor targeting CD19 and CD20, which comprises a scFv targeting CD19 and CD20, a hinge region, a transmembrane region, and an intracellular signaling domain. The present invention provides a nucleic acid molecule encoding the chimeric antigen receptor and a corresponding expression vector, a CAR-T cell, and applications thereof. The experimental results show that the chimeric antigen receptor provided by the present invention shows extremely high killing ability against tumor cells. The chimeric antigen receptor of the present invention targets CD19 and/or CD20 positive cells and can be used to treat CD19 and/or CD20 positive B-cell lymphoma, leukemia and other diseases.

4 Claims, 19 Drawing Sheets

Specification includes a Sequence Listing.

COMBINED CHIMERIC ANTIGEN RECEPTOR TARGETING CD19 AND CD20 AND APPLICATION THEREOF

TECHNICAL FIELD

The present invention relates to the field of bio-medicine, and more particularly to a combined chimeric antigen receptor targeting CD19 and CD20 and application thereof.

BACKGROUND

Malignant tumors of the blood system account for about 10% of human malignant tumors, and 95% of malignant tumors of the blood system are derived from B lymphocytes. Traditional chemotherapy and radiotherapy play an important role in the treatment of malignant tumors of the blood system. Some patients have significant effects, but it is difficult for most of the patients to be cured. New and effective treatments have been a hot topic in this field.

Adoptive T cell therapy has shown its powerful efficacy and bright prospect in the clinical treatment of malignant tumors. At present, it is regarded as one of the most promising methods for treating hematological tumors. CD19 is highly expressed on the surface of most B-cell malignancies. Multiple centers independently using Chimeric Antigen Receptor (CAR)-modified T cells to target recurrent, refractory malignant tumors of CD19-expressed B cell have achieved unprecedented success. At present, both of the two CAR-T products approved by FDA are targeting CD19 antigen and their indications are also expanding, such as chronic lymphocytic leukemia. Although the efficacy of anti-CD19 CAR-T is outstanding, many studies have shown that there are also many problems with CD19 chimeric antigen receptor (CAR) T cell therapy. There are still some patients with poor treatment results and easy to relapse. The reasons for this include the susceptibility of tumor cells to antigen escape. For example, a recent experiment of CD19 CAR-cell therapy showed that 90% of patients achieved complete remission, but 11% of these patients eventually relapsed, and the relapsing patients were mainly patients with CD19-negative tumor. In particular, in a clinical trial carried out at the University of Pennsylvania School of Medicine using CART19 in the treatment of recurrent, refractory acute B-cell lymphoma (R/R B-ALL), up to 94% of patients achieved complete remission. Although the initial response rate of this clinical trial was high, nearly 40% of patients relapsed after 1 month of treatment which achieved complete remission, and more than 60% of relapsing patients had CD19-negative tumor cells escape. Antigen escape has been found in adoptive transfer specific T cell receptors expressing NY-ESO1 and cancer vaccines treating melanoma. Spontaneous mutation and selective expansion are the main reasons for antigen escape.

Therefore, there is an urgent need in the art to develop methods for effectively treating tumors and preventing antigen escape.

SUMMARY OF THE INVENTION

An object of the present invention is to provide a method for effectively treating tumors and preventing antigen escape.

An object of the present invention is to provide a combined chimeric antigen receptor targeting CD19 and CD20 and preparation method thereof.

Specifically, it is an object of the present invention to provide a sequence of the combined chimeric antigen receptor targeting CD19 and CD20 as well as a preparation method and activity identification of the modified T cell (CART-19/20) thereof. The present invention provides a chimeric antigen receptor structure for use in the treatment of CD19 and CD20 positive B cell lymphoma.

In a first aspect of the invention, it provides a chimeric antigen receptor (CAR), wherein the structure of the chimeric antigen receptor is shown in formula I as below:

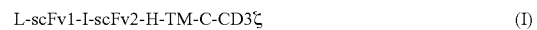

wherein, each "-" is independently a linker peptide or a peptide bond;

L is an optional signal peptide sequence;

I is a flexible linker;

H is an optional hinge region;

TM is a transmembrane domain;

C is a co-stimulatory signaling molecule;

CD3ζ is a cytoplasmic signaling sequence derived from CD3ζ;

one of scFv1 and scFv2 is an antigen binding domain targeting CD19, and the other is an antigen binding domain targeting CD20.

In another preferred embodiment, the scFv1 is an antigen binding domain targeting CD20, and the scFv2 is an antigen binding domain targeting CD19.

In another preferred embodiment, the structure of the antigen binding domain targeting CD20 is shown in formula A or B as below:

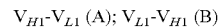

wherein $V_{H1}$ is an anti-CD20 antibody heavy chain variable region; $V_{L1}$ is an anti-CD20 antibody light chain variable region; and "-" is a linker peptide or a peptide bond.

In another preferred embodiment, the structure of the antigen binding domain targeting CD20 is shown in formula B.

In another preferred embodiment, the amino acid sequence of the $V_{H1}$ is shown in SEQ ID NO 1, and the amino acid sequence of the $V_{L1}$ is shown in SEQ ID NO 2; or the amino acid sequence of the $V_{H1}$ is shown in SEQ ID NO 3, and the amino acid sequence of the $V_{L1}$ is shown in SEQ ID NO 4.

In another preferred embodiment, the $V_{H1}$ and $V_{L1}$ are linked with a flexible linker (or a linker peptide), and the flexible linker (or the linker peptide) is 1-4, preferably 2-4, more preferably 3-4 consecutive sequences as shown in SEQ ID NO 7 (GGGGS).

In another preferred embodiment, the structure of the antigen binding domain targeting CD19 is shown in formula C or D as below:

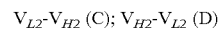

wherein $V_{L2}$ is an anti-CD19 antibody light chain variable region; $V_{H2}$ is an anti-CD19 antibody heavy chain variable region; and "-" is a linker peptide or a peptide bond.

In another preferred embodiment, the structure of the antigen binding domain targeting CD19 is shown in formula D.

In another preferred embodiment, the amino acid sequence of the $V_{L2}$ is shown in SEQ ID NO 5, and the amino acid sequence of the $V_{H2}$ is shown in SEQ ID NO 6.

In another preferred embodiment, the $V_{H2}$ and $V_{L2}$ are linked with a flexible linker (or a linker peptide), and the flexible linker (or the linker peptide) is 1-4, preferably 2-4, more preferably 3-4 consecutive sequence as shown in SEQ ID NO 7 (GGGGS).

In another preferred embodiment, the scFv1 and/or scFv2 are mouse-derived, humanized, humanized and mouse-derived chimeric, or fully humanized single chain antibody variable region fragments.

In another preferred embodiment, the structure of the chimeric antigen receptor is shown in formula II as below:

$$L\text{-}V_{L1}\text{-}V_{H1}\text{-}I\text{-}V_{H2}\text{-}V_{L2}\text{-}H\text{-}TM\text{-}C\text{-}CD3\zeta \quad (II)$$

wherein each element is as described above.

In another preferred embodiment, the sequence of the flexible linker I comprises 2-6, preferably 3-4 consecutive sequences as shown in SEQ ID NO 7 (GGGGS).

In another preferred embodiment, the L is a signal peptide of a protein selected from the group consisting of CD8, CD28, GM-CSF, CD4, CD137, and a combination thereof.

In another preferred embodiment, the L is a signal peptide derived from CD8.

In another preferred embodiment, the amino acid sequence of the L is shown in SEQ ID NO 8.

In another preferred embodiment, the H is a hinge region of a protein selected from the group consisting of CD8, CD28, CD137, Ig4, and a combination thereof.

In another preferred embodiment, the H is a hinge region derived from Ig4.

In another preferred embodiment, the amino acid sequence of the H is shown in SEQ ID NO 9.

In another preferred embodiment, the TM is a transmembrane region of a protein selected from the group consisting of CD28, CD3ε, CD45, CD4, CD5, CD8, CD9, CD16, CD22, CD33, CD37, CD64, CD80, CD86, CD134, CD137, CD154, and a combination thereof.

In another preferred embodiment, the TM is a transmembrane region derived from CD8 or CD28.

In another preferred embodiment, the sequence of the TM is shown in SEQ ID NO 10 or 11.

In another preferred embodiment, the C is a co-stimulatory signaling molecule of a protein selected from the group consisting of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, and a combination thereof.

In another preferred embodiment, the C is a co-stimulatory signaling molecule derived from 4-1BB or CD28.

In another preferred embodiment, the amino acid sequence of the C is shown in SEQ ID NO 12 or 13.

In another preferred embodiment, the amino acid sequence of the CD3ζ is shown in SEQ ID NO 14.

In another preferred embodiment, the amino acid sequence of the CAR is shown in SEQ ID NO 15 or 16.

In a second aspect of the invention, it provides a nucleic acid molecule, encoding the chimeric antigen receptor of the first aspect of the invention.

In another preferred embodiment, the nucleic acid molecule is isolated.

In another preferred embodiment, the nucleotide sequence of the nucleic acid molecule is shown in SEQ ID NO 17 or 18.

In a third aspect of the invention, it provides a vector, comprising the nucleic acid molecule of the second aspect of the invention.

In another preferred embodiment, the vector comprises DNA and RNA.

In another preferred embodiment, the vector is selected from the group consisting of plasmid, virus vector, transposon, and a combination thereof.

In another preferred embodiment, the vector comprises a DNA virus and a retrovirus vector.

In another preferred embodiment, the vector is selected from the group consisting of a lentiviral vector, an adenovirus vector, an adeno-associated virus vector, and a combination thereof.

In another preferred embodiment, the vector is a lentiviral vector.

In a fourth aspect of the invention, it provides a host cell, comprising the vector of the third aspect of the invention or having the exogenous nucleic acid molecule of the second aspect of the invention integrated into its genome or expressing the chimeric antigen receptor of the first aspect of the invention.

In another preferred embodiment, the cell is an isolated cell.

In another preferred embodiment, the cell is a genetically engineered cell.

In another preferred embodiment, the cell is a mammalian cell.

In another preferred embodiment, the cell is a CAR-T cell and/or a CAR-NK cell.

In another preferred embodiment, the cell targets both CD19 and CD20.

In a fifth aspect of the invention, it provides a method for preparing a CAR-T cell expressing the chimeric antigen receptor of the first aspect of the invention, wherein the method comprises the steps of: transducing the nucleic acid molecule of the second aspect of the invention or the vector of the third aspect of the invention into a T cell, thereby obtaining the CAR-T cell.

In another preferred embodiment, the method further comprises the step of detecting the function and effectiveness of the obtained CAR-T cell.

In a sixth aspect of the invention, it provides a preparation, comprising the chimeric antigen receptor of the first aspect of the invention, the nucleic acid molecule of the second aspect of the invention, the vector of the third aspect of the invention, or the host cell of the fourth aspect of the invention, and a pharmaceutically acceptable carrier, diluent or excipient.

In another preferred embodiment, the preparation is a liquid preparation.

In another preferred embodiment, the formulation of the preparation is an injection.

In another preferred embodiment, the preparation comprises the host cell of the fourth aspect of the invention, and the concentration of the host cell is $1 \times 10^3$-$1 \times 10^8$ cells/ml, preferably $1 \times 10^4$-$1 \times 10^7$ cells/ml.

In a seventh aspect of the invention, it provides the use of the chimeric antigen receptor of the first aspect of the invention, the nucleic acid molecule of the second aspect of the invention, the vector of the third aspect of the invention, or the host cell of the fourth aspect of the invention, for the preparation of a medicine or a formulation for preventing and/or treating tumor or cancer.

In another preferred embodiment, the tumor is selected from the group consisting of a hematological tumor, a solid tumor, and a combination thereof; preferably, the tumor is a hematological tumor.

In another preferred embodiment, the blood tumor is selected from the group consisting of acute myeloid leukemia (AML), multiple myeloma (MM), chronic lymphocytic leukemia (CLL), acute lymphoblastic leukemia (ALL), diffuse large B cell lymphoma (DLBCL), and a combination thereof.

In another preferred embodiment, the solid tumor is selected from the group consisting of gastric cancer, peritoneal metastasis of gastric cancer, liver cancer, leukemia, renal cancer, lung cancer, small intestine cancer, bone cancer, prostate cancer, colorectal cancer, breast cancer, large intestine cancer, cervical cancer, ovarian cancer, lymphoma, nasopharyngeal carcinoma, adrenal tumor, bladder tumor, non-small cell lung cancer (NSCLC), glioma, endometrial cancer, and a combination thereof.

In an eighth aspect of the invention, it provides a kit for the preparation of the cell of the fourth aspect of the invention, wherein the kit comprises a container, and the nucleic acid molecule of the second aspect of the invention or the vector of the third aspect of the invention located in the container.

In a ninth aspect of the invention, it provides a use of the cell of the fourth aspect of the invention, or the formulation of the sixth aspect of the invention for the prevention and/or treatment of cancer or tumor.

In a tenth aspect of the invention, it provides a method of treating a disease comprising administering an appropriate amount of the cell of the forth aspect of the invention, or the formulation of the sixth aspect of the invention, to a subject in need of treatment.

In another preferred embodiment, the disease is cancer or tumor.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

DESCRIPTION OF DRAWINGS

FIG. 6A shows the detection of the transfection efficiency of CAR-T19/20s cells. Protein L method was used to identify the expression level of CAR gene-encoded protein on the surface of T cell membrane in CAR-T19/20s cells cultured 9 days. $1 \times 10^5$ CAR-T19/20s cells cultured 10 days (FIG. 6B) and 18 days (FIG. 6C) were taken and cultured respectively with CD19-positive K562-CD19+ tumor cell line, CD20-positive K562-CD20+ tumor cell line, CD19 and CD20 double positive K562-CD19+CD20+ tumor cell line, RAJI or RAMOS tumor cell line that naturally expresses CD19 and CD20, and CD19 and CD20 double negative K562 or MOLT4 tumor cell line, or without tumor cells, in 200 l of GT-551 medium for 18 h with a ratio of 1:1. Then the expression level of CD137 on the surface of T cell membrane was detected respectively. FIG. 6D shows the secretion level of IFNγ in the culture supernatant. FIG. 6E shows the average body weight changes and average fluorescence intensity changes of mice injected with CAR-T19/20s cells within 21 days, which are recorded every 7 days. FIG. 6F shows in vivo imaging of mice injected with CAR-T19/20s cells on day 0 (DO), 7 (D7), 14 (D14), and 21 (D21) after injection.

FIG. 7A shows the testing results of the transfection efficiency of T cells. The expression level of CAR gene-encoded protein on the surface of T cell membrane in CAR-T20s cells cultured 7 days was identified by the DNA copy number detection method. FIG. 7B shows the secretion level of IFNγ in the supernatant of CAR-T20s cells co-cultured with target cells. FIG. 7C shows the expression level of CD137 on the surface of T cell membranes after co-culture.

FIG. 8A shows the testing results of the transfection efficiency of T cells. The expression level of the CAR gene-encoded protein on the surface of the T cell membrane in CAR-T20s cells cultured 7 days was identified by the Protein L method. FIG. 8B shows the secretion level of IFNγ in the supernatant of CAR-T20s cells co-cultured with target cells. FIG. 8C shows the expression level of CD137 on the surface of T cell membranes after co-culture.

FIG. 9A shows the testing results of the transfection efficiency of T cells. The expression level of the CAR gene-encoded protein on the surface of the T cell membrane in CAR-T20s cells cultured 7 days was identified by the Protein L method. FIG. 9B shows the secretion level of IFNγ in the supernatant of CAR-T20s cells co-cultured with target cells. FIG. 9C shows the expression level of CD137 on the surface of T cell membranes after co-culture.

FIG. 10A shows the detection results of T cell transfection efficiency. FIG. 10B shows the IFNγ secretion level in the supernatant after co-culture. FIG. 10C shows the detection of tumor cell killing ability of CAR-T20s cells, mainly by detecting the secretion level of LDH in the supernatant after co-culture. FIG. 10D shows the expression level of CD137 on the surface of T cell membranes.

Figure 1:
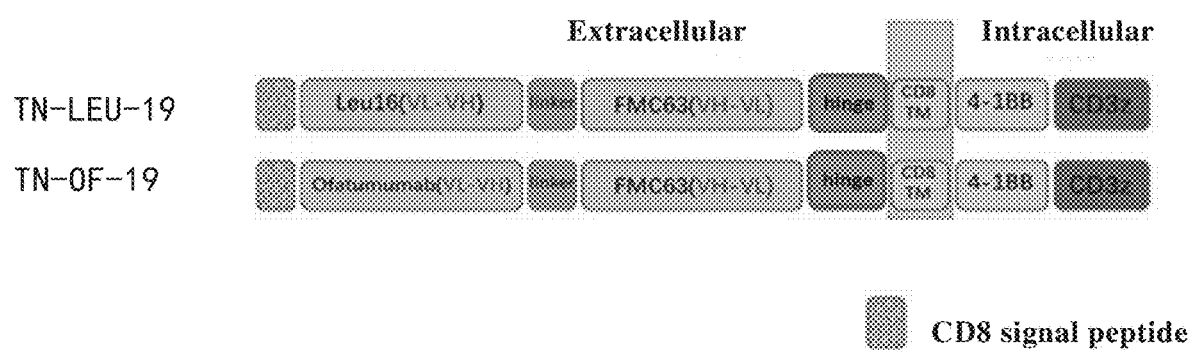
FIG. 1 shows structure of the combined chimeric antigen receptor targeting CD19 and CD20. The structure of the CAR comprises a leader sequence, an antigen recognition sequence, a hinge region, a transmembrane region, a costimulatory factor signal region, and a CD3ζ signaling region.

In the figures, TN-OF-19 and TN-20OF-19 have the same meaning, and TN-LEU-19 and TN-20 LEU-19 have the same meaning, both indicating CART cells having the corresponding CAR structure.

MODES FOR CARRYING OUT THE PRESENT INVENTION

After extensive and intensive studies, the inventors unexpectedly obtained a CAR-T cell that simultaneously targets CD19 and CD20. Specifically, the present invention provides a chimeric antigen receptor that simultaneously targets CD19 and CD20, which comprises a signal peptide, an anti-CD20 scFv, an anti-CD19 scFv, a hinge region, a transmembrane region, and an intracellular T cell signaling region. Moreover, the anti-CD20 scFv and anti-CD19 scFv were obtained through a large number of screenings, which were linked with peptide fragment with multiple repeat structure (G4S). The CAR-T cells of the present invention can recognize both CD19 and CD20 antigens at the same time, reducing the risk of immune escape caused by downregulation or deletion of antigen expression during the treatment of single-target CAR-T cells. Compared to CAR-T cells targeting single antigens and other double target CAR-T cells (targeting CD19 and CD20), the CAR-T cells of the present invention that simultaneously recognize two targets have stronger killing ability against tumor cells, less cytotoxicity, lower side effects, wider treatment range, lower recurrence rate and better efficacy. The present invention has been completed on the basis of this.

Terms

To make the disclosure easier to understand, some terms are firstly defined. As used in this application, unless expressly stated otherwise herein, each of the following terms shall have the meanings given below. Other definitions are set forth throughout the application.

The term "about" may refer to a value or composition within an acceptable error range for a particular value or composition as determined by those skilled in the art, which will depend in part on how the value or composition is measured or determined.

The term "administering" refers to the physical introduction of a product of the invention into a subject using any one of various methods and delivery systems known to those skilled in the art, including intravenous, intramuscular, subcutaneous, intraperitoneal, spinal or other parenteral administration, such as by injection or infusion.

The term "antibody" (Ab) may comprise, but is not limited to, an immunoglobulin that specifically binds an antigen and contains at least two heavy (H) chains and two light (L) chains linked by disulfide bonds, or an antigen binding parts thereof. Each H chain contains a heavy chain variable region (abbreviated herein as VH) and a heavy chain constant region. The heavy chain constant region contains three constant domains, CH1, CH2, and CH3. Each light chain contains a light chain variable region (abbreviated herein as VL) and a light chain constant region. The light chain constant region contains a constant domain CL. The VH and VL regions can be further subdivided into hypervariable regions called complementarity determining regions (CDR), which are interspersed within more conservative regions called framework regions (FR). Each VH and VL contains three CDRs and four FRs, which are arranged from amino terminal to carboxy terminal in the following order: FR1, CDR1, FR2, CDR2, FR3, CDR3, and FR4. The variable regions of the heavy and light chains contain a binding domain that interacts with an antigen.

CD20

Although the efficacy of anti-CD19 CAR-T is outstanding, many studies have shown that there are still many problems with CD19 chimeric antigen receptor (CAR) T cell therapy. There are still some patients with poor treatment results and easy to relapse. This includes the susceptibility of tumor cells to antigen escape.

In order to prevent the escape of CD19 CAR-T antigen, the inventors designs a combined bispecific CAR (ie, BICAR) that targets both CD19 and CD20, so that when CD19 antigen escapes and is not expressed in tumor cells, CD20 can be recognized to clear tumor cells in vivo.

CD20 is expressed in most patients with B-cell acute lymphoblastic leukemia, including some CD19 negative patients after anti-CD19 CAR-T treatment. CD20 is a glycosylated protein, and is the first identified B cell membrane marker. CD20 is also known as B 1, and encoded by the MS4A gene. CD20 molecule has four transmembrane hydrophobic regions, and its N-terminal and C-terminal are located on the cytoplasmic side, forming two closed loops outside the cell, and respectively called big loop and small loop. CD20 is specifically expressed in more than 95% of normal and cancerous B cells. These cells are in the pre-B cell stage and subsequent developmental stages, and CD20 stops expression until the cells differentiated into plasma cells. The present invention uses CD20 as another target for immunotherapy of B cell malignancies.

Bispecific Chimeric Antigen Receptor Targeting CD19 and CD20

Cellular immunotherapy is an emerging and highly effective tumor treatment model, and is a new type of autoimmunolgy treatment for cancer. It is a method for in vitro culture and amplification of immune cells collected from a patient using biotechnology and biological agents, and then the cells are transfused back to the patient to stimulate and enhance the body's autoimmune function, thereby achieving the purpose of treating tumors. The skilled in the art have been working to develop new cellular immunotherapy to increase the efficiency and reduce the side effect.

The present invention proposes a rational and optimized single-chain design and system, that is, combined bispecific CAR, which can be effectively integrated into primary human T cells, and can simultaneously target CD19 and CD20 when the T cells are activated. The CAR-T cells of the invention are capable of recognizing two antigens (CD19 and CD20). The invention provides a very effective potential method for preventing antigen escape.

The present invention uses CAR that simultaneously targets CD19 and CD20. Compared with CARs that target a single antigen, the affinity is enhanced, the activity of T cells is increased, and the targets have an additive or synergistic effect. In addition, due to uneven expression levels of CD19 and CD20 in tumor cells, double target CAR-T therapy has a wider scope. The CAR-T that simultaneously targets CD19 and CD20 on the surface of tumor cells can reduce the possibility of antigen escape caused by down-regulation or deletion of single surface antigen.

Bispecificity means that the same CAR can specifically bind and immunorecognize two different antigens, and the CAR can generate an immune response by binding to any one of the antigens.

The CD19 and CD20 bispecific CAR of the present invention has a single structure and comprises anti-CD19 and anti-CD20 scFvs. Wherein, the CAR comprises a CD19 scFv and a CD20 scFv, and the amino acid sequences, sequencing and hinge of CD19 scFv and CD20 scFv are the main factors affecting its function.

Specifically, the chimeric antigen receptor (CAR) of the invention comprises an extracellular domain, a transmembrane domain, and an intracellular domain. The extracellular domain comprises a target-specific binding element (also known as an antigen binding domain). The intracellular domain comprises a co-stimulatory signaling region and a ζ chain. The co-stimulatory signaling region refers to a part of the intracellular domain that comprises a co-stimulatory molecule. The co-stimulatory molecule is a cell surface molecule required for efficient response of lymphocytes to antigens, rather than an antigen receptor or ligand thereof.

A linker can be incorporated between the extracellular domain and the transmembrane domain of the CAR, or between the cytoplasmic domain and the transmembrane domain of the CAR. As used herein, the term "linker" generally refers to any oligopeptide or polypeptide that plays a role of linking the transmembrane domain to the extracellular domain or the cytoplasmic domain in a polypeptide chain. The linker may comprise 0-300 amino acids, preferably 2-100 amino acids and most preferably 3-50 amino acids.

In a preferred embodiment of the invention, the extracellular domain of the CAR provided in the present invention comprises an antigen binding domain targeting CD19 and CD20. When the CAR of the present invention is expressed in T cell, antigen recognition can be performed based on antigen binding specificity. When the CAR binds to its associated antigen, it affects tumor cell, causing tumor cell to fail to grow, to death or to be affected otherwise, causing the patient's tumor burden to shrink or eliminate. The antigen binding domain is preferably fused to the intracellular domain from one or more of the co-stimulatory molecule and the ζ chain. Preferably, the antigen binding domain is fused with an intracellular domain of a combination of a 4-1BB signaling domain and a CD3ζ signaling domain.

As used herein, the "antigen binding domain" and "single-chain antibody fragment" refer to an Fab fragment, an Fab' fragment, an F (ab') 2 fragment, or a single Fv fragment that has antigen-binding activity. The Fv antibody contains the heavy chain variable region and the light chain variable region of the antibody, but has no constant region. The Fv antibody has the smallest antibody fragment with all antigen-binding sites. Generally, Fv antibodies also comprise a polypeptide linker between the VH and VL domains, and can form the structure required for antigen binding. The antigen binding domain is usually a scFv (single-chain variable fragment). The size of scFv is typically ⅙ of a complete antibody. The single-chain antibody is preferably an amino acid chain sequence encoded by a nucleotide chain. As a preferred embodiment of the present invention, the scFv comprises antibodies that specifically recognize CD19 and CD20.

As for the hinge region and the transmembrane region (transmembrane domain), the CAR can be designed to comprise a transmembrane domain fused to the extracellular domain of the CAR. In one embodiment, a transmembrane domain that is naturally associated with one of the domains in the CAR is used. In some embodiments, transmembrane domains may be selected or modified by amino acid substitutions to avoid binding such domains to the transmembrane domain of the same or different surface membrane proteins, thereby minimizing the interaction with other members of the receptor complexes.

The intracellular domain in the CAR of the invention comprises the signaling domain of 4-1BB and the signaling domain of CD3ζ.

Preferably, the CAR structure of the present invention, in turn, comprises a signal peptide sequence (also known as leader sequence), an antigen recognition sequence (antigen-binding domain), a hinge region, a transmembrane region, a co-stimulatory factor signal region, and a CD3zeta signaling region (ζ chain portion). The order of connection is shown in FIG. 1.

In another preferred embodiment, the present CAR is TN-LEU-19. The antigen binding domain targeting CD20 comprises a heavy chain sequence (SEQ ID NO 1) and a light chain (VL) sequence (SEQ ID NO 2) of the single-chain variable region derived from Leu16 antibody.

```
Heavy chain sequence of single-chain variable
region (VH) derived from Leu16 antibody:
                                  (SEQ ID NO 1)
EVQLQQSGAELVKPGASVKMSCKASGYTFTSYNMHWVKQTPGQGLEWIGA

IYPGNGDTSYNQKFKGKATLTADKSSSTAYMQLSSLTSEDSADYYCARSN

YYGSSYWFFDVWGAGTTVTVSS

Light chain sequence of single-chain variable
region (VL) derived from Leu16 antibody:
                                  (SEQ ID NO 2)
DIVLTQSPAILSASPGEKVTMTCRASSSVNYMDWYQKKPGSSPKPWIYAT

SNLASGVPARFSGSGSGTSYSLTISRVEAEDAATYYCQQWSFNPPTFGGG

TKLEIK
```

In another preferred embodiment, the present CAR is TN-OF-19. The antigen binding domain targeting CD20 comprises a heavy chain sequence (SEQ ID NO 3) and a light chain sequence (SEQ ID NO 4) of the single-chain variable region derived from Ofatumumab antibody.

Heavy chain sequence of single-chain variable
region (VH) derived from Ofatumumab antibody:
(SEQ ID NO 3)
EVQLVESGGGLVQPGRSLRLSCAASGFTFNDYAMHWVRQAPGKGLEWVST

ISWNSGSIGYADSVKGRFTISRDNAKKSLYLQMNSLRAEDTALYYCAKDI

QYGNYYYGMDVWGQGTTVTVSS

Light chain sequence of single-chain variable
region (VL) derived from Ofatumumab antibody:
(SEQ ID NO 4)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPITFGQ

GTRLEIK

In another preferred embodiment, the antigen-binding domain targeting CD19 in the CAR of the present invention comprises a light chain (VL) sequence (SEQ ID NO 5) and a heavy chain sequence (SEQ ID NO 6) of the single-chain variable region derived from FMC63 antibody.

Specifically, the sequences of other elements in the CAR of the present invention are as follows:

The leader sequence is the leader sequence of CD8 antigen:
(SEQ ID NO 8)
MALPVTALLLPLALLLHAARP The linker sequences (i.e., flexible linker I) between the heavy chain and light chain of the single-chain variable region are:

Amino acid sequence:
(SEQ ID NO 19)
GGGGSGGGGSGGGGS

Nucleic acid sequence:
(SEQ ID NO 20)
ggtggcggtg gctcgggcgg tggtgggtcg ggtggcggcg gatct Amino acid sequence of the light chain of single-chain variable region
(VL) derived from FMC63 antibody:
(SEQ ID NO 5)
DIQMTQTTSSLSASLGDRVTISCRASQDISKYLNWYQQKPDGTVKLLIYHTSRLHSGVPS

RFSGSGSGTDYSLTISNLEQEDIATYFCQQGNTLPYTFGGGTKLEIT

Nucleotide sequence of the light chain of single-chain variable region
(VL) derived from FMC63 antibody:
(SEQ ID NO 21)
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggaccaagc tggagatcac a                                             321

Amino acid sequence of the heavy chain of single-chain variable region
(VH) derived from FMC63 antibody:
(SEQ ID NO 6)
EVKLQESGPGLVAPSQSLSVTCTVSGVSLPDYGVSWIRQPPRKGLEWLGVIWGSET

TYYNSALKSRLTIIKDNSKSQVFLKMNSLQTDDTAIYYCAKHYYYGGSYAMDYWGQGT

SVTVSS

Nucleotide sequence of the heavy chain of single-chain variable region
(VH) derived from FMC63 antibody:
(SEQ ID NO 22)
gaggtgaaac tgcaggagtc aggacctggc ctggtggcgc cctcacagag cctgtccgtc    60
acatgcactg tctcaggggt ctcattaccc gactatggtg taagctggat tcgccagcct   120
ccacgaaagg gtctggagtg gctgggagta atatggggta gtgaaaccac atactataat   180
tcagctctca aatccagact gaccatcatc aaggacaact ccaagagcca agttttctta   240
aaaatgaaca gtctgcaaac tgatgacaca gccatttact actgtgccaa acattattac   300
tacggtggta gctatgctat ggactactgg ggccaaggaa cctcagtcac cgtctcctca   360

-continued

The hinge region is selected from the sequence of IgG4 Hinge-CH2-CH3:

(SEQ ID NO 9)
ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK

The transmembrane region is the transmembrane region sequence of CD8 (CD8TM) or CD28 (CD28TM) antigen:

CD8TM:
(SEQ ID NO 10)
IYIWAPLAGTCGVLLLSLVITLYC

CD28TM:
(SEQ ID NO 11)
FWVLVVVGGVLACYSLLVTVAFIIFWV

The co-stimulatory factor signal region is derived from the sequence of 4-1BB or CD28 cytoplasmic signaling motif:

4-1BB:
(SEQ ID NO 12)
KRGRKKLLYIFKQPFMRPVQTTQEEDGCSCRFPEEEEGGCEL

CD28:
(SEQ ID NO 13)
RSKRSRLLHSDYMNMTPRRPGPTRKHYQPYAPPRDFAAYRS

The signaling region of CD3ζ is derived from the sequence of immunoreceptor tyrosine-based activation motif (ITAM) of CD3ζ in the TCR complex:

(SEQ ID NO 14)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

In a preferred embodiment, the complete nucleic acid sequences and amino acid sequences of the two CARs constructed in the present invention are as follows:

The complete nucleic acid sequence of TN-OF-19 is as follows:
(SEQ ID NO: 18)
ATGGCCTTACCAGTGACCGCCTTGCTCCTGCCGCTGGCCTTGCTGCTCCA

CGCCGCCAGGCCGGAAATTGTGTTGACACAGTCTCCAGCCACCCTGTCTT

TGTCTCCAGGGGAAAGAGCCACCCTCTCCTGCAGGGCCAGTCAGAGTGTT

AGCAGCTACTTAGCCTGGTACCAACAGAAACCTGGCCAGGCTCCCAGGCT

CCTCATCTATGATGCATCCAACAGGGCCACTGGCATCCCAGCCAGGTTCA

GTGGCAGTGGGTCTGGGACAGACTTCACTCTCACCATCAGCAGCCTAGAG

CCTGAAGATTTTGCAGTTTATTACTGTCAGCAGCGTAGCAACTGGCCGAT

CACCTTCGGCCAAGGGACACGACTGGAGATTAAAGGCAGTACTAGCGGTG

GTGGCTCCGGGGGCGGTTCCGGTGGGGCGGCAGCAGCGAAGTGCAGCTG

GTGGAGTCTGGGGGAGGCTTGGTACAGCCTGGCAGGTCCCTGAGACTCTC

CTGTGCAGCCTCTGGATTCACCTTTAATGATTATGCCATGCACTGGGTCC

GGCAAGCTCCAGGGAAGGGCCTGGAGTGGGTCTCAACTATTAGTTGGAAT

AGTGGTTCCATAGGCTATGCGGACTCTGTGAAGGGCCGATTCACCATCTC

CAGAGACAACGCCAAGAAGTCCCTGTATCTGCAAATGAACAGTCTGAGAG

CTGAGGACACGGCCTTGTATTACTGTGCAAAAGATATACAGTACGGCAAC

TACTACTACGGTATGGACGTCTGGGGCCAAGGGACCACGGTCACCGTCTC

CTCAGGAGGTGGTGGATCCGAGGTGAAGCTGCAGGAAAGCGGCCCTGGCC

TGGTGGCCCCCAGCCAGAGCCTGAGCGTGACCTGCACCGTGAGCGGCGTG

AGCCTGCCCGACTACGGCGTGAGCTGGATCCGGCAGCCCCCCAGGAAGGG

CCTGGAATGGCTGGGCGTGATCTGGGGCAGCGAGACCACCTACTACAACA

GCGCCCTGAAGAGCCGGCTGACCATCATCAAGGACAACAGCAAGAGCCAG

GTGTTCCTGAAGATGAACAGCCTGCAGACCGACGACACCGCCATCTACTA

CTGCGCCAAGCACTACTACTACGGCGGCAGCTACGCCATGGACTACTGGG

GCCAGGGCACCAGCGTGACCGTGAGCAGCGGCAGCACCTCCGGCAGCGGC

AAGCCTGGCAGCGGCGAGGGCAGCACCAAGGGCGACATCCAGATGACCCA

GACCACCTCCAGCCTGAGCGCCAGCCTGGGCGACCGGGTGACCATCAGCT

GCCGGGCCAGCCAGGACATCAGCAAGTACCTGAACTGGTATCAGCAGAAG

CCCGACGGCACCGTCAAGCTGCTGATCTACCACACCAGCCGGCTGCACAG

CGGCGTGCCCAGCCGGTTTAGCGGCAGCGGCTCCGGCACCGACTACAGCC

TGACCATCTCCAACCTGGAACAGGAAGATATCGCCACCTACTTTTGCCAG

CAGGGCAACACACTGCCCTACACCTTTGGCGGCGGAACAAAGCTGGAAAT

CACCGAGAGCAAGTACGGACCGCCCTGCCCCCCTTGCCCTATGTTCTGGG

TGCTGGTGGTGGTCGGAGGCGTGCTGGCCTGCTACAGCCTGCTGGTCACC

GTGGCCTTCATCATCTTTTGGGTGAAACGGGGCAGAAAGAAACTCCTGTA

TATATTCAAACAACCATTTATGAGACCAGTACAAACTACTCAAGAGGAAG

ATGGCTGTAGCTGCCGATTTCCAGAAGAAGAAGAAGGAGGATGTGAACTG

CGGGTGAAGTTCAGCAGAAGCGCCGACGCCCCTGCCTACCAGCAGGGCCA

GAATCAGCTGTACAACGAGCTGAACCTGGGCAGAAGGGAAGAGTACGACG

TCCTGGATAAGCGGAGAGGCCGGGACCCTGAGATGGGCGGCAAGCCTCGG

CGGAAGAACCCCCAGGAAGGCCTGTATAACGAACTGCAGAAAGACAAGAT

GGCCGAGGCCTACAGCGAGATCGGCATGAAGGGCGAGCGGAGGCGGGGCA

AGGGCCACGACGGCCTGTATCAGGGCCTGTCCACCGCCACCAAGGATACC

TACGACGCCCTGCACATGCAGGCCCTGCCCCCAAGG

The complete amino acid sequence of TN-OF-19 is as follows:
(SEQ ID NO: 16)
MALPVTALLLPLALLLHAARPEIVLTQSPATLSLSPGERATLSCRASQSV

SSYLAWYQQKPGQAPRLLIYDASNRATGIPARFSGSGSGTDFTLTISSLE

PEDFAVYYCQQRSNWPITFGQGTRLEIKGSTSGGGSGGGSGGGGSSEVQL

VESGGGLVQPGRSLRLSCAASGFTFNDYAMHWVRQAPGKGLEWVSTISWN

SGSIGYADSVKGRFTISRDNAKKSLYLQMNSLRAEDTALYYCAKDIQYGN

YYYGMDVWGQGTTVTVSSGGGGSEVKLQESGPGLVAPSQSLSVTCTVSGV

SLPDYGVSWIRQPPRKGLEWLGVIWGSETTYYNSALKSRLTIIKDNSKSQ
VFLKMNSLQTDDTAIYYCAKHYYYGGSYAMDYWGQGTSVTVSSGSTSGSG
KPGSGEGSTKGDIQMTQTTSSLSASLGDRVTISCRASQDISKYLNWYQQK
PDGTVKLLIYHTSRLHSGVPSRFSGSGSGTDYSLTISNLEQEDIATYFCQ
QGNTLPYTFGGGTKLEITESKYGPPCPPCPMFWVLVVVGGVLACYSLLVT
VAFIIFWVKRGRKKLLYIFKQPFMRPVQTTQEEDGCSCRFPEEEEGGCEL
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR

The complete nucleic acid sequence of TN-LEU-19 is as follows:

(SEQ ID NO: 17)
ATGGAGACAGACACACTCCTGCTATGGGTGCTGCTGCTCTGGGTTCCAGG
TTCCACAGGTGACATTGTGCTGACCCAATCTCCAGCTATCCTGTCTGCAT
CTCCAGGGGAGAAGGTCACAATGACTTGCAGGGCCAGCTCAAGTGTAAAT
TACATGGACTGGTACCAGAAGAAGCCAGGATCCTCCCCCAAACCCTGGAT
TTATGCCACATCCAACCTGGCTTCTGGAGTCCCTGCTCGCTTCAGTGGCA
GTGGGTCTGGGACCTCTTACTCTCTCACAATCAGCAGAGTGGAGGCTGAA
GATGCTGCCACTTATTACTGCCAGCAGTGGAGTTTTAATCCACCCACGTT
CGGAGGGGGGACCAAGCTGGAAATAAAAGGCAGTACTAGCGGTGGTGGCT
CCGGGGGCGGTTCCGGTGGGGCGGCAGCAGCGAGGTGCAGCTGCAGCAG
TCTGGGGCTGAGCTGGTGAAGCCTGGGGCCTCAGTGAAGATGTCCTGCAA
GGCTTCTGGCTACACATTTACCAGTTACAATATGCACTGGGTAAAGCAGA
CACCTGGACAGGGCCTGGAATGGATTGGAGCTATTTATCCAGGAAATGGT
GATACTTCCTACAATCAGAAGTTCAAAGGCAAGGCCACATTGACTGCAGA
CAAATCCTCCAGCACAGCCTACATGCAGCTCAGCAGCCTGACATCTGAGG
ACTCTGCGGACTATTACTGTGCAAGATCTAATTATTACGGTAGTAGCTAC
TGGTTCTTCGATGTCTGGGGCGCAGGGACCACGGTCACCGTCTCCTCAGG
AGGTGGTGGATCCGAGGTGAAGCTGCAGGAAAGCGGCCCTGGCCTGGTGG
CCCCCAGCCAGAGCCTGAGCGTGACCTGCACCGTGAGCGGCGTGAGCCTG
CCCGACTACGGCGTGAGCTGGATCCGGCAGCCCCCCAGGAAGGGCCTGGA
ATGGCTGGGCGTGATCTGGGGCAGCGAGACCACCTACTACAACAGCGCCC
TGAAGAGCCGGCTGACCATCATCAAGGACAACAGCAAGAGCCAGGTGTTC
CTGAAGATGAACAGCCTGCAGACCGACGACACCGCCATCTACTACTGCGC
CAAGCACTACTACTACGGCGGCAGCTACGCCATGGACTACTGGGGCCAGG
GCACCAGCGTGACCGTGAGCAGCGGCAGCACCTCCGGCAGCGGCAAGCCT
GGCAGCGGCGAGGGCAGCACCAAGGGCGACATCCAGATGACCCAGACCAC
CTCCAGCCTGAGCGCCAGCCTGGGCGACCGGGTGACCATCAGCTGCCGGG
CCAGCCAGGACATCAGCAAGTACCTGAACTGGTATCAGCAGAAGCCCGAC
GGCACCGTCAAGCTGCTGATCTACCACACCAGCCGGCTGCACAGCGGCGT
GCCCAGCCGGTTTAGCGGCAGCGGCTCCGGCACCGACTACAGCCTGACCA
TCTCCAACCTGGAACAGGAAGATATCGCCACCTACTTTTGCCAGCAGGGC

AACACACTGCCCTACACCTTTGGCGGCGGAACAAAGCTGGAAATCACCGA
GAGCAAGTACGGACCGCCCTGCCCCCCTTGCCCTATGTTCTGGGTGCTGG
TGGTGGTCGGAGGCGTGCTGGCCTGCTACAGCCTGCTGGTCACCGTGGCC
TTCATCATCTTTTGGGTGAAACGGGGCAGAAAGAAACTCCTGTATATATT
CAAACAACCATTTATGAGACCAGTACAAACTACTCAAGAGGAAGATGGCT
GTAGCTGCCGATTTCCAGAAGAAGAAGAAGGAGGATGTGAACTGCGGGTG
AAGTTCAGCAGAAGCGCCGACGCCCCTGCCTACCAGCAGGGCCAGAATCA
GCTGTACAACGAGCTGAACCTGGGCAGAAGGGAAGAGTACGACGTCCTGG
ATAAGCGGAGAGGCCGGGACCCTGAGATGGGCGGCAAGCCTCGGCGGAAG
AACCCCCAGGAAGGCCTGTATAACGAACTGCAGAAAGACAAGATGGCCGA
GGCCTACAGCGAGATCGGCATGAAGGGCGAGCGGAGGCGGGGCAAGGGCC
ACGACGGCCTGTATCAGGGCCTGTCCACCGCCACCAAGGATACCTACGAC
GCCCTGCACATGCAGGCCCTGCCCCCAAGG

The complete amino acid sequence of TN-LEU-19 is as follows:

(SEQ ID NO: 15)
METDTLLLLWVLLLWVPGSTG*DIVLTQSPAILSASPGEKVIMTCRASSSVN*
*YMDWYQKKPGSSPKPWIYATSNLASGVPARFSGSGSGTSYSLTISRVEAE*
*DAATYYCQQWSFNPPTFGGGTKLEIKGSTSGGGSGGGSGGGGS*EVQLQQ
SGAELVKPGASVKMSCKASGYTFTSYNMHWVKQTPGQGLEWIGAIYPGNG
DTSYNQKFKGKATLTADKSSSTAYMQLSSLTSEDSADYYCARSNYYGSSY
WFFDVWGAGTTVTVSSGGGGS*EVKLQESGPGLVAPSQSLSVTCTVSGVSL*
*PDYGVSWIRQPPRKGLEWLGVIWGSETTYYNSALKSRLTIIKDNSKSQVF*
*LKMNSLQTDDTAIYYCAKHYYYGGSYAMDYWGQGTSVTVSSGSTSGSGKP*
*GSGEGSTKG*DIQMTQTTSSLSASLGDRVTISCRASQDISKYLNWYQQKPD
GTVKLLIYHTSRLHSGVPSRFSGSGSGTDYSLTISNLEQEDIATYFCQQG
NTLPYTFGGGTKLEITESKYGPPCPPCPMFWVLVVVGGVLACYSLLVTVA
FIIFWVKRGRKKLLYIFKQPFMRPVQTTQEEDGCSCRFPEEEEGGCELRV
KFSRSADAPAYQQGQNQLYNELNLGRREEYDVLDKRRGRDPEMGGKPRRK
NPQEGLYNELQKDKMAEAYSEIGMKGERRRGKGHDGLYQGLSTATKDTYD
ALHMQALPPR

The Design of the BICAR of the Present Invention has the Following Advantages:

First, CD19 and CD20 are expressed in most malignant B-cell tumors. Secondly, in general, when expanding CAR structure to increase T cell recognition ability, problems such as increased adverse targeting, increased cytotoxicity, and increased side effects are often encountered. However, this is not the case for CD19 and CD20 because both of them are only expressed in B cells with the same tumor toxicity curve. Finally, the expression of CD19 and CD20 in B cells can promote the survival of B cells. And the loss of both antigens during treatment is a very low probability event. Therefore, targeting CD19 and CD20 is expected to provide effective prevention of antigen escape of malignant B cells.

Compared with the single CAR of CD19 or CD20, BICAR has the following advantages:

First, compared with expressing two independent CARs, when expressing BICAR in a single T cell, the DNA footprint is significantly reduced (the DNA length is reduced by 40%). The size and the length of structure can significantly affect the packaging and transduction efficiency of the viral vector, thus directly affecting the clinical efficacy. Secondly, compared to the mixture of two different single CARs, BICAR can significantly reduce the cost of treatment (BICAR is completely compatible with the current T cell production process without adding additional burden) and increase the clinical cure rate. Finally, CD19 and CD20 have been verified in a large number of clinical studies and are relatively safe.

In the present invention, we constructed two types of chimeric antigen receptor structures (TN-LEU-19, TH-OF-19) targeting CD19 and CD20 based on the sequence of CD19 mouse-derived monoclonal antibody FMC63 and the sequences of CD20 mouse-derived monoclonal antibody leu-16 and Ofatumumab. We completed the analysis and identification of the expression levels, in vitro activation capacity, and tumor cell killing efficacy of these two chimeric antigen receptors in primary T cells. Finally, it was found that the T-cells modified with TN-LEU-19 or TH-OF-19 chimeric antigen receptors have a strong ability to kill in vitro and to clear malignant tumors carrying CD19 and CD20 positive antigens in vivo, and Ofatumumab is better than leu16. This provides a new effective method and preparation for the clinical application of CAR-T in the treatment of CD19 and CD20-positive leukemias and lymphomas.

The present invention designed and optimized single-specific and double-specific CARs. These CARs have a powerful killing ability against B-cell malignancies expressing CD19 or CD20. BICAR allows a single T-cell product to target two clinically validated antigens associated with B-cell leukemia and lymphoma, ultimately reducing the risk of tumor recurrence due to the loss or escape of a single antigen. The invention can be further used in the design of new BICAR, thus increasing the antigen's applicability and increasing the efficacy of T cell therapy for cancer.

Chimeric Antigen Receptor T Cell (CAR-T Cell)

As used herein, the terms "CAR-T cell", "CAR-T", "CART", "CAR-T cell of the present invention" all refer to the CAR-T cell that targets both CD19 and CD20 of the forth aspect of the invention. Specifically, the CAR structure of the CAR-T cells comprises an anti-CD19 scFv, an anti-CD20 scFv, a hinge region, a transmembrane region, and an intracellular T cell signaling region in turn, wherein the anti-CD20 scFv and anti-CD19 scFv are linked with a peptide having multiple repeating structures (G4S). Compared with CAR-T targeting a single antigen, the CAR-T cell that simultaneously recognizes two targets are more lethal and have a wider range of treatment.

Vector

The nucleic acid sequences coding for the desired molecules can be obtained using recombinant methods known in the art, such as, for example by screening libraries from cells expressing the gene, by deriving the gene from a vector known to comprise the same, or by isolating directly from cells and tissues containing the same, using standard techniques. Alternatively, the gene of interest can be produced synthetically.

The present invention also provides vectors in which the expression cassette of the present invention is inserted. Vectors derived from retroviruses such as the lentivirus are suitable tools to achieve long-term gene transfer since they allow long-term, stable integration of a transgene and its propagation in daughter cells. Lentiviral vectors have the advantage over vectors derived from onco-retroviruses such as murine leukemia viruses in that they can transduce non-proliferating cells, such as hepatocytes. They also have the advantage of low immunogenicity.

In brief summary, the expression cassette or nucleic acid sequence of the invention is typically and operably linked to a promoter, and incorporated into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immune and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest comprise expression vectors, replication vectors, probe generation vectors, and sequencing vectors.

Further, the expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors comprise, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters comprise, but are not limited to a metallothionein promoter, a glucocorticoid promoter, a progesterone promoter, and a tetracycline promoter.

In order to assess the expression of a CAR polypeptide or portions thereof, the expression vector to be introduced into a ceil can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers comprise, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may comprise genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell comprise calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell comprise the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell comprise colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids comprise the fatty droplets that naturally occur in the cytoplasm as well as the class of compounds which contain long-chain aliphatic hydrocarbons and their derivatives, such as fatty acids, alcohols, amines, amino alcohols, and aldehydes.

In a preferred embodiment of the invention, the vector is a lentiviral vector.

Preparation

The invention provides a preparation comprising the CAR-T cell of the forth aspect of the invention, and a pharmaceutically acceptable carrier, diluent or excipient. In one embodiment, the preparation is a liquid preparation. Preferably, the preparation is an injection. Preferably, the concentration of the CAR-T cells in the preparation is $1\times10^3$-$1\times10^8$ cells/ml, more preferably $1\times10^4$-$1\times10^7$ cells/ml.

In one embodiment, the preparation may comprises buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The preparation of the invention is preferably formulated for intravenous administration.

Therapeutic Application

The invention comprises therapeutic applications using cells (e.g., T cells) transduced with a lentiviral vector (LV)

encoding the expression cassette of the invention. The transduced T cells can target the tumor cell markers CD19 and CD20, synergistically activate T cells, and cause T cell immune responses, thereby significantly increasing the killing efficiency against tumor cells.

Thus, the present invention also provides a method for stimulating a T cell-mediated immune response to a target cell population or tissue in a mammal comprising the step of administering to the mammal a CAR-T cell of the invention.

In one embodiment, the present invention comprises a class of cell therapies, wherein T cells from autologous patient (or heterologous donor) are isolated, activated and genetically modified to generate CAR-T cells, and then injected into the same patient. The probability of graft versus host disease in this way is extremely low, and antigens are recognized by T cells in a non-MHC-restricted manner. In addition, one CAR-T can treat all cancers that express the antigen. Unlike antibody therapies, CAR-T cells are able to replicate in vivo resulting in long-term persistence that can lead to sustained tumor control.

In one embodiment, the CAR-T cells of the invention can undergo robust in vivo T cell expansion and can persist for an extended amount of time. In addition, the CAR mediated immune response may be part of an adoptive immunotherapy approach in which CAR-modified T cells induce an immune response specific to the antigen binding moiety in the CAR. For example, an anti-CD19CD20 CAR-T cell elicits an immune response specifically against cells expressing CD19 and CD20.

Although the data disclosed herein specifically discloses lentiviral vector comprising CD19CD20 scFv, hinge and transmembrane domain, and 4-1BB and CD3ζ signaling domains, the invention should be construed to comprise any number of variations for each of the components of the construct as described elsewhere herein.

Cancers that may be treated comprise tumors that are unvascularized or largely unvascularized, and tumors that are vascularized. Cancers may comprise non-solid tumors (such as hematological tumors, for example, leukemias and lymphomas) or solid tumors. Types of cancers to be treated with the CARs of the invention comprise, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also comprised.

Hematologic cancers are cancers of the blood or bone marrow. Examples of hematological (or hematogenous) cancers comprise leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, comprise fibrosarcoma, myxosarcoma, liposarcoma, mesothelioma, malignant lymphoma, pancreatic cancer and ovarian cancer.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expaning the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

The present invention provides methods for treating tumors comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2, IL-17 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunotherapeutic agents. In a further embodiment, the cell compositions of the present invention are administered to a patient in conjunction with (e.g., before, simultaneously or following) bone marrow transplantation, or the use of chemotherapy agents such as, fludarabine, external-beam radiation therapy (XRT), cyclophosphamide. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for patient administration can be performed according to art-accepted practices. In general, $1 \times 10^6$ to $1 \times 10^{10}$ of the modified T cells of the invention (e.g., CAR-T-19/20 cells) can be applied to patients by means of, for example, intravenous infusion each treatment or each course of treatment.

The Advantages of the Present Invention are (1) As for the chimeric antigen receptor of the present invention, the extracellular antigen binding domain is specific anti-CD20 scFv and anti-CD19 scFv; the CAR formed by combining the specific anti-CD20 scFv and anti-CD19 scFv to a specific hinge region and an intracellular domain shows a great ability of killing tumor cells with low cytotoxicity and low side effects.

(2) The chimeric antigen receptor provided by the invention can achieve stable expression and membrane localization of CAR protein after T cells are infected by lentivirus carrying CAR gene.

(3) The CAR-modified T cell of the present invention has a longer survival time in vivo and strong anti-tumor efficacy; the optimized CAR with the IgG4 Hinge-CH2-CH3 linker region can avoid the binding of the Fc receptor and the subsequent ADCC effect (antibody-dependent cytotoxicity).

(4) Compared with two independent CARs, the bispecific chimeric antigen receptor of the present invention comprises both anti-CD20 scFv and anti-CD19 scFv, and the DNA footprint is significantly reduced (the DNA length is reduced by 40%), and the size of structure is small, which is beneficial for the packaging and transduction efficiency of viral vectors, thus directly improving clinical efficacy. In addition, the bispecific CAR of the invention has lower cost, higher cure rate, and more safety.

(5) The T-cells modified with TN-LEU-19 or TH-OF-19 chimeric antigen receptors of the present invention have very strong ability to kill in vitro and to clear malignant tumors carrying CD19 and CD20 positive antigens in vivo, and Ofatumumab is stronger. This provides a new effective method and preparation for the clinical application of CAR-T in the treatment of CD19 and CD20-positive leukemias and lymphomas.

(6) The CAR-T cells of the present invention have a killing effect on most malignant B-cell tumors, have a wider treatment range and a larger coverage rate, and can more effectively prevent tumor cells from escaping.

The present invention will be further illustrated below with reference to the specific examples. It is to be understood that these examples are for illustrative purposes only and are not intended to limit the scope of the invention. The experimental methods with no specific conditions described in the following examples are generally performed under the conventional conditions, or according to the manufacturer's instructions. Percentages and parts are by weight unless otherwise stated.

Example 1 Construction of Lentiviral Expression Vector

The full-length DNA was synthesized and cloned to achieve the construction of encoding plasmids. The pWPT lentiviral vector was selected as a cloning vector, and the cloning sites were BamH I and Sal I sites. Wherein, the structures of the two CARs designed in the present invention are shown in FIG. 1. The nucleic acid sequence of TN-LEU-19 is shown in SEQ ID NO 17, and the nucleic acid sequence of TN-OF-19 is shown in SEQ ID NO 18.

Example 2 Preparation of CAR-T Cells (1) Mononuclear cells (PBMCs) were isolated from venous blood of healthy people by density gradient centrifugation.

(2) On day 0, PBMCs were seeded in a cell culture flask previously coated with CD3 monoclonal antibody (OKT3) at a final concentration of 5 μg/mL and Retronectin (purchased from TAKARA) at a final concentration of 10 μg/mL. The medium was GT-551 cell culture medium containing 1% human albumin. Recombinant human interleukin 2 (IL-2) was added to the medium at a final concentration of 1000 U/mL. The cells were cultured in an incubator with a saturated humidity and 5% $CO_2$ at 37° C.

(3) On day 1, the supernatant of the PBMCs culture was slowly aspirated and discarded. New GT-551 cell culture medium containing 1% human albumin was added, and recombinant human interleukin 2 (IL-2) was added to the medium at a final concentration of 1000 U/mL. The cells were continuously cultured in an incubator with a saturated humidity and 5% $CO_2$ at 37° C.

(4) On day 3, fresh medium, concentrated and purified TN-LEU-19 or TN-OF-19 lentivirus solution, protamine sulfate (12 ug/ml), and IL-2 (at a final concentration of 1000 U/mL) were added. After 12 hours of infection in a 5% $CO_2$ incubator at 37° C., the culture medium was discarded, and fresh medium was added, and cultivation was continued in a 5% $CO_2$ incubator at 37° C.

(5) Starting from day 6, CAR-T19/20s (CART-TN-OF-19 and CART-TN-LEU-19) cells can be taken for corresponding activity assay.

Example 3 Detection of the Integration Rate of the CAR Gene in the T Cell Genome and the Expression Level of the Encoded Protein Thereof on the Membrane Surface $0.5 \times 10^6$ CAR-T19/20s cell sample cultured 7 days in Example 2 were taken respectively to test the transfection efficiency of the combined chimeric antigen receptor engineered T cells targeting CD19 and CD20. Protein L method was used to identify the expression level of CAR gene-encoded protein on the surface of T cell membrane in CAR-T19/20s cells cultured 7 days.

Figure 2:
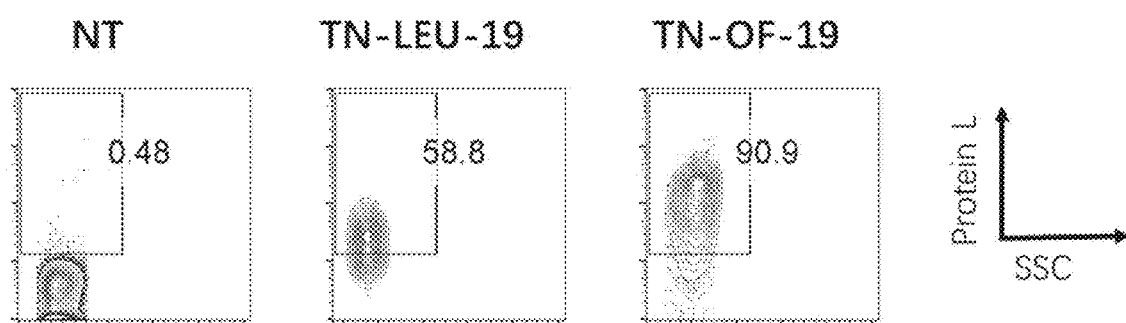
FIG. 2 shows the detection of transfection efficiency of engineered T cell with combined chimeric antigen receptors targeting CD19 and CD20. Protein L method was used to identify the expression level of CAR gene-encoded protein on the surface of T cell membrane in CAR-T19/20s cells cultured 7 days.

The result is shown in FIG. 2, and two CAR structures (FIG. 1) designed in the present invention can be expressed in their corresponding modified T cells and complete the cell membrane surface localization.

Example 4 Detection of the In Vitro Activation Ability of CAR-T19/20s

Cell activation level indicator proteins CD137 and IFNγ was detected using CAR-T19/20s cells cultured 7 days in Example 2. $1 \times 10^5$ of CART-T19/20 cells cultured 7 days were taken and cultured respectively with CD19, CD20-positive K562–CD19+, K562–CD20+, K562–CD19+CD20+ and Raji (naturally expressing CD19 and CD20) tumor cell line, as well as CD19CD20-negative K562 tumor cell line, or without tumor cells, in 200 μl of GT-551 medium for 18 h with a ratio of 1:1. Then the expression level of CD137 on the surface of T cell membrane and the secretion level of IFNγ in the culture supernatant were detected respectively.

Figure 3A:
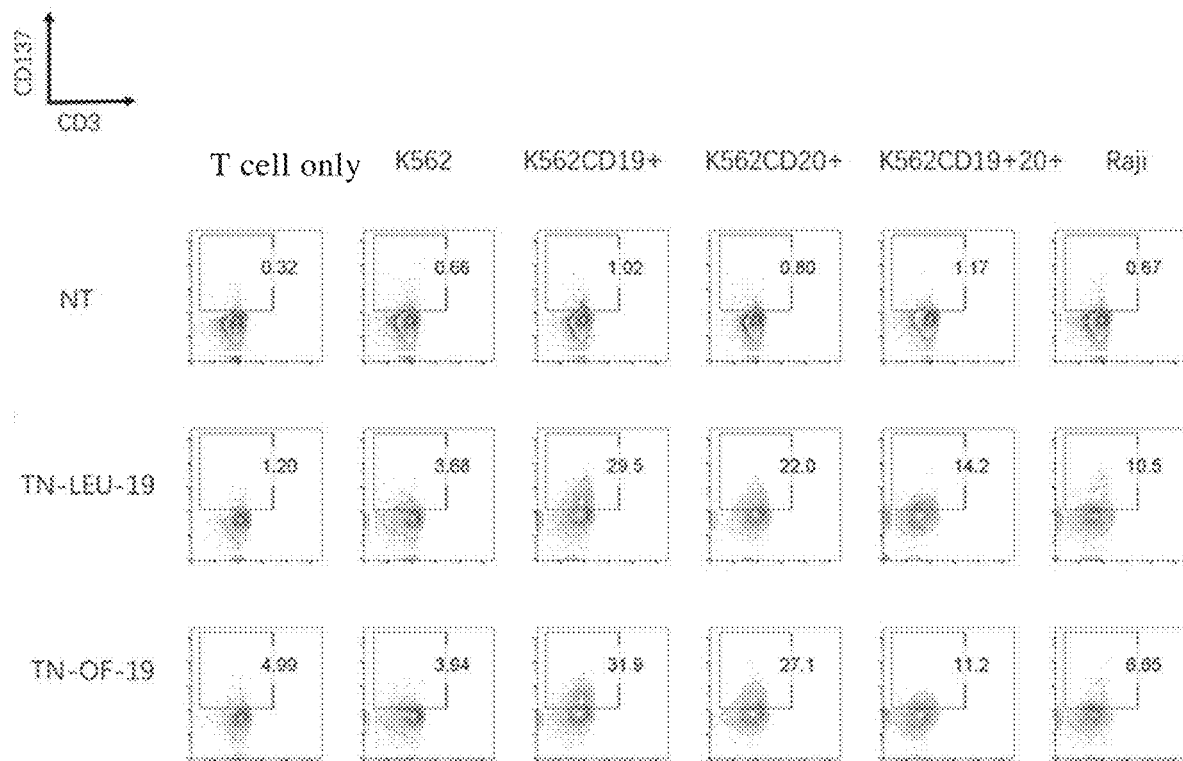
FIGS. 3A and 3B show the expression level of CD137 on the surface of T cell membrane (FIG. 3A) and the secretion level of IFNγ in the culture supernatant (FIG. 3B). Specifically, $1 \times 10^5$ of CAR-T19/20s cells cultured 7 days were taken and cultured respectively with CD19-positive K562-CD19+ tumor cell line, CD20-positive K562-CD20+ tumor cell line, CD19 and CD20 double positive K562-CD19+CD20+ tumor cell line, RAJI tumor cell line that naturally expresses CD19 and CD20, and CD19 and CD20 double negative K562 tumor cell line, or without tumor cells, in 200 μl of GT-551 medium for 18 h with a ratio of 1:1. Then the expression level of CD137 on the surface of T cell membrane and the secretion level of IFNγ in the culture supernatant were detected respectively.
Figure 3B:
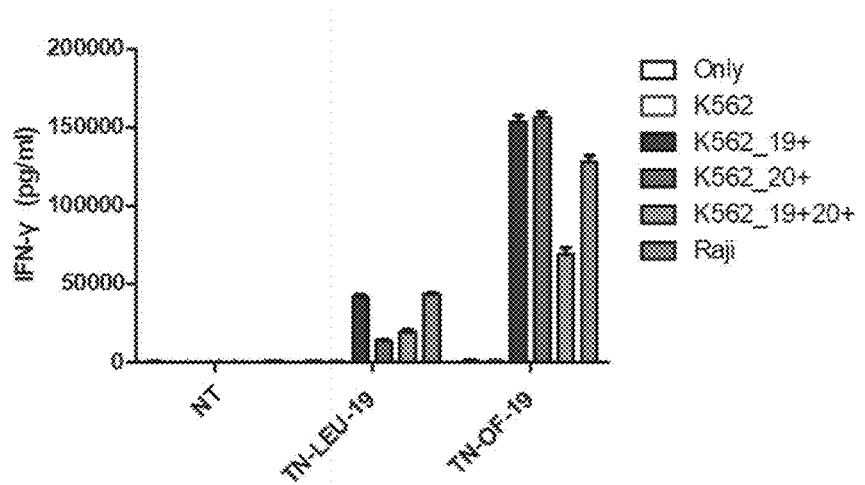

The results are shown in FIGS. 3A and 3B, the expressions of CD137 on the surface of two CART cells were detected, and the expressions of IFNγ in the culture supernatants were detected. Wherein, TN-OF-19 has higher CD137 activation level and IFNγ release level than TN-LEU-19.

Example 5 Detection of LDH Levels Released by CAR-T19/20s Cells for Killing Targeted Tumors In Vitro The CAR-T19/20s cells prepared in Example 2 were tested as follows:

Experimental wells, effector cell control wells, target cell control wells, target cell maximum release wells, medium control wells, and volume control wells (target cells comprise CD19, CD20 positive K562-CD19, K562-CD20, K562-CD19-CD20, and Raji cells; and effector cells comprise NT, CART-TN-LEU-19, and CART-TN-OF-19) were set.

The effect-target ratio was set, wherein number of effector cells:number of target cells=5:1, 10:1, 20:1, and 40:1. Number of cells: $1 \times 10^4$ of target cells, 50 ul/well; and effective cells are $5 \times 10^4$ cells/well, $1 \times 10^5$ cells/well, $2 \times 10^5$ cells/well, and $5 \times 10^5$ cells/well. Different dilution ratios of effector cells and target cells were added to the experimental wells with an effect-target ratio of 5:1, 10:1, 20:1, and 40:1. A total of 100 ul of the two cells (50 ul of effector cells+50 ul of target cells) were added to the cell culture plate, wherein 3 repeats were set. As for effector cell control wells, i.e. effector cells:target cells=5:0, 10:0, 20:0, and 40:0, $5 \times 10^4$/well, $10^5$/well, $2 \times 10^5$/well, $5 \times 10^5$/well of effector cells and 50 ul medium were added, wherein 2 repeats were set. As for target cell control wells, $1 \times 10^4$/well, 50 ul of target cell and 50 ul medium were added. As for target cells maximum release wells, $1 \times 10^4$, 50 ul of target cells and 50 ul medium were added. 10 ul lysate was added after incubating for 3 h and 15 min. As for the medium control wells, 100 ul medium was added. As for the volume control well, 100 ul medium was added.

After incubating for 3 h and 15 min, while adding 10 ul of lysate to the target cell maximum release wells, 10 ul of lysate was added and incubated at 37° C. The mixture was centrifuged at 250 g for 4 min and 50 ul/well of cell supernatant was transferred to a new enzyme plate. 50 ul/well of substrate mixture was added (kept in dark, with 12 ml of detection buffer added to a bottle of substrate mixture). The mixture was incubated at room temperature in dark for 30 min. Finally, 50 ul/well stop solution was added. The plate was read at 490 nm in 1 h, and the data was analyzed.

Figure 4:
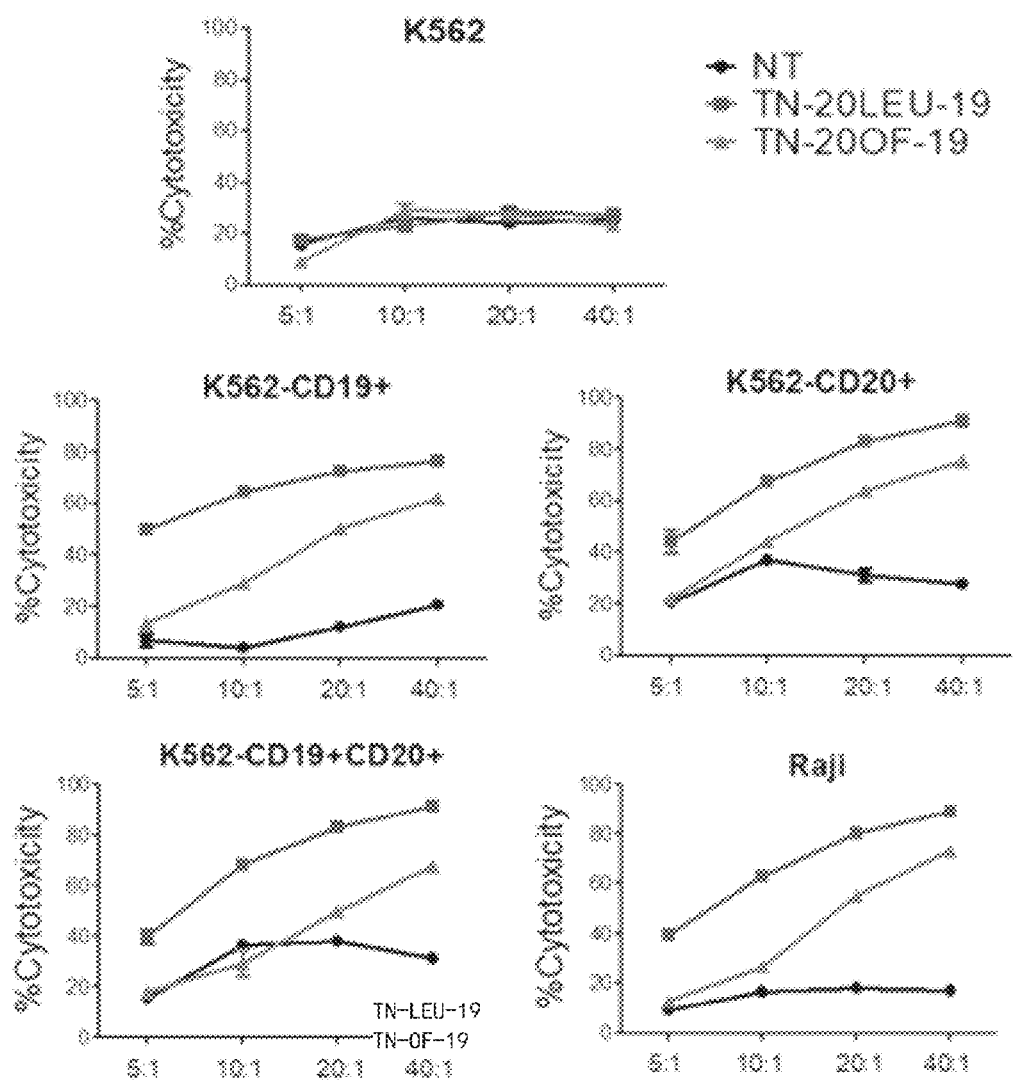
FIG. 4 shows the detection of tumor-killing activity of CAR-T19/20s cells, mainly by detecting the secretion level of LDH in the supernatant after co-culture. Specifically, $1 \times 10^4$ cells of CD19-positive K562-CD19+ tumor cell line, CD20-positive K562-CD20+ tumor cell line, CD19 and CD20 double positive K562-CD19+CD20+ tumor cell line, RAJI or RAMOS tumor cell line that naturally expresses CD19 and CD20, or CD19 and CD20 double negative K562 tumor cell line were co-cultured with the corresponding T cells, respectively, in 100 μl of GT-551 medium for 8 h with a ratio as shown in the figure. Then the secretion level of LDH was detected, and this figure shows the statistical analysis results of the percentages of LDH release in corresponding co-culture samples.

The results are shown in FIG. 4. Both CART cells can well induce apoptosis and release LDH in BCMA-positive tumor cells. Wherein, CART-TN-LEU-19 can better kill CD19CD20 positive tumor cells, and release higher LDH and the like than CART-TN-OF-19.

Example 6 Detection of CD107a Release Level During Tumor Cell Killing Induced by CAR-T19/20s Cells $1 \times 10^5$ cells of effective cell CAR-T19/20s (CART-TN-OF-19 and CART-TN-LEU-19) were co-cultured respectively with $2 \times 10^5$ of target tumor cells. The target cells are K562–CD19+, K562–CD20+, K562–CD19+CD20+, and K562 cells, Raji cells, Romas cells, respectively. At the same time, 3 μl of Anti-Human CD107Ape was added to each well for staining and placed at 37° C., 5% CO 2 for 1 hour, and then 3 μl of 1% Golgistop was added and placed at 37° C., 5% $CO_2$ for 3.5 hours. Next, 2 μl of CD8 FITC and 1.5 μl of CD3APC were added to each well and incubated at 37° C., 5% $CO_2$ for 30 min. 200 uL of FACS Buffer was added to each well and centrifuged at 300 g for 5 min. The liquid in the microplate was quickly discarded, and the remaining liquid was removed with absorbent paper. The plate was washed with FACS Buffer again. The plate was stained with 7-AAD and diluted with FACS Buffer (1:300). 200 uL of resuspended cells were added to each well. The plate was detected by flow cytometry after 10 min, light avoided. The results were statistically analyzed.

Figure 5:
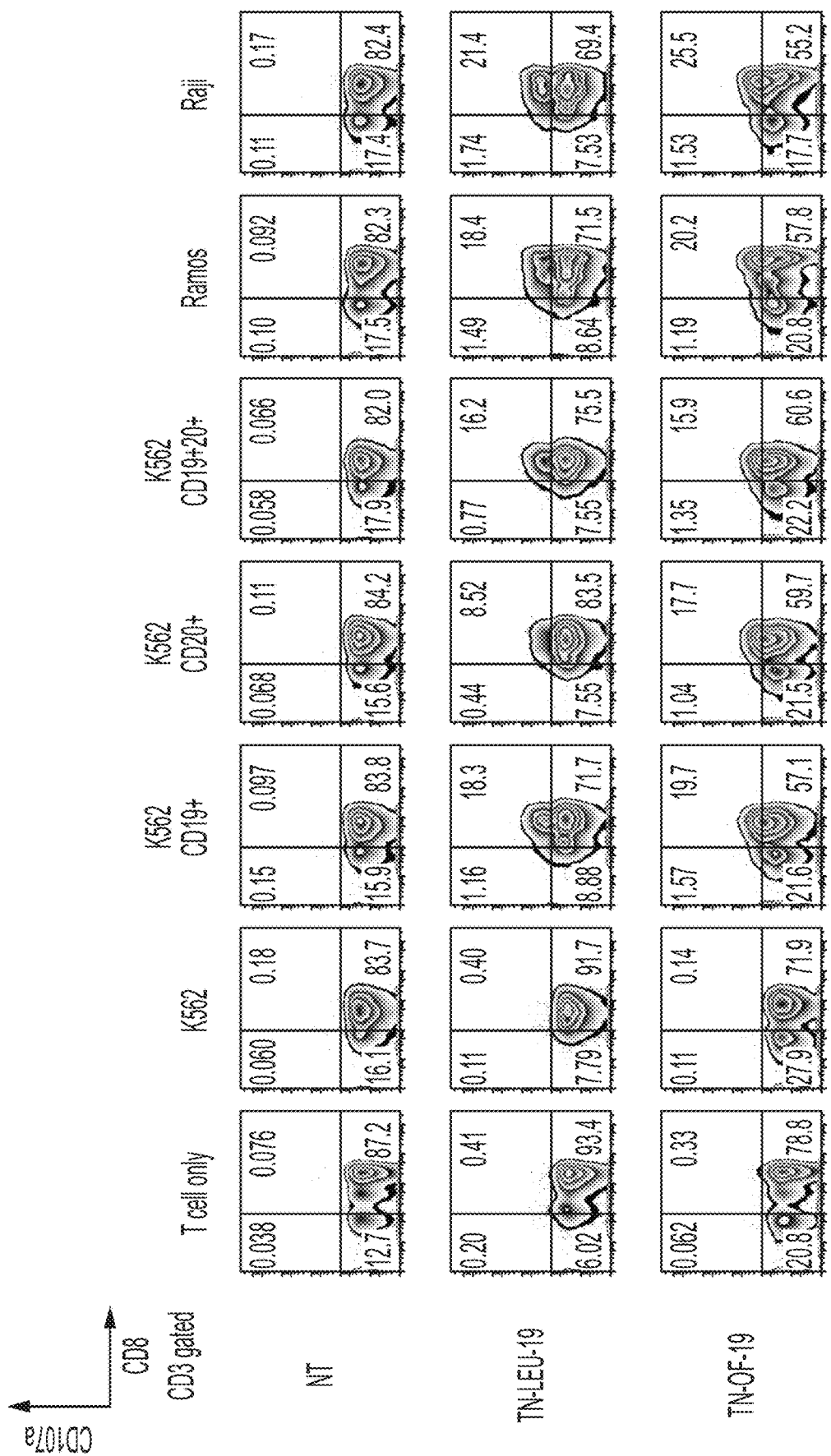
FIG. 5 shows the detection of tumor-killing activity of CAR-T19/20s cells, mainly by detecting the expression level of CD107a on the surface of T cell membrane. Specifically, $1 \times 10^5$ CAR-T19/20s cells were taken and cultured respectively with CD19-positive K562-CD19+ tumor cell line, CD20-positive K562-CD20+ tumor cell line, CD19 and CD20 double positive K562-CD19+CD20+ tumor cell line, RAJI or RAMOS tumor cell line that naturally expresses CD19 and CD20, and CD19 and CD20 double negative K562 tumor cell line, or without tumor cells, in 200 μl of GT-551 medium for 4 h with a ratio of 1:2. Then the expression level of CD137 on the surface of T cell membrane was detected respectively.

The results are shown in FIG. 5. Both CART cells can well induce the release of CD107a during tumor cell killing.

Wherein, CART-TN-OF-19 have a slightly higher release of CD107a in the killing process and a stronger killing effect than CART-TN-LEU-19.

Example 7 Inhibitory Effect of CAR-T19/20s on Transplanted Tumor Cells in Mice

The tumor cells injected in animals are Raji. The tumor cells Raji carry a luciferase reporter gene (Raji expressing luciferase). In this experiment, tumor cells Raji were injected and grown in mice for one week, and then effector T cells were injected. The effector T cells were divided into three groups: NT, CART-TN-LEU-19, and CART-TN-OF-19.

Figure 6A:
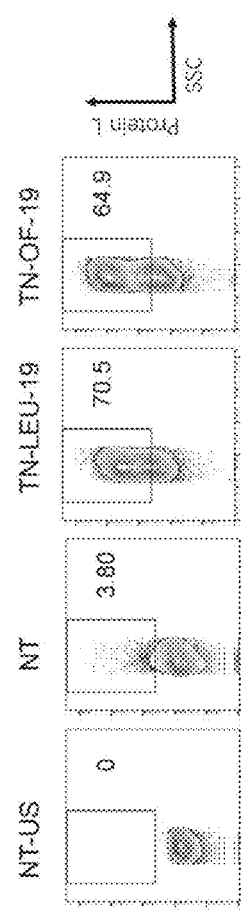
FIGS. 6A-6F shows the results of CAR-T19/20s cells killing tumor cells in RAJI-Luc/NSG leukemia model mice.
Figure 6B:
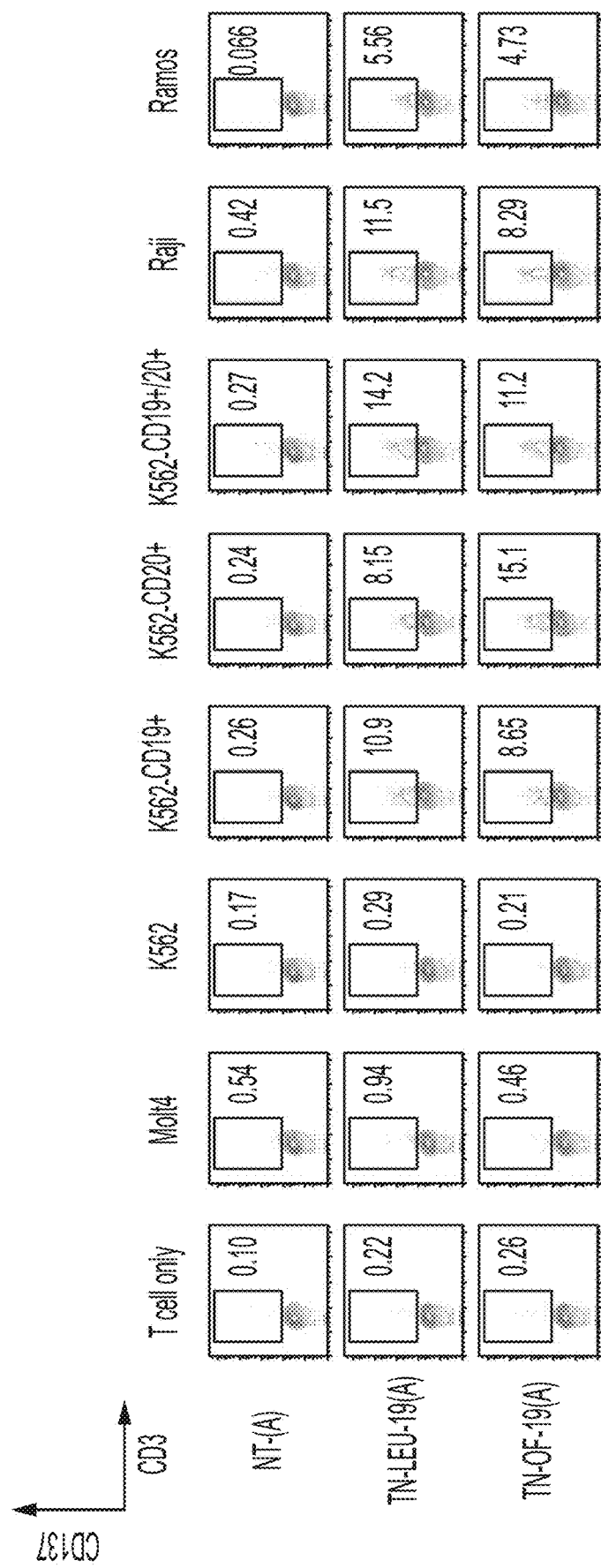
Figure 6C:
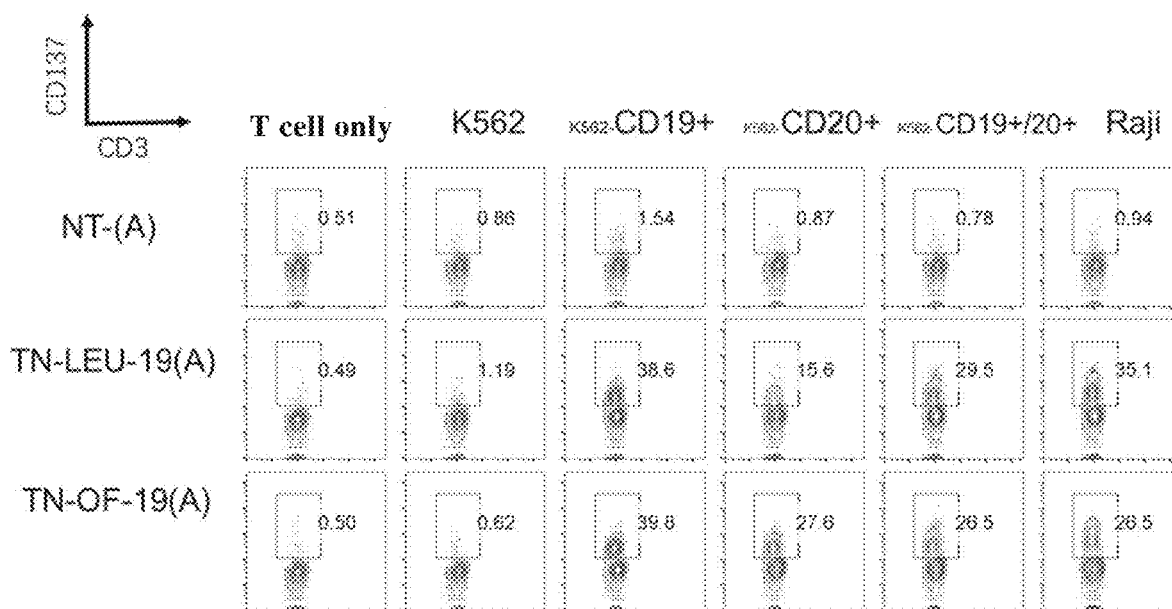
Figure 6D:
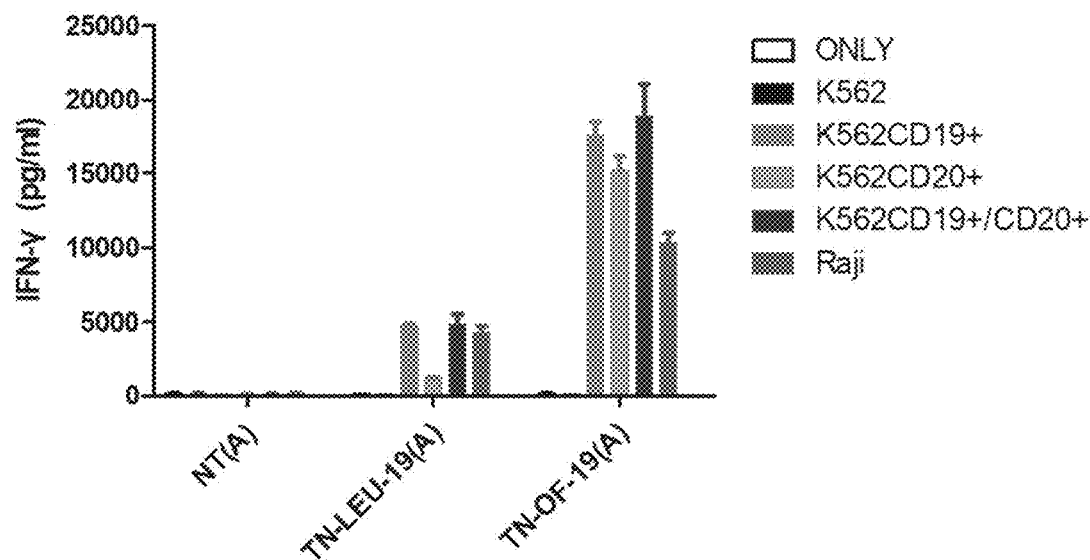

FIG. 6A shows the Protein L method for the detection of the transfection efficiency of combined chimeric antigen receptor engineered T cells targeting CD19CD20. The expression level of CD137 and the secretion level of IFNγ in the culture supernatant were the same as before. FIG. 6A shows the TN-LEU-19, TN-OF-19 both have high transfection efficiency. FIGS. 6B and 6C show the expression levels of CD137 on the surface of T cell membranes on the 10th day and the 18th day. Both TN-LEU-19 and TN-OF-19 can be expressed at high levels. FIG. 6D shows the secretion level of IFNγ in the culture supernatant on the 10th day. The results show that the level in TN-OF-19 is significantly higher than that in TN-LEU-19.

On the 21st day, the expanded effector T cells (sent to the Animal Experimental Center of Nanjing Medical University) were injected into the mice through the tail vein, and then the fluorescence intensity of the mice (via IVIS fluorescence imaging) and the weight of the mice were recorded every 7 days. The experiment was stopped on the 21st day, and the statistical results were analyzed.

Figure 6E:
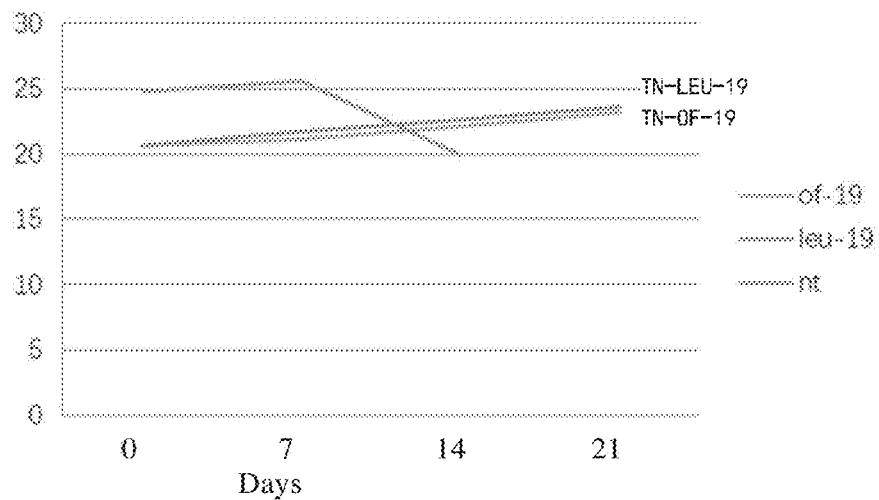
Figure 6E:
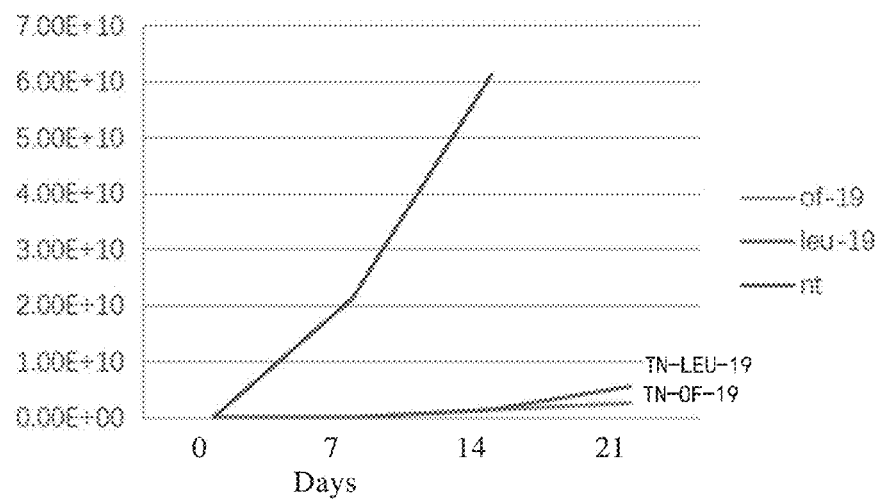

The results are shown in FIG. 6E. Both CART-TN-OF-19 and CART-TN-LEU-19 CART cells can well inhibit the growth of mouse tumor cells compared with NT. FIG. 6E (left) shows the weight change of mice after the injection of effector T cells into the three groups of mice. Compared with two types of CART cells CART-TN-OF-19 and CART-TN-LEU-19, the mice of NT showed a significant decrease in body weight and the mice in both CART cell groups gained slightly more weight. FIG. 6E (right) shows the average fluorescence intensity of the three groups of mice. The results show that the average fluorescence intensity of the mice in the NT group increased significantly, while the average of the fluorescence intensities of the mice in the two CART cell groups decreased significantly, and even difficult to detect.

Figure 6F:
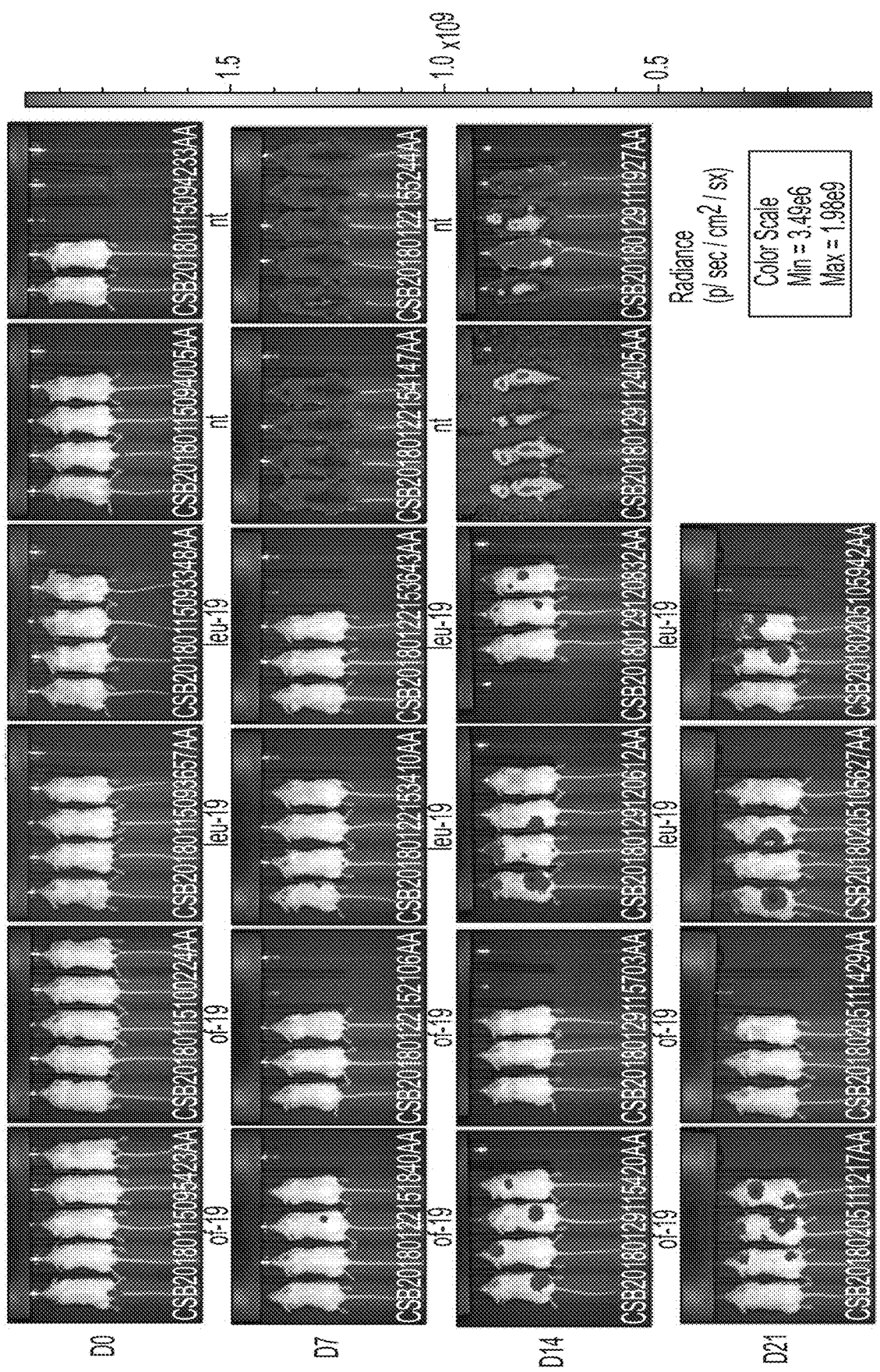

FIG. 6F shows the IVIS imaging of fluorescence intensity in mice. The results showed that after the injection of effector T cells in the tail vein, the fluorescence intensities of the mice in the two CART cell groups were very weak after the 7th day, while that of NT group was very strong. The situation on 14th day was the same. The mice in NT group had all died on the 21st day, while the mice in the two CART cell groups were still growing normally.

Example 8 Screening and Functional Verification of CAR-T20.1, CAR-T20.2 and CAR-T20.4

The construction and detection of CART cells were performed with reference to Examples 2, 3, 4, and 5.

First, full-length DNA was synthesized and cloned to achieve the construction of encoding plasmids. CAR-T 20.1, 20.2 and 20.4 were designed (the structures are shown in Table 1 and the sequences are shown in Table 2), and then the functional verification was performed.

PBMCs were thawed and infected to obtain CAR-T20s cells. Starting from day 6, CAR-T20s cells can be taken for the corresponding activity assay.

$0.5 \times 10^6$ cells of CAR-T20s cell sample cultured 7 days were taken and detected for the cell transfection efficiency by DNA copy number.

Figure 7A:
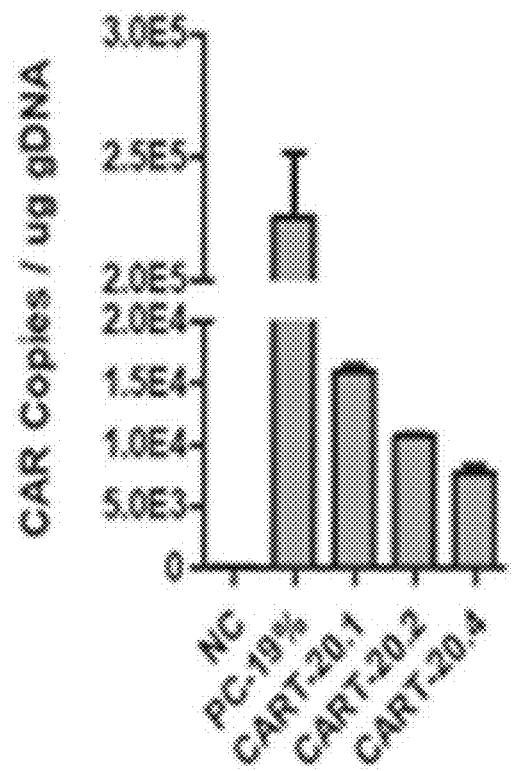
FIGS. 7A-7C show the preliminary functional verification results of CAR-T20.1, CAR-T20.2, and CAR-T20.4.

The results are shown in FIG. 7A. Compared to the positive control, the DNA copy number was not very high. Next, co-culture was performed, and CAR-T20s cells cultured for 7 days were used to detect the indicator proteins CD137 and IFNγ of the cell activation level.

$1 \times 10^5$ of CAR-T20 cells cultured for 7 days were taken and cultured respectively with CD20-positive cells Raji, Ramos and negative cells K562, Karpas tumor cell line for 18 h with a ratio of 1:1. Then the expression levels of CD137 on the surface of T cell membrane and the secretion levels of IFNγ in the culture supernatant were detected respectively.

Figure 7B:
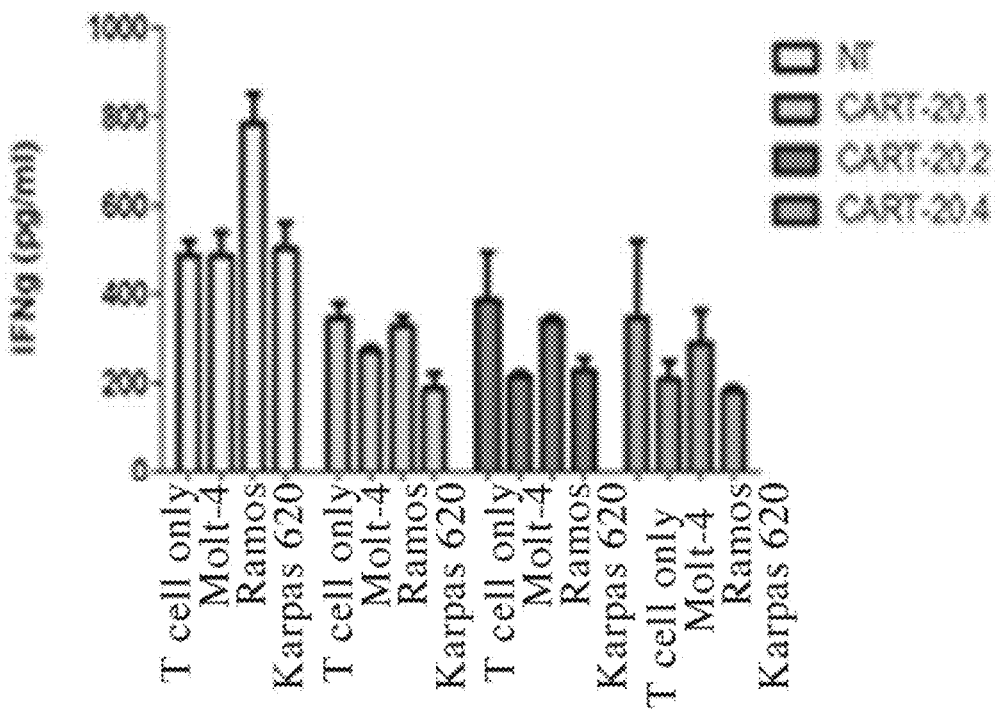
Figure 7C:
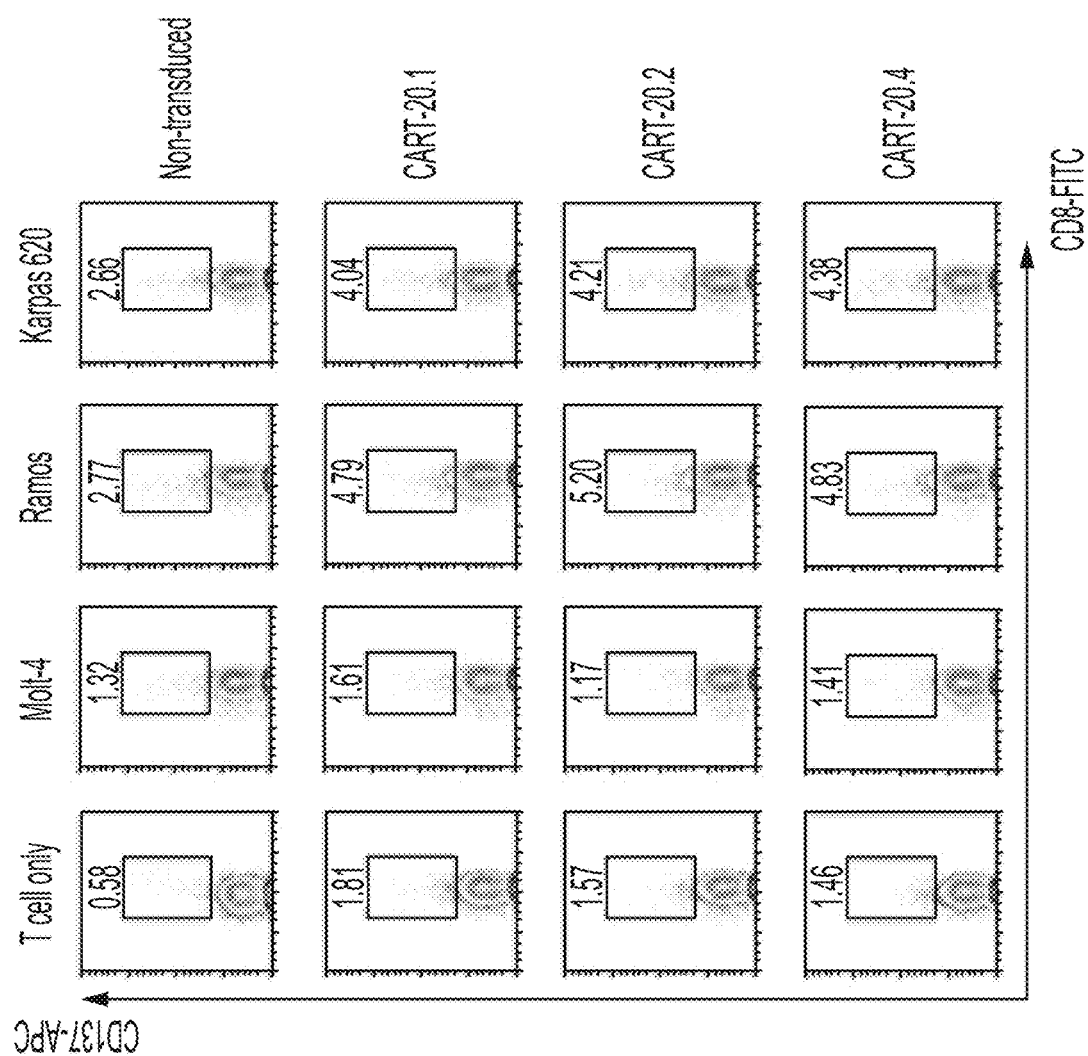

The results are shown in FIGS. 7B and 7C. CAR-T20.1, CAR-T20.2 and CAR-T20.4 constructed in this example are invalid.

Example 9 Screening and Functional Verification of CAR-T20.5, CAR-T20.6, CAR-T20.7, CAR-T20.8, CAR-T20.9 and CAR-T20.10

The construction and detection of CART cells were performed with reference to Examples 2, 3, 4, and 5.

First, full-length DNA was synthesized and cloned to achieve the construction of encoding plasmids. CAR-T20.5, CAR-T20.6, CAR-T20.7, CAR-T20.8, CAR-T20.9 and CAR-T20.10 were designed (the structures are shown in Table 1 and the sequences are shown in Table 2), and then the functional verification was performed.

PBMCs were thawed and infected to obtain CAR-T20s cells. Starting from day 6, CAR-T20s cells can be taken for the corresponding activity assay.

$0.5 \times 10^6$ cells of CAR-T20s cell sample cultured$^7$ days were taken and detected for the T cell transfection efficiency. Protein L method was used to identify the expression level of CAR gene-encoded protein on the surface of T cell membrane in CAR-T20s cells cultured for 7 days.

Figure 8A:
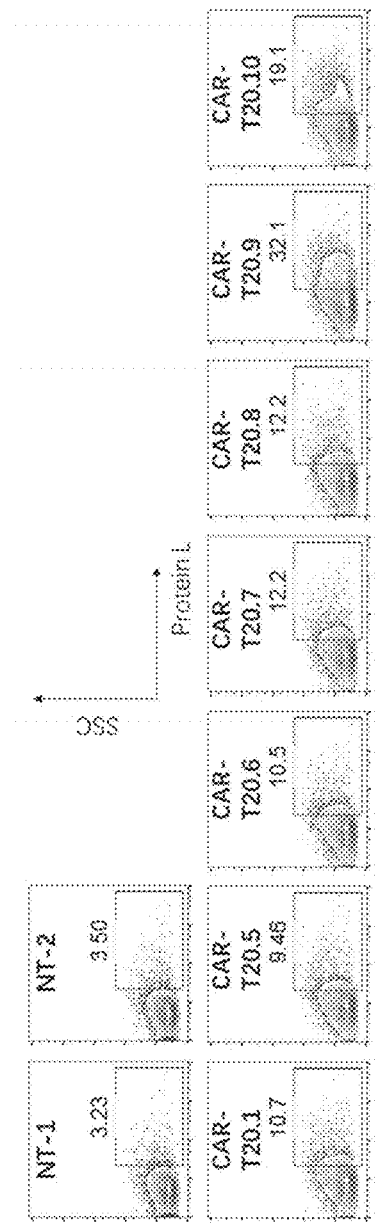
FIGS. 8A-8C show the functional verification results of CAR-T20.5, CAR-T20.6, CAR-T20.7, CAR-T20.8, CAR-T20.9 and CAR-T20.10.

The results are shown in FIG. 8A. Compared with CAR-T20.1, among CAR-T20.5, CAR-T20.6, CAR-T20.7, CAR-T20.8, CAR-T20.9 and CAR-T20.10, only CAR-T20.9 and CAR-T20.10 had a higher positive rate.

Next, co-culture was performed, and CAR-T20s cells cultured for 7 days were used to detect the indicator proteins CD137 and IFNγ of the cell activation level. $1 \times 10^6$ of CAR-T20s cells cultured for 7 days were cultured respectively with CD20-positive cells Raji, Ramos and negative cells K562, Karpas tumor cell line for 18 h with a ratio of 1:1. Then the expression levels of CD137 on the surface of T cell membrane and the secretion levels of IFNγ in the culture supernatant were detected respectively.

Figure 8B:
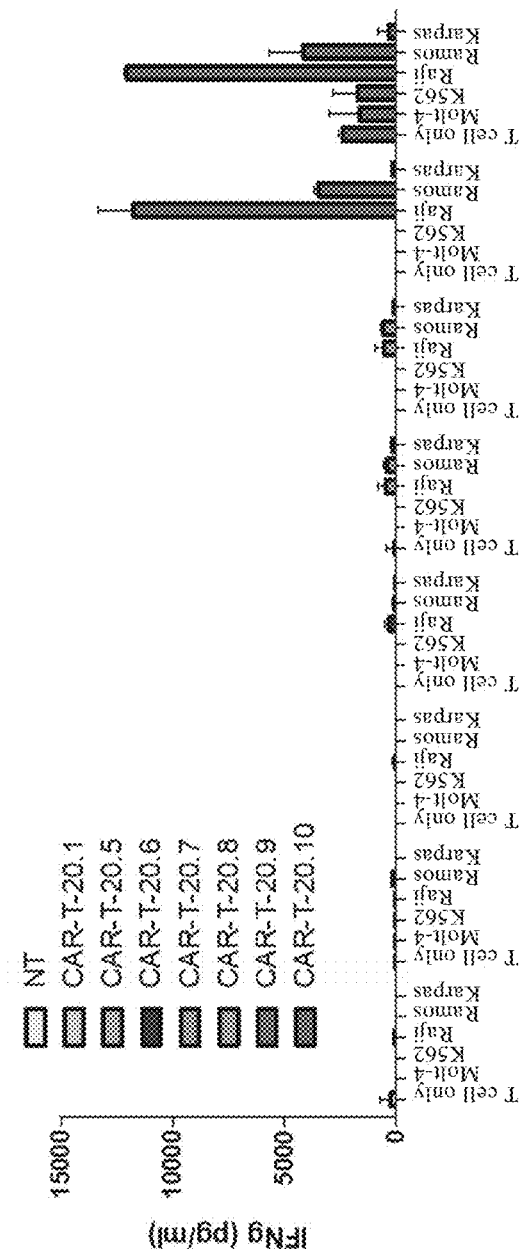
Figure 8C:
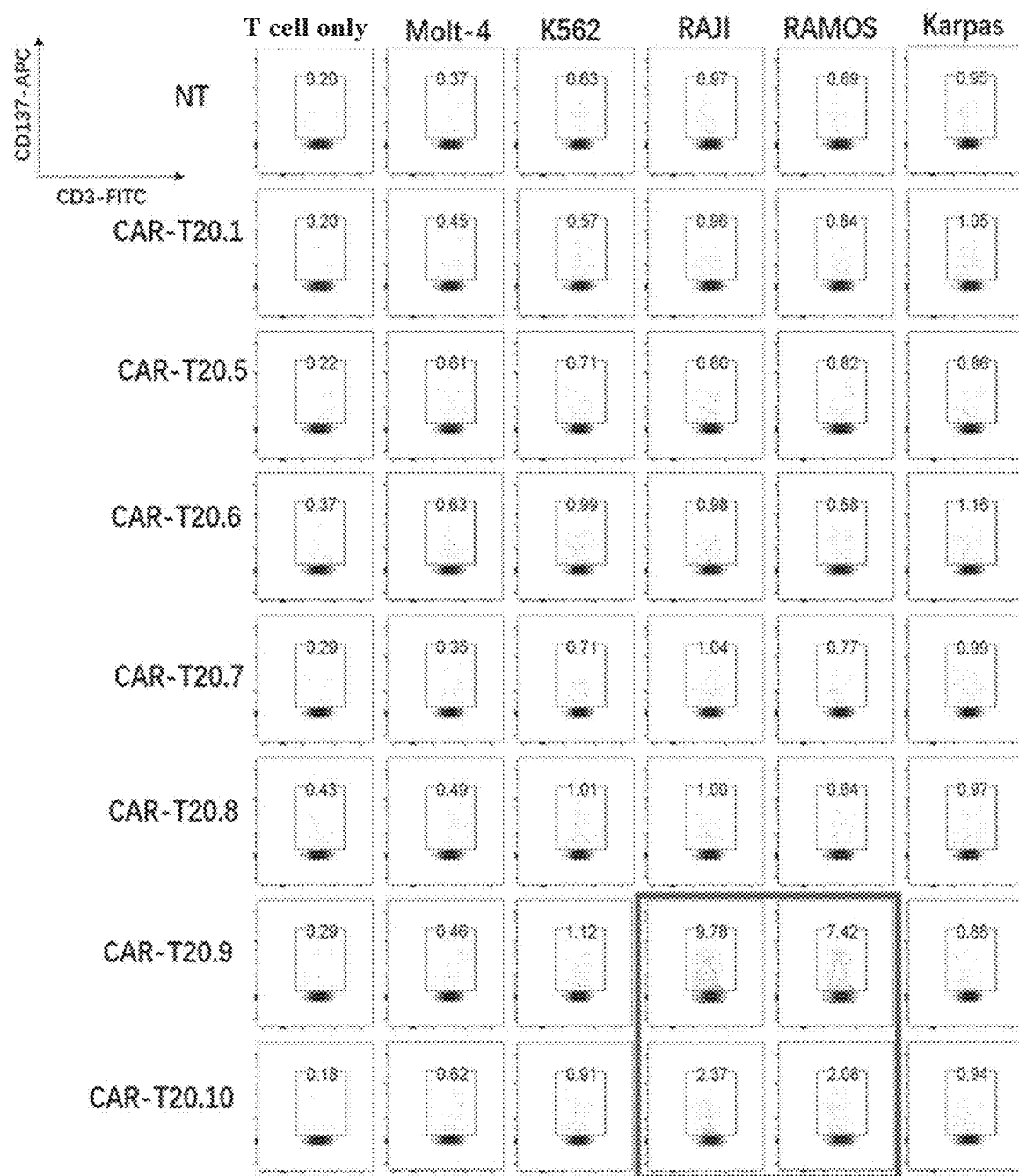

The results are shown in FIGS. 8B and 8C. The results show that among CAR-T20.5, CAR-T20.6, CAR-T20.7, CAR-T20.8, CAR-T20.9 and CAR-T20.10, only in CAR-T20.9 and CAR-T20.10, the expression levels of CD137 on the surface of T cell membrane were activated and IFNγ was released in the culture supernatant. That is, CAR-T20.9 and CAR-T20.10 are effective.

Example 10 Screening and Functional Verification of CAR-T20.11, CAR-T20.12, CAR-T20.13, CAR-T20.14, CAR-T20.15 and CAR-T20.16

The construction and detection of CART cells were performed with reference to Examples 2, 3, 4, and 5.

First, full-length DNA was synthesized and cloned to achieve the construction of encoding plasmids. CAR-T20.11, CAR-T20.12, CAR-T20.13, CAR-T20.14, CAR-T20.15 and CAR-T20.16 were designed (the structures are shown in Table 1 and the sequences are shown in Table 2), and then the functional verification was performed.

PBMCs were thawed and infected to obtain CAR-T20s cells. Starting from day 6, CAR-T20s cells can be taken for the corresponding activity assay.

$0.5 \times 10^6$ of CAR-T20s cells sample cultured for 7 days were taken and detected for the T cell transfection efficiency. Protein L method was used to identify the expression level of CAR gene-encoded protein on the surface of T cell membrane in CAR-T20s cells cultured for 7 days.

Figure 9A:
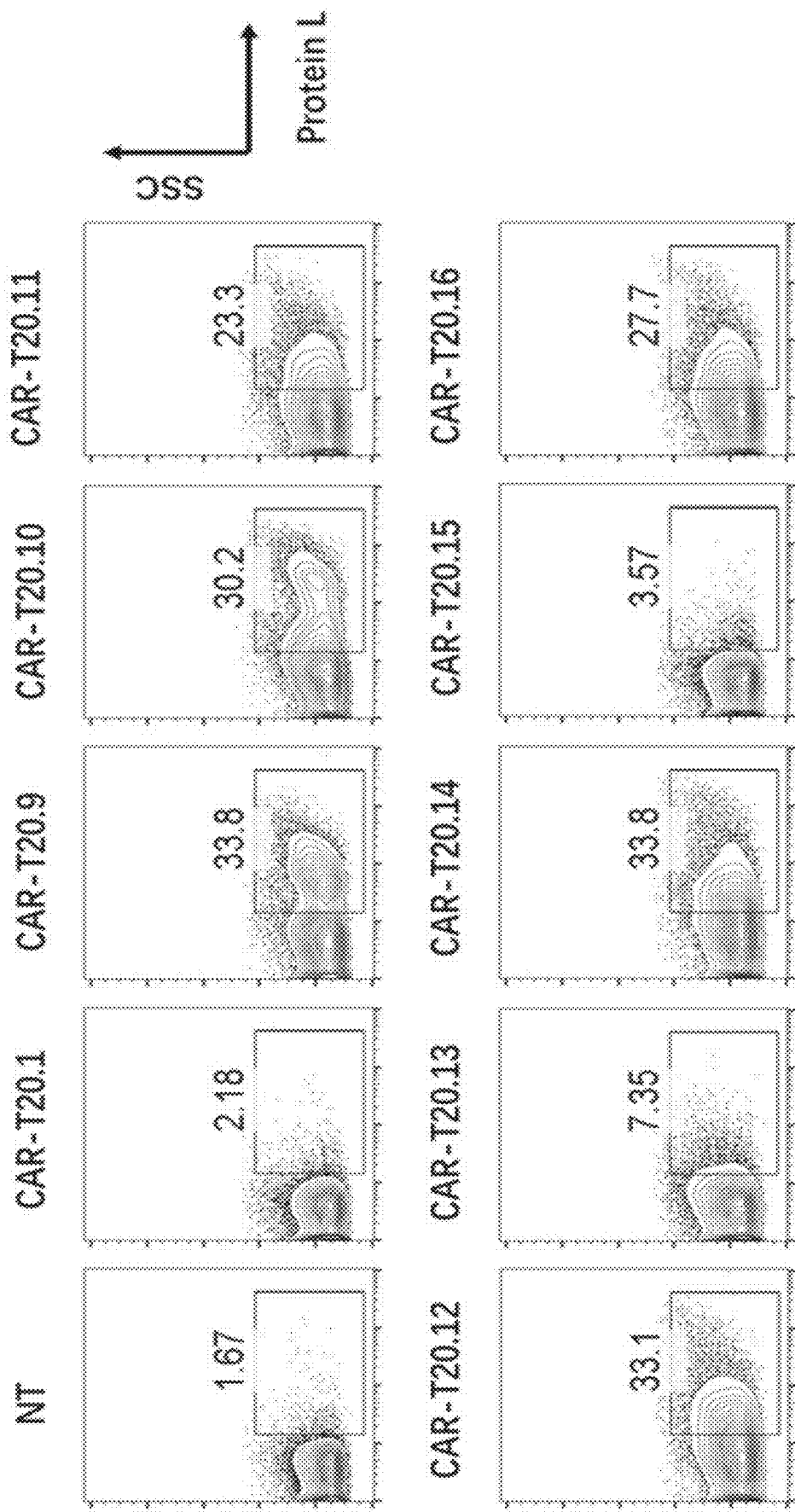
FIGS. 9A-9C show the functional verification results of CAR-T20.11, CAR-T20.12, CAR-T20.13, CAR-T20.14, CAR-T20.15 and CAR-T20.16.

The results are shown in FIG. 9A. Compared with CAR-T20.1, CAR-T20.9 and CAR-T20.10, the positive rates of CAR-T20.11, CAR-T20.12, CAR-T20.14 and CAR-T20.16 were high, while the positive rates of CAR-T20.13 and CAR-T20.15 were very low.

Next, co-culture was performed, and CAR-T20s cells cultured for 7 days were used to detect the indicator proteins CD137 and IFNγ of the cell activation level. $1 \times 10^6$ of CAR-T20s cells cultured for 7 days were cultured respectively with CD20-positive cells Raji, Ramos and negative cells K562, Molt-4 tumor cell line for 18 h with a ratio of 1:1. Then the expression level of CD137 on the surface of T cell membrane and the secretion level of IFNγ in the culture supernatant were detected respectively.

Figure 9B:
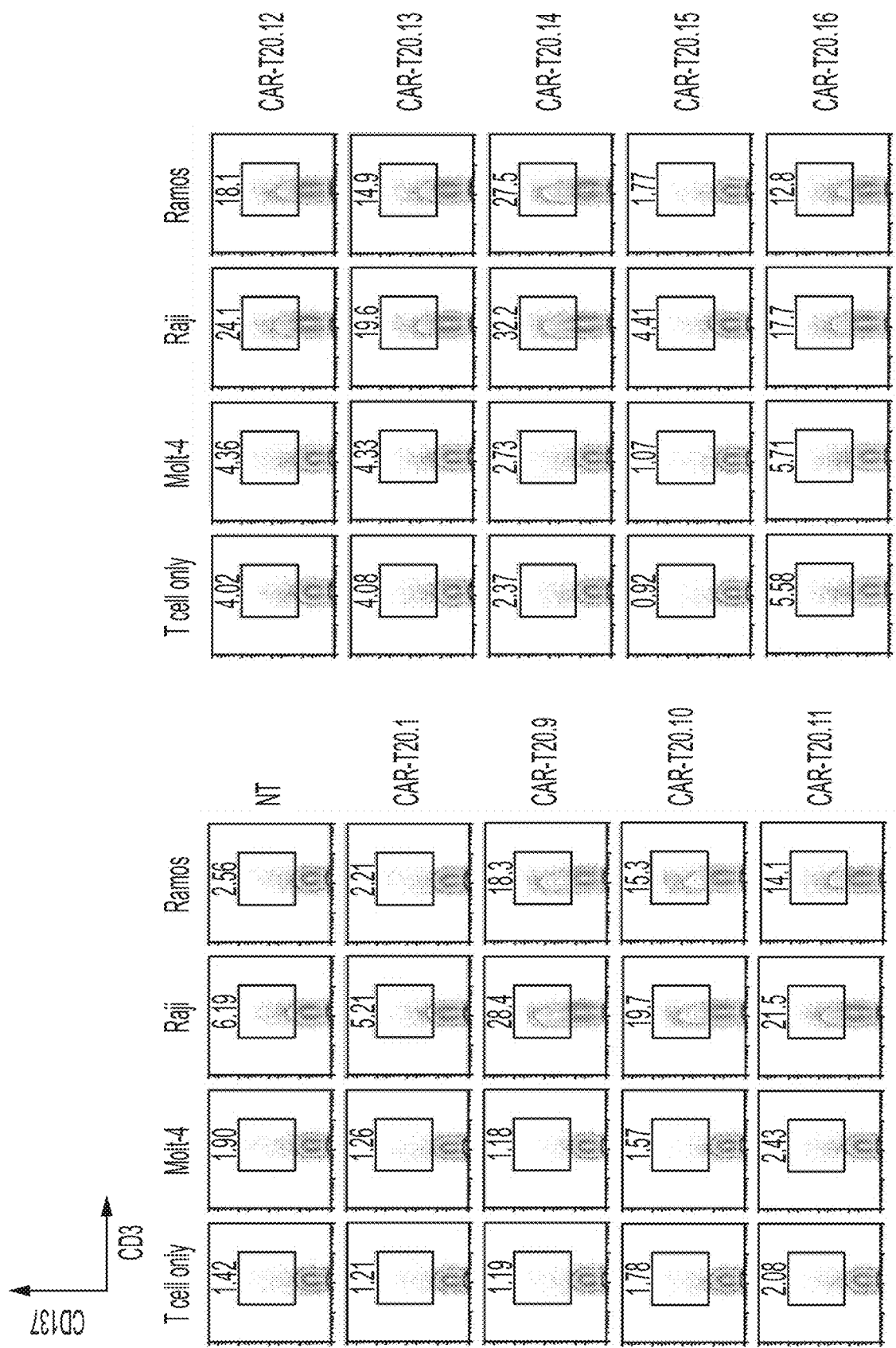
Figure 9C:
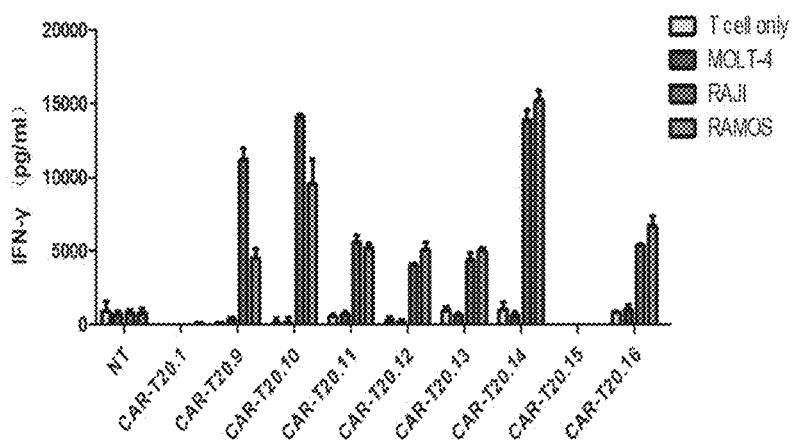

The results are shown in FIGS. 9B and 9C. The results show that after co-culture with CD20-positive Raji and Ramos, the expression levels of CD137 on the surface of T cell membranes in CAR-T20.9, CAR-T20.10, CAR-T20.11, CAR-T20.12, CAR-T20.13, CAR-T20.14 and CAR-T20.16 were activated, and the releases were high, wherein CAR-T20.10 and CAR-T20.14 were the highest, followed by the rest, only CAR-T20.15 showed no response. Correspondingly, the releases of IFNγ in the culture supernatant were the same. The results showed that CAR-T20.10 and CAR-T20.14 had the best activity in this screening.

Example 11 Screening and Functional Verification of CAR-T20.17, CAR-T20.18 and CAR-T20.19

The construction and detection of CART cells were performed with reference to Examples 2, 3, 4, and 5.

First, full-length DNA was synthesized and cloned to achieve the construction of encoding plasmids. CAR-T20.17, CAR-T20.18 and CAR-T20.19 were designed (the structures are shown in Table 1 and the sequences are shown in Table 2), and then the functional verification was performed.

PBMCs were thawed and infected to obtain CAR-T20s cells. Starting from day 6, CAR-T20s cells can be taken for the corresponding activity assay.

$0.5 \times 10^6$ cells of CAR-T20s cell sample cultured for 7 days were taken and detected for the T cell transfection efficiency. Protein L method was used to identify the expression level of CAR gene-encoded protein on the surface of T cell membrane in CAR-T20s cells cultured for 7 days.

Figure 10A:
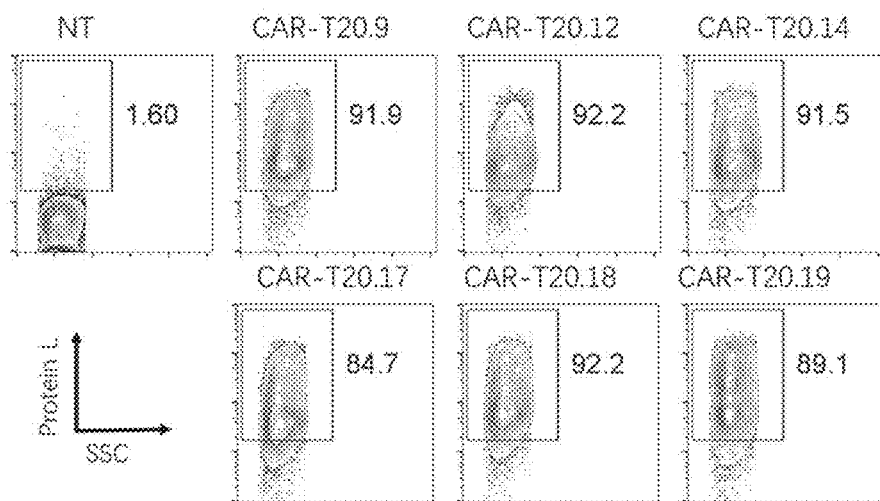
FIGS. 10A-10D show the functional verification results of CAR-T20.17, CAR-T20.18 and CAR-T20.19.

The results are shown in FIG. 10A. Compared with CAR-T20.9, CAR-T20.12 and CAR-T20.14, the positive rates of CAR-T20.17, CAR-T20.18 and CAR-T20.19 were higher, and the expressions thereof were well.

Next, co-culture was performed, and CAR-T20s cells cultured for 7 days were used to detect the indicator proteins CD137 and IFNγ of the cell activation level. $1 \times 10^6$ of CAR-T20s cells cultured for 7 days were cultured respectively with CD20-positive cells Raji, Ramos and negative cells Karpas-620, Molt-4 tumor cell line for 18 h with a ratio of 1:1. Then the expression levels of CD137 on the surface of T cell membrane and the secretion levels of IFNγ in the culture supernatant were detected respectively.

Figure 10B:
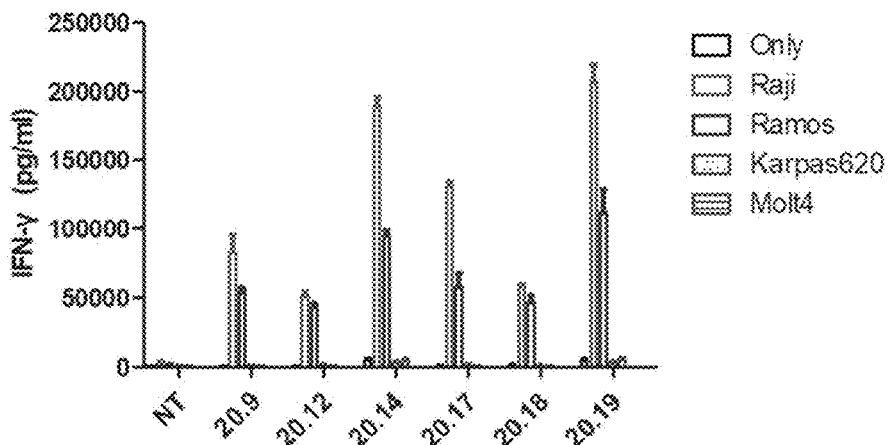
Figure 10C:
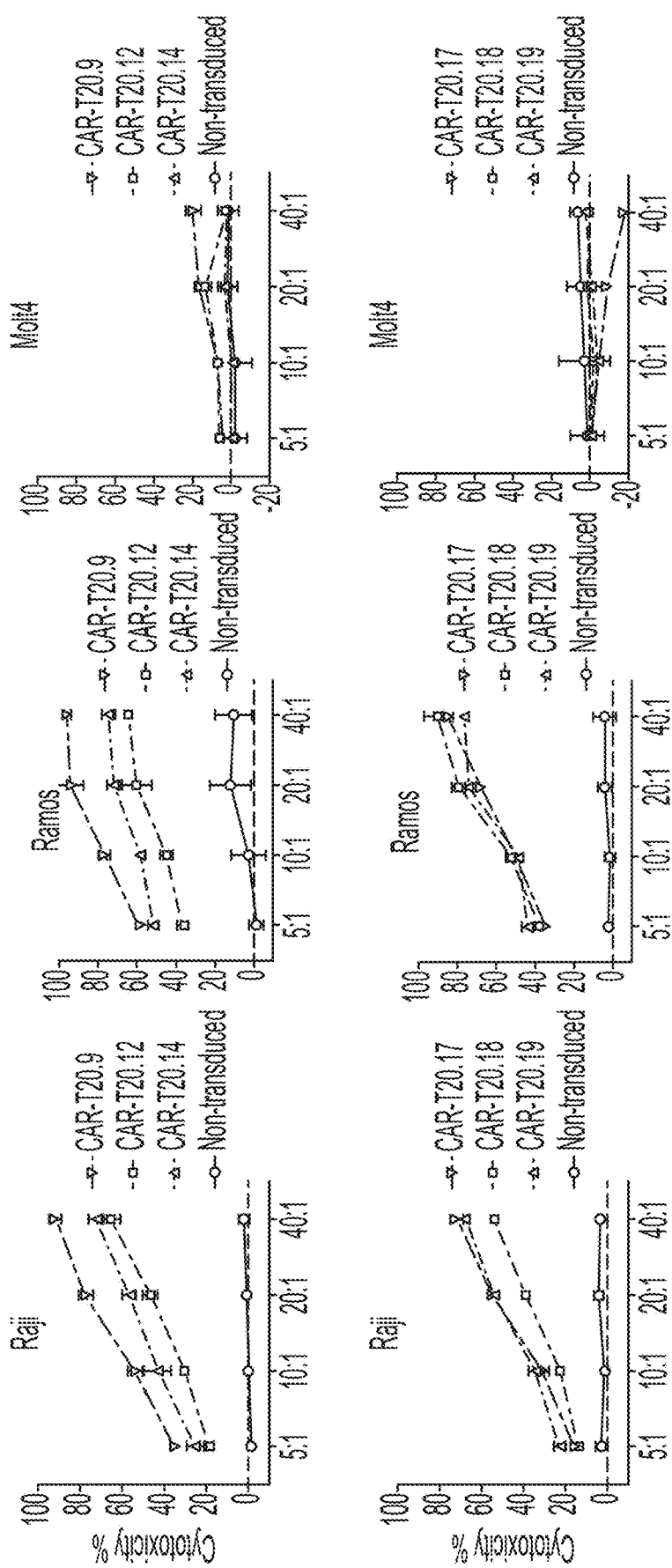
Figure 10D:
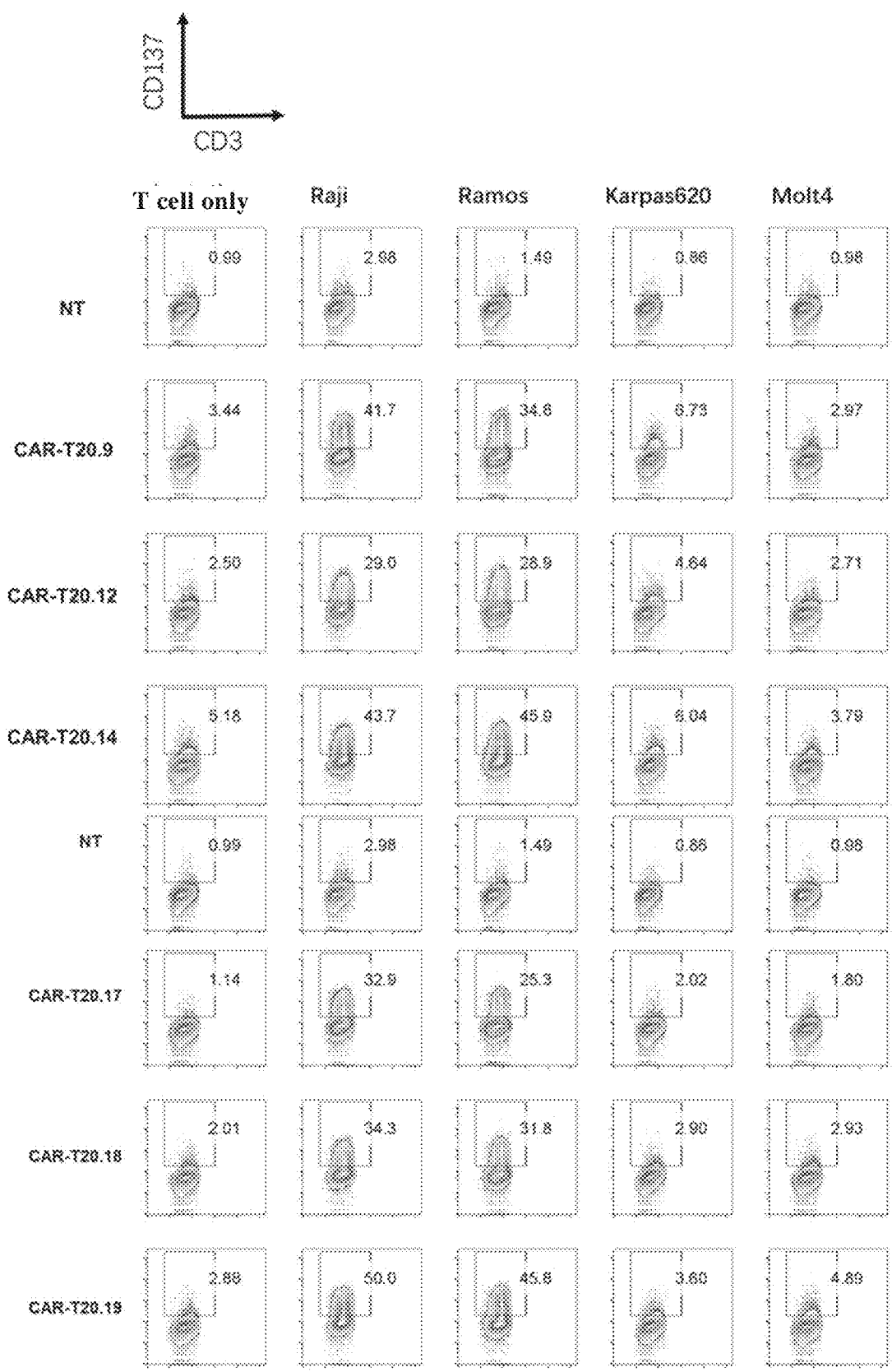

The results are shown in FIGS. 10B and 10D. After co-culture with CD20-positive Raji, Ramos, the expression levels of CD137 on the surface of T cell membrane in CAR-T20.17, CAR-T20.18 and CAR-T20.19 were activated and released very high. Correspondingly, the releases of IFNγ in the culture supernatant were the same, wherein the releases of CAR-T20.17, CAR-T20.18 and CAR-T20.19 were very high. Subsequently, the detection of LDH levels released by CAR-T20s cells for killing targeted tumors in vitro was performed. Specific experimental methods can be referred to Example 5.

Target cells comprise CD20-positive Raji, Romas, and CD20-negative Molt4. The final killing results showed that CAR-T20.17, CAR-T20.18, and CAR-T20.19 had strong killing effects on target cells CD20-positive Raji and Romas.

The results of Examples 8-11 are summarized as follows:

The applicant of the present invention conducted a large number of experiments and screened out multiple CARs with good effects. Through comparison, it was found that 20.1, 20.2, 20.4, 20.5, 20.6, 20.7, 20.8 and 20.15 were basically invalid, and 20.11, 20.12 and 20.13 had certain effects, but the effects of them were less than that of 20.9, 20.10, 20.14, 20.16, 20.17, 20.18 and 20.19, wherein the effects of 20.18 and 20.19 were the best. Based on the above structures, CD20 Scfv and CD19 scFv (FMC63) were tandemly used in a new bispecific chimeric antigen receptor.

The structures of the chimeric antigen receptor in the CART cells involved in Examples 8-11 are shown in Table 1 below, and the sequences are shown in Table 2 below.

TABLE 1

Chimeric antigen receptors and structures thereof

| Change of CAR-T | Structure |
|---|---|
| CAR-T20.1 | [CD8LS]- CD20(AY16076.1) [VL-Linker-VH]-[hinge-CD8DE]-[4-1BB]-[CD3zeta] |
| CAR-T20.5 | [CD8LS]- CD20(AY16076.1) [VL-Linker-VH]-[hinge-CD8TM]-[4-1BB]-[CD3zeta] |
| CAR-T20.6 | [CD8LS]- CD20(AY16076.1) [VH-Linker-VL]-[hinge-CD8TM]-[4-1BB]-[CD3zeta] |
| CAR-T20.7 | [CD8LS]- CD20(IDEC-C2B8) [VL-Linker-VH]-[hinge-CD8TM]-[4-1BB]-[CD3zeta] |
| CAR-T20.8 | [CD8LS]- CD20(IDEC-C2B8) [VL-Linker-VH]-[hinge-CD8TM]-[4-1BB]-[CD3zeta] |
| CAR-T20.9 | [CD8LS]- LEU16[VH-Linker-VL]-[hinge-CH2-CH3-CD28TM] -[CD28] -[4-1BB]-[CD3zeta] |
| CAR-T20.10 | [CD8LS]- LEU16[VL-Linker-VH]-[hinge-CH2-CH3-CD28TM] -[CD28] -[4-1BB]-[CD3zeta] |
| CAR-T20.11 | [CD8LS]- LEU16[VL-Linker-VH]-[hinge-CH2-CH3-CD8TM]-[4-1BB]-[CD3zeta] |
| CAR-T20.12 | [CD8LS]- LEU16[VH-Linker-VL]-[hinge-CH2-CH3-CD8TM] -[4-1BB]-[CD3zeta] |
| CAR-T20.13 | [CD8LS]- Obinutuzumab[VH-Linker-VL]-[hinge-CH2-CH3-CD8TM] -[4-1BB]-[CD3zeta] |
| CAR-T20.14 | [CD8LS]- Ofatuzumab[VH-Linker-VL]-[hinge-CH2-CH3-CD8TM] -[4-1BB]-[CD3zeta] |
| CAR-T20.15 | [CD8LS]- CD20(AY16076.1)[VH-Linker-VL]-[hinge-CH2-CH3-CD8TM] -[4-1BB]-[CD3zeta] |

TABLE 1-continued

Chimeric antigen receptors and structures thereof

| Change of CAR-T | Structure |
|---|---|
| CAR-T20.16 | [CD8LS]- Rituximab[VH-Linker-VL]-[hinge-CH2-CH3-CD8TM] -[4-1BB]-[CD3zeta] |
| CAR-T20.17 | [CD8LS]- LEU16[VH-Linker-VL]-[hinge-CH2-CH3-CD28TM] -[CD28] -[4-1BB]-[CD3zeta](L235E N297Q) |
| CAR-T20.18 | [CD8LS]- LEU16[VH-Linker-VL]-[hinge-CH2-CH3-CD8TM]-[4-1BB]-[CD3zeta](L235E N297Q) |
| CAR-T20.19 | [CD8LS]- Ofatuzumab[VH-Linker-VL]-[hinge-CH2-CH3-CD8TM] -[4-1BB]-[CD3zeta](L235E N297Q) |

TABLE 2

Chimeric antigen receptors and sequences thereof

| CAR-T | Sequence | SEQ ID NO. |
|---|---|---|
| CAR-T20.1 | MDIQLTQSPAILSASPGEKVTMTCRASSSLSFMHWYQQKPGS SPKPWIYATSNLASGVPARFSGSGSGTSYSLTISTVEAEDAAS YFCHQWSSNPLTFGAGTKLEISSGGGGSGGGGSGDVMGVDS GGGLVQPGGSRKLSCAAPGFTFSSFGMHWVRQAPEKGLEW VAYISSPSSTLHYADRVKGRFTISRDNPKNTLFLQMKLPSLCY GLLGPRDHVRLLKTRLSNSIMYFSHFVPVFLPAKPTTTPAPR PPTPAPTIASQPLSLRPEACRPAAGGAVHTRGLDFACDIYIWA PLAGTCGVLLLSLVITLYCRSKRGRKKLLYIFKQPFMRPVQTT QEEDGCSCRFPEEEEGGCELEFRVKFSRSADAPAYQQGQNQL YNELNLGRREEYDVLDKRRGRDPEMGGKPRRKNPQEGLYN ELQKDKMAEAYSEIGMKGERRRGKGHDGLYQGLSTATKDT YDALHMQALPPR | 23 |
| CAR-T20.4 | MALPVTALLLPLALLLHAARPDIQLTQSPAILSASPGEKVTMT CRASSSLSFMHWYQQKPGSSPKPWIYATSNLASGVPARFSGS GSGTSYSLTISTVEAEDAASYFCHQWSSNPLTFGAGTKLEISS GGGGSGGGGSGDVMGVDSGGGLVQPGGSRKLSCAAPGFTF SSFGMHWVRQAPEKGLEWVAYISSPSSTLHYADRVKGRFTIS RDNPKNTLFLQMKLPSLCYGLLGPRDHVRLLKTRLSNSIMY FSHFVPVFLPAKPTTTPAPRPPTPAPTIASQPLSLRPEACRPAA GGAVHTRGLDFACDIYIWAPLAGTCGVLLLSLVITLYCRSKR GRKKLLYIFKQPFMRPVQTTQEEDGCSCRFPEEEEGGCELEF RVKFSRSADAPAYQQGQNQLYNELNLGRREEYDVLDKRRG RDPEMGGKPRRKNPQEGLYNELQKDKMAEAYSEIGMKGER RRGKGHDGLYQGLSTATKDTYDALHMQALPPR | 24 |
| CAR-T20.5 | MALPVTALLLPLALLLHAARPDIQLTQSPAILSASPGEKVTMT CRASSSLSFMHWYQQKPGSSPKPWIYATSNLASGVPARFSGS GSGTSYSLTISTVEAEDAASYFCHQWSSNPLTFGAGTKLEIGG GGSGGGGSGGGGSDVMGVDSGGGLVQPGGSRKLSCAAPGF TFSSFGMHWVRQAPEKGLEWVAYISSPSSTLHYADRVKGRF TISRDNPKNTLFLQMKLPSLCYGLLGPRDHVRLLTRTTTPA PRPPTPAPTIASQPLSLRPEACRPAAGGAVHTRGLDFACDIYI WAPLAGTCGVLLLSLVITLYCRSKRGRKKLLYIFKQPFMRPV QTTQEEDGCSCRFPEEEEGGCELEFELGTFKTNDLQGSCRS | 25 |
| CAR-T20.6 | MALPVTALLLPLALLLHAARPDVMGVDSGGGLVQPGGSRKL SCAAPGFTFSSFGMHWVRQAPEKGLEWVAYISSPSSTLHYAD RVKGRFTISRDNPKNTLFLQMKLPSLCYGLLGPRDHVRLLG GGGSGGGGSGGGGSDIQLTQSPAILSASPGEKVTMTCRASSS LSFMHWYQQKPGSSPKPWIYATSNLASGVPARFSGSGSGTSY SLTISTVEAEDAASYFCHQWSSNPLTFGAGTKLEITRTTTPAP RPPTPAPTIASQPLSLRPEACRPAAGGAVHTRGLDFACDIYIW APLAGTCGVLLLSLVITLYCRSKRGRKKLLYIFKQPFMRPVQ TTQEEDGCSCRFPEEEEGGCELEFELGTFKTNDLQGSCRS | 26 |
| CAR-T20.7 | MALPVTALLLPLALLLHAARPQIVLSQSPAILSASPGEKVTMT CRASSSVSYIHWFQQKPGSSPKPWIYATSNLASGVPRFSGS GSGTSYSLTISRVEAEDAATYYCQQWTSNPPTFGGGTKLEIK GGGGSGGGGSGGGGSQVQLQQPGAELVKPGASVKMSCKAS GYTFTSYNMHWVKQTPGRGLEWIGAIYPGNGDTSYNQKFK GKATLTADKSSSTAYMQLSSLTSEDSAVYYCARSTYYGGDW YFNVWGAGTTVTVSATRTTTPAPRPPTPAPTIASQPLSLRPEA CRPAAGGAVHTRGLDFACDIYIWAPLAGTCGVLLLSLVITLY CRSKRGRKKLLYIFKQPFMRPVQTTQEEDGCSCRFPEEEEGG CELEFELGTFKTNDLQGSCRS | 27 |

TABLE 2-continued

Chimeric antigen receptors and sequences thereof

| CAR-T | Sequence | SEQ ID NO. |
|---|---|---|
| CAR-T20.8 | MALPVTALLLPLALLLHAARPQVQLQQPGAELVKPGASVKM SCKASGYTFTSYNMHWVKQTPGRGLEWIGAIYPGNGDTSYN QKFKGKATLTADKSSSTAYMQLSSLTSEDSAVYYCARSTYY GGDWYFNVWGAGTTVTVSAGGGGSGGGGSGGGGSQIVLSQ SPAILSASPGEKVTMTCRASSSVSYIHWFQQKPGSSPKPWIYA TSNLASGVPVRFSGSGSGTSYSLTISRVEAEDAATYYCQQWT SNPPTFGGGTKLEIKTRTTTPAPRPPTPAPTIASQPLSLRPEAC RPAAGGAVHTRGLDFACDIYIWAPLAGTCGVLLLSLVITLYC RSKRGRKKLLYIFKQPFMRPVQTTQEEDGCSCRFPEEEEGGC ELEFELGTFKTNDLQGSCRS | 28 |
| CAR-T20.9 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFLGGPSVFLFPPK PKDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKFWVLV VVGGVLACYSLLVTVAFIIFWVRSKRSRLLHSDYMNMTPRR PGPTRKHYQPYAPPRDFAAYRSKRGRKKLLYIFKQPFMRPVQ TTQEEDGCSCRFPEEEEGGCELRVKFSRSADAPAYKQGQNQL YNELNLGRREEYDVLDKRRGRDPEMGGKPRRKNPQEGLYN ELQKDKMAEAYSEIGMKGERRRGKGHDGLYQGLSTATKDT YDALHMQALPPR | 29 |
| CAR-T20.10 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFLGGPSVFLFPPK PKDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKFWVLV VVGGVLACYSLLVTVAFIIFWVRSKRSRLLHSDYMNMTPRR PGPTRKHYQPYAPPRDFAAYRSKRGRKKLLYIFKQPFMRPVQ TTQEEDGCSCRFPEEEEGGCELRVKFSRSADAPAYKQGQNQL YNELNLGRREEYDVLDKRRGRDPEMGGKPRRKNPQEGLYN ELQKDKMAEAYSEIGMKGERRRGKGHDGLYQGLSTATKDT YDALHMQALPPR | 30 |
| CAR-T20.11 | MALPVTALLLPLALLLHAARPDIVLTQSPAILSASPGEKVTMT CRASSSVNYMDWYQKKPGSSPKPWIYATSNLASGVPARFSG SGSGTSYSLTISRVEAEDAATYYCQQWSFNPPTFGGGTKLEIK GGGGSGGGGSGGGGSEVQLQQSGAELVKPGASVKMSCKAS GYTFTSYNMHWVKQTPGQGLEWIGAIYPGNGDTSYNQKFK GKATLTADKSSSTAYMQLSSLTSEDSADYYCARSNYYGSSY WFFDVWGAGTTVTVSSESKYGPPCPPCPAPEFLGGPSVFLFPP KPKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLGKIYIWA PLAGTCGVLLLSLVITLYCKRGRKKLLYIFKQPFMRPVQTTQ EEDGCSCRFPEEEEGGCELRVKFSRSADAPAYKQGQNQLYN ELNLGRREEYDVLDKRRGRDPEMGGKPRRKNPQEGLYNEL QKDKMAEAYSEIGMKGERRRGKGHDGLYQGLSTATKDTYD ALHMQALPPR | 31 |
| CAR-T20.12 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW | 32 |

TABLE 2-continued

Chimeric antigen receptors and sequences thereof

| CAR-T | Sequence | SEQ ID NO. |
|---|---|---|
| | SFNPPTFGGGTKLEIKESKYGPPCPPCPAPEFLGGPSVFLFPPK PKDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKIYIWAP LAGTCGVLLLSLVITLYCKRGRKKLLYIFKQPFMRPVQTTQE EDGCSCRFPEEEEGGCELRVKFSRSADAPAYKQGQNQLYNE LNLGRREEYDVLDKRRGRDPEMGGKPRRKNPQEGLYNELQ KDKMAEAYSEIGMKGERRRGKGHDGLYQGLSTATKDTYDA LHMQALPPR | |
| CAR-T20.13 | MALPVTALLLPLALLLHAARPQVQLVQSGAEVKKPGSSVKV SCKASGYAFSYSWINWVRQAPGQGLEWMGRIFPGDGDTDY NGKFKGRVTITADKSTSTAYMELSSLRSEDTAVYYCARNVF DGYWLVYWGQGTLVTVSSGGGGSGGGGSGGGGSDIVMTQT PLSLPVTPGEPASISCRSSKSLLHSNGITYLYWYLQKPGQSPQ LLIYQMSNLVSGVPDRFSGSGSGTDFTLKISRVEAEDVGVYY CAQNLELPYTFGGGTKVEIKRTVESKYGPPCPPCPAPEFLGGP SVFLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTKNQ VSLTCLVKGFYPSDIAVEWESNGQPENNYKTTPPVLDSDGSF FLYSRLTVDKSRWQEGNVFSCSVMHEALHNHYTQKSLSLSL GKIYIWAPLAGTCGVLLLSLVITLYCKRGRKKLLYIFKQPFM RPVQTTQEEDGCSCRFPEEEEGGCELRVKFSRSADAPAYKQG QNQLYNELNLGRREEYDVLDKRRGRDPEMGGKPRRKNPQE GLYNELQKDKMAEAYSEIGMKGERRRGKGHDGLYQGLSTA TKDTYDALHMQALPPR | 33 |
| CAR-T20.14 | MALPVTALLLPLALLLHAARPEVQLVESGGGLVQPGRSLRLS CAASGFTFNDYAMHWVRQAPGKGLEWVSTISWNSGSIGYA DSVKGRFTISRDNAKKSLYLQMNSLRAEDTALYYCAKDIQY GNYYYGMDVWGQGTTVTVSSGGGGSGGGGSGGGGSEIVLT QSPATLSLSPGERATLSCRASQSVSSYLAWYQQKPGQAPRLL IYDASNRATGIPARFSGSGSGTDFTLTISSLEPEDFAVYYCQQ RSNWPITFGQGTRLEIKESKYGPPCPPCPAPEFLGGPSVFLFPP KPKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLGKIYIWA PLAGTCGVLLLSLVITLYCKRGRKKLLYIFKQPFMRPVQTTQ EEDGCSCRFPEEEEGGCELRVKFSRSADAPAYKQGQNQLYN ELNLGRREEYDVLDKRRGRDPEMGGKPRRKNPQEGLYNEL QKDKMAEAYSEIGMKGERRRGKGHDGLYQGLSTATKDTYD ALHMQALPPR | 34 |
| CAR-T20.15 | MALPVTALLLPLALLLHAARPGDVMGVDSGGGLVQPGGSR KLSCAAPGFTFSSFGMHWVRQAPEKGLEWVAYISSPSSTLHY ADRVKGRFTISRDNPKNTLFLQMKLPSLCYGLLGPRDHVRRL LKGGGGSGGGGSGGGGSDIQLTQSPAILSASPGEKVTMTCRA SSSLSFMHWYQQKPGSSPKPWIYATSNLASGVPARFSGSGSG TSYSLTISTVEAEDAASYFCHQWSSNPLTFGAGTKLEIESKYG PPCPPCPAPEFLGGPSVFLFPPKPKDTLMISRTPEVTCVVVDVS QEDPEVQFNWYVDGVEVHNAKTKPREEQFNSTYRVVSVLT VLHQDWLNGKEYKCKVSNKGLPSSIEKTISKAKGQPREPQV YTLPPSQEEMTKNQVSLTCLVKGFYPSDIAVEWESNGQPENN YKTTPPVLDSDGSFFLYSRLTVDKSRWQEGNVFSCSVMHEA LHNHYTQKSLSLSLGKIYIWAPLAGTCGVLLLSLVITLYCKR GRKKLLYIFKQPFMRPVQTTQEEDGCSCRFPEEEEGGCELRV KFSRSADAPAYKQGQNQLYNELNLGRREEYDVLDKRRGRD PEMGGKPRRKNPQEGLYNELQKDKMAEAYSEIGMKGERRR GKGHDGLYQGLSTATKDTYDALHMQALPPR | 35 |
| CAR-T20.16 | MALPVTALLLPLALLLHAARPQVQLQQPGAELVKPGASVKM SCKASGYTFTSYNMHWVKQTPGRGLEWIGAIYPGNGDTSYN QKFKGKATLTADKSSSTAYMQLSSLTSEDSAVYYCARSTYY GGDWYFNVWGAGTTVTVSAGGGGSGGGGSGGGGSQIVLSQ SPAILSASPGEKVTMTCRASSSVSYIHWFQQKPGSSPKPWIYA TSNLASGVPVRFSGSGSGTSYSLTISRVEAEDAATYYCQQWT SNPPTFGGGTKLEIKESKYGPPCPPCPAPEFLGGPSVFLFPPKP KDTLMISRTPEVTCVVVDVSQEDPEVQFNWYVDGVEVHNA KTKPREEQFNSTYRVVSVLTVLHQDWLNGKEYKCKVSNKG | 36 |

TABLE 2-continued

Chimeric antigen receptors and sequences thereof

| CAR-T | Sequence | SEQ ID NO. |
|---|---|---|
| | LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKIYIWAP LAGTCGVLLLSLVITLYCKRGRKKLLYIFKQPFMRPVQTTQE EDGCSCRFPEEEEGGCELRVKFSRSADAPAYKQGQNQLYNE LNLGRREEYDVLDKRRGRDPEMGGKPRRKNPQEGLYNELQ KDKMAEAYSEIGMKGERRRGKGHDGLYQGLSTATKDTYDA LHMQALPPR | |
| CAR-T20.17 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFEGGPSVFLFPPK PKDTLMISRTPEVTCVVVDVSQEDPEVQFNWYVDGVEVHNA KTKPREEQFQSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKFWVLV VVGGVLACYSLLVTVAFIIFWVRSKRSRLLHSDYMNMTPRR PGPTRKHYQPYAPPRDFAAYRSKRGRKKLLYIFKQPFMRPVQ TTQEEDGCSCRFPEEEEGGCELRVKFSRSADAPAYKQGQNQL YNELNLGRREEYDVLDKRRGRDPEMGGKPRRKNPQEGLYN ELQKDKMAEAYSEIGMKGERRRGKGHDGLYQGLSTATKDT YDALHMQALPPR | 37 |
| CAR-T20.18 | MALPVTALLLPLALLLHAARPEVQLQQSGAELVKPGASVKM SCKASGYTFTSYNMHWVKQTPGQGLEWIGAIYPGNGDTSYN QKFKGKATLTADKSSSTAYMQLSSLTSEDSADYYCARSNYY GSSYWFFDVWGAGTTVTVSSGGGGSGGGGSGGGGSDIVLTQ SPAILSASPGEKVTMTCRASSSVNYMDWYQKKPGSSPKPWIY ATSNLASGVPARFSGSGSGTSYSLTISRVEAEDAATYYCQQW SFNPPTFGGGTKLEIKESKYGPPCPPCPAPEFEGGPSVFLFPPK PKDTLMISRTPEVTCVVVDVSQEDPEVQFNWYVDGVEVHNA KTKPREEQFQSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGKIYIWAP LAGTCGVLLLSLVITLYCKRGRKKLLYIFKQPFMRPVQTTQE EDGCSCRFPEEEEGGCELRVKFSRSADAPAYKQGQNQLYNE LNLGRREEYDVLDKRRGRDPEMGGKPRRKNPQEGLYNELQ KDKMAEAYSEIGMKGERRRGKGHDGLYQGLSTATKDTY | 38 |
| CAR-T20.19 | MALPVTALLLPLALLLHAARPEVQLVESGGGLVQPGRSLRLS CAASGFTFNDYAMHWVRQAPGKGLEWVSTISWNSGSIGYA DSVKGRFTISRDNAKKSLYLQMNSLRAEDTALYYCAKDIQY GNYYYGMDVWGQGTTVTVSSGGGGSGGGGSGGGGSEIVLT QSPATLSLSPGERATLSCRASQSVSSYLAWYQQKPGQAPRLL IYDASNRATGIPARFSGSGSGTDFTLTISSLEPEDFAVYYCQQ RSNWPITFGQGTRLEIKESKYGPPCPPCPAPEFEGGPSVFLFPP KPKDTLMISRTPEVTCVVVDVSQEDPEVQFNWYVDGVEVHN AKTKPREEQFQSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLGKIYIWA PLAGTCGVLLLSLVITLYCKRGRKKLLYIFKQPFMRPVQTTQ EEDGCSCRFPEEEEGGCELRVKFSRSADAPAYKQGQNQLYN ELNLGRREEYDVLDKRRGRDPEMGGKPRRKNPQEGLYNEL QKDKMAEAYSEIGMKGERRRGKGHDGLYQGLSTATKDTYD ALHMQALPPR | 39 |

Example 12 In Vivo Experiments in Mice of CART-TN-OF-19 and CART-TN-LEU-19

The inhibitory effects of CART-TN-OF-19 and CART-TN-LEU-19 cells on transplanted tumor cells in mice was tested. The detection method was performed with reference to Example 7, and the control group was NT.

Figure 11:
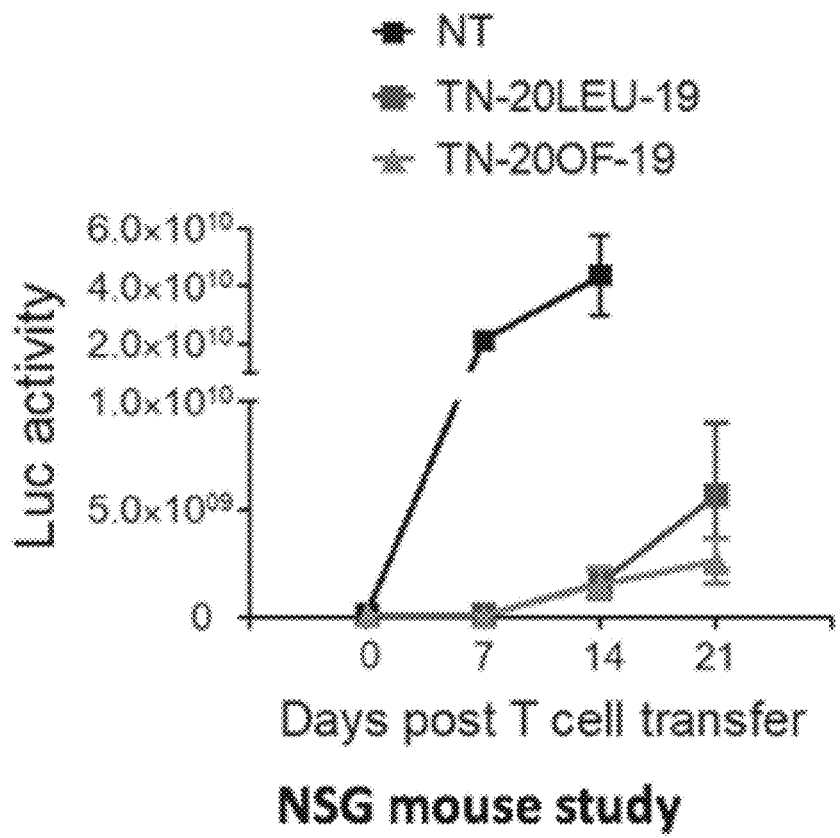
FIG. 11 shows the inhibitory effect of CAR-T19/20s cells on transplanted tumor cells in mice.

The results are shown in FIG. 11. Both CART cells can inhibit tumor cell expansion well. The fluorescence intensities of mice in the CART cell groups were very weak, while that of the NT group was very strong. Wherein, CART-TN-OF-19 can inhibit or kill tumor cells better than CART-TN-LEU-19 in vivo.

Example 13 Phase I Clinical Trial of CART-TN-OF-19

After approval by the ethics committee, a total of 3 volunteers (numbers C001, C002, and C003) were conducted in Phase I clinical trials. The key criteria for volunteer selection are as follows: the age should be 18-75 years, having received more than 2 DLBCL treatment, PD after or ineligible for auto-SCT, having not received anti-CD19 therapy, having no active CNS, and having sufficient liver, kidney, heart, and hematopoietic functions.

Figure 12:
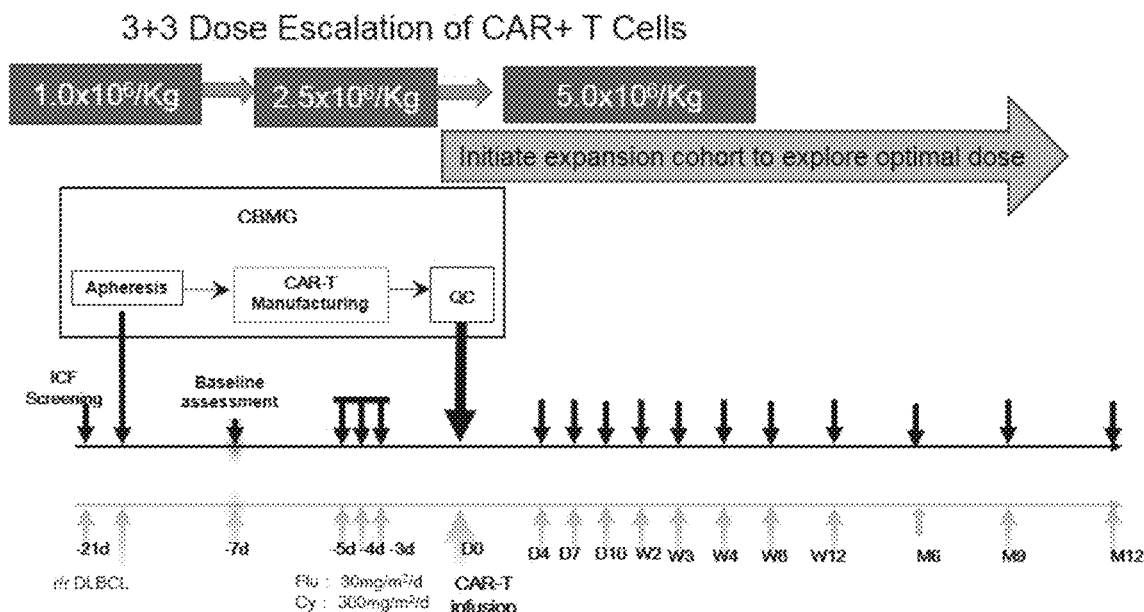
FIG. 12 shows the experimental process of the phase I clinical trial of CART-TN-20OF-19.

The experimental process is shown in FIG. 12.

The clinical responses of each subject is shown in Table 3. The results showed that the objective response rate (ORR) was 100%. After 4 weeks of treatment, all three patients achieved partial remission (PR). 1 patient achieved complete remission (CR) at 8 w, and 2 patients achieved CR at 3 m, and the clinical response is ongoing.

TABLE 3

Clinical responses of experimental subjects

| | Parameter Shanghai Tongji Hospital Patient | | | | | |
|---|---|---|---|---|---|---|
| | C001 | | C003 | | C004 | |
| | Infusion time | | | | | |
| | Nov. 20, 2019 | | Dec. 20, 2019 | | Dec. 30, 2019 | |
| | Response | SPD | Response | SPD | Response | SPD |
| Baseline | | 2203.12 | | 1751.13 | | 4956.14 |
| 4 w | PR(CT) | 862.86 (60.8%) | PR(CT) | 796.77 (54.5%) | PR(CT) | 1645.45 (66.8%) |
| 8 w | CR(CT) | 211.32 (90.4%) All LDi ≤1.5 cm | NE* | | PR(CT) | 1501.39 (69.7%) |
| 12 w | NE* | | CR(PET/CT) | | CR(PET/CT) | |
| 15 w | CR(PET/CT) | | | | | |

*NE because of COVID-19

The adverse events that occurred after treatment are shown in Table 4. The patients generally well tolerated safety profile. One of the three patients had a grade 2 cytokine release syndrome, and two had a grade 1 cytokine release syndrome. There were no death reported, no CRES reported. Cytopenia mostly related to Cy/Flu lymphodepletion.

It needs to be explained that the occurrence of a certain degree of cytokine release syndrome after treatment also shows the effectiveness of CART treatment from the side, and no particularly serious cytokine release syndrome occurred in 3 patients. CART-TN-OF-19 has better security.

TABLE 4

Adverse reactions of subjects after treatment

| Parameter | C001 | C003 | C004 |
|---|---|---|---|
| Cytokine release syndrome | Grade 2 | Grade 1 | Grade 1 |
| Neurotoxicity | No | No | No |
| Neutropenia | Grade 4 | Grade 3 | Grade 2 |
| Thrombocytopenia | No | No | No |
| Anemia | Grade 3 | No | No |

Figure 13:
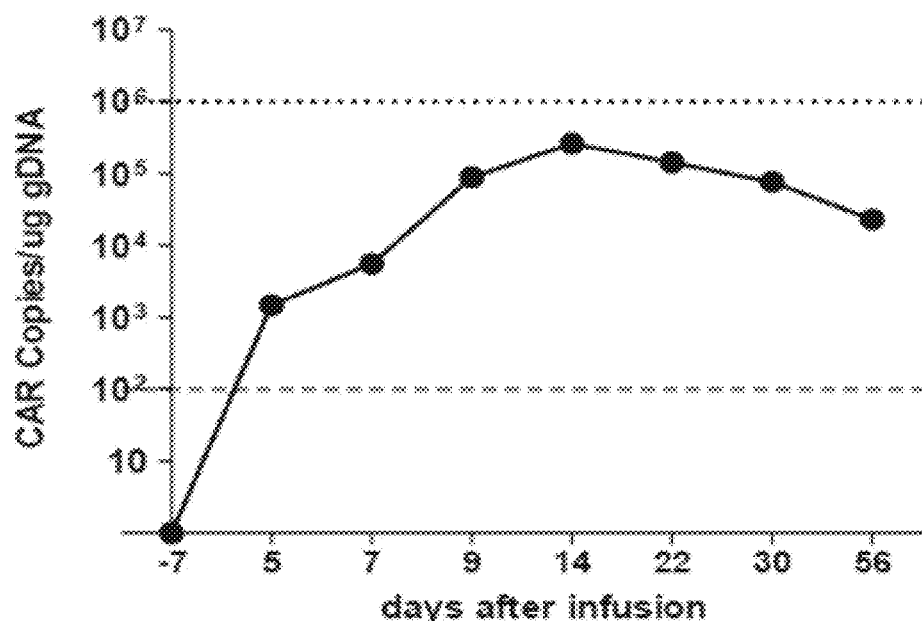
FIG. 13 shows the detection results of the CAR copy number.

The results of the CAR copy number test are shown in FIG. 13, which shows that the CAR copy number reached its peak (higher than $10^5$ copies/microgram gDNA) in 14 days, and there was still a very high copy number after 56 days.

Figure 14:
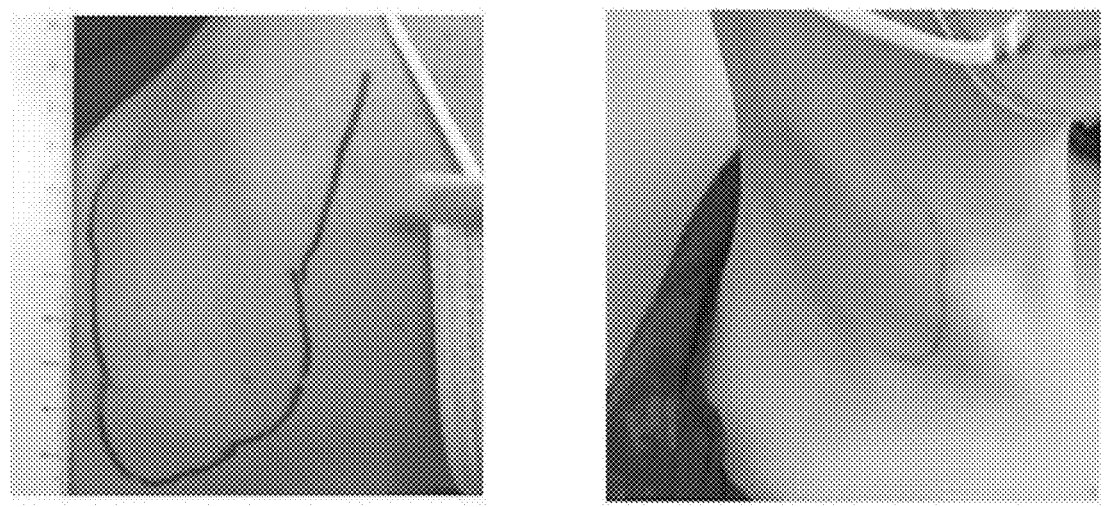
FIG. 14 shows the change in tumor size of a subject.

The change in tumor size of an experimental subject is shown in FIG. 14, which shows that the tumor volume decreased significantly and almost disappeared after 4 weeks of treatment.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A bispecific chimeric antigen receptor (CAR), comprising an amino acid sequence set forth in SEQ ID NO: 16, wherein the bispecific CAR comprises an anti-CD20 antigen-binding region and an anti-CD19 antigen-binding region.

2. An immune cell comprising a bispecific chimeric antigen receptor (CAR), wherein the bispecific CAR comprises an amino acid sequence set forth in SEQ ID NO: 16, and wherein the bispecific CAR comprises an anti-CD20 antigen-binding region and an anti-CD19 antigen-binding region. .

3. The immune cell of claim 2, wherein the immune cell is a T cell or a natural killer (NK) cell.

4. A pharmaceutical composition comprising an immune cell which comprises a bispecific chimeric antigen receptor (CAR), wherein the bispecific CAR comprises an amino acid sequence set forth in SEQ ID NO: 16, and wherein the bispecific CAR comprises an anti-CD20 antigen-binding region and an anti-CD19 antigen-binding region.

* * * * *

SEQUENCE LISTING

<160> NUMBER OF SEQ ID NOS: 39

<210> SEQ ID NO 1
<211> LENGTH: 122
<212> TYPE: PRT
<213> ORGANISM: Artificial Sequence
<220> FEATURE:
<223> OTHER INFORMATION: synthesized
<220> FEATURE:

```
<221> NAME/KEY: misc_feature
<223> OTHER INFORMATION: Heavy chain sequence of single-chain variable
      region (VH) derived from Leu16 antibody

<400> SEQUENCE: 1

Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser
        115                 120

<210> SEQ ID NO 2
<211> LENGTH: 106
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Light chain sequence of single-chain variable
      region (VL) derived from Leu16 antibody

<400> SEQUENCE: 2

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys
            100                 105

<210> SEQ ID NO 3
<211> LENGTH: 122
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Heavy chain sequence of single-chain variable
      region (VH) derived from Ofatumumab antibody

<400> SEQUENCE: 3
```

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
            115                 120
```

<210> SEQ ID NO 4
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Light chain sequence of single-chain variable
      region (VL) derived from Ofatumumab antibody

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105
```

<210> SEQ ID NO 5
<211> LENGTH: 107
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of the light chain of
      single-chain variable region (VL) derived from FMC63 antibody

<400> SEQUENCE: 5

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30
```

Leu Asn Trp Tyr Gln Gln Lys Pro Asp Gly Thr Val Lys Leu Leu Ile
                35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
                100                 105

<210> SEQ ID NO 6
<211> LENGTH: 120
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of the heavy chain of
      single-chain variable region (VH) derived from FMC63 antibody

<400> SEQUENCE: 6

Glu Val Lys Leu Gln Glu Ser Gly Pro Gly Leu Val Ala Pro Ser Gln
 1               5                  10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
                35                  40                  45

Gly Val Ile Trp Gly Ser Glu Thr Thr Tyr Tyr Asn Ser Ala Leu Lys
 50                  55                  60

Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser
            115                 120

<210> SEQ ID NO 7
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Linker sequences

<400> SEQUENCE: 7

Gly Gly Gly Gly Ser
 1               5

<210> SEQ ID NO 8
<211> LENGTH: 21
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Leader sequence of CD8 antigen -continued

<400> SEQUENCE: 8

Met Ala Leu Pro Val Thr Ala Leu Leu Pro Leu Ala Leu Leu
1               5                   10                  15

His Ala Ala Arg Pro
            20

<210> SEQ ID NO 9
<211> LENGTH: 229
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: IgG4 Hinge-CH2-CH3

<400> SEQUENCE: 9

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 10
<211> LENGTH: 24
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD8 transmembrane region

<400> SEQUENCE: 10

```
Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 11
<211> LENGTH: 27
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: CD28 transmembrane region

<400> SEQUENCE: 11

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 12
<211> LENGTH: 42
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Co-stimulatory factor signal region derived
      from 4-1BB

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 13
<211> LENGTH: 41
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Co-stimulatory factor signal region derived
      from CD28

<400> SEQUENCE: 13

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 14
<211> LENGTH: 113
<212> TYPE: PRT
<213> ORGANISM: Artificial Sequence
<220> FEATURE:
<223> OTHER INFORMATION: synthesized
```

-continued

```
<220> FEATURE:
<221> NAME/KEY: misc_feature
<223> OTHER INFORMATION: Signaling region of CD3

<400> SEQUENCE: 14

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 15
<211> LENGTH: 710
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of TN-LEU-19

<400> SEQUENCE: 15

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Asn Tyr Met Asp Trp Tyr Gln Lys Lys Pro Gly Ser Ser Pro Lys
    50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Gly Gly Thr Lys Leu Glu Ile Lys Gly Ser
        115                 120                 125

Thr Ser Gly Gly Gly Ser Gly Gly Gly Ser Gly Gly Gly Ser Ser
    130                 135                 140

Glu Val Gln Leu Gln Gln Ser Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
```

-continued

```
            195                 200                 205
Lys Gly Lys Ala Thr Leu Thr Ala Asp Lys Ser Ser Thr Ala Tyr
    210                 215                 220

Met Gln Leu Ser Ser Leu Thr Ser Glu Asp Ser Ala Asp Tyr Tyr Cys
225                 230                 235                 240

Ala Arg Ser Asn Tyr Tyr Gly Ser Ser Tyr Trp Phe Phe Asp Val Trp
                245                 250                 255

Gly Ala Gly Thr Thr Val Thr Val Ser Ser Gly Gly Gly Gly Ser Glu
                260                 265                 270

Val Lys Leu Gln Glu Ser Gly Pro Gly Leu Val Ala Pro Ser Gln Ser
    275                 280                 285

Leu Ser Val Thr Cys Thr Val Ser Gly Val Ser Leu Pro Asp Tyr Gly
    290                 295                 300

Val Ser Trp Ile Arg Gln Pro Pro Arg Lys Gly Leu Glu Trp Leu Gly
305                 310                 315                 320

Val Ile Trp Gly Ser Glu Thr Thr Tyr Tyr Asn Ser Ala Leu Lys Ser
                325                 330                 335

Arg Leu Thr Ile Ile Lys Asp Asn Ser Lys Ser Gln Val Phe Leu Lys
                340                 345                 350

Met Asn Ser Leu Gln Thr Asp Asp Thr Ala Ile Tyr Tyr Cys Ala Lys
                355                 360                 365

His Tyr Tyr Tyr Gly Gly Ser Tyr Ala Met Asp Tyr Trp Gly Gln Gly
                370                 375                 380

Thr Ser Val Thr Val Ser Ser Gly Ser Thr Ser Gly Ser Gly Lys Pro
385                 390                 395                 400

Gly Ser Gly Glu Gly Ser Thr Lys Gly Asp Ile Gln Met Thr Gln Thr
                405                 410                 415

Thr Ser Ser Leu Ser Ala Ser Leu Gly Asp Arg Val Thr Ile Ser Cys
                420                 425                 430

Arg Ala Ser Gln Asp Ile Ser Lys Tyr Leu Asn Trp Tyr Gln Gln Lys
                435                 440                 445

Pro Asp Gly Thr Val Lys Leu Leu Ile Tyr His Thr Ser Arg Leu His
    450                 455                 460

Ser Gly Val Pro Ser Arg Phe Ser Gly Ser Gly Ser Gly Thr Asp Tyr
465                 470                 475                 480

Ser Leu Thr Ile Ser Asn Leu Glu Gln Glu Asp Ile Ala Thr Tyr Phe
                485                 490                 495

Cys Gln Gln Gly Asn Thr Leu Pro Tyr Thr Phe Gly Gly Gly Thr Lys
                500                 505                 510

Leu Glu Ile Thr Glu Ser Lys Tyr Gly Pro Pro Cys Pro Pro Cys Pro
    515                 520                 525

Met Phe Trp Val Leu Val Val Val Gly Val Leu Ala Cys Tyr Ser
    530                 535                 540

Leu Leu Val Thr Val Ala Phe Ile Ile Phe Trp Val Lys Arg Gly Arg
545                 550                 555                 560

Lys Lys Leu Leu Tyr Ile Phe Lys Gln Pro Phe Met Arg Pro Val Gln
                565                 570                 575

Thr Thr Gln Glu Glu Asp Gly Cys Ser Cys Arg Phe Pro Glu Glu Glu
                580                 585                 590

Glu Gly Gly Cys Glu Leu Arg Val Lys Phe Ser Arg Ser Ala Asp Ala
                595                 600                 605

Pro Ala Tyr Gln Gln Gly Gln Asn Gln Leu Tyr Asn Glu Leu Asn Leu
    610                 615                 620
```

-continued

```
Gly Arg Arg Glu Glu Tyr Asp Val Leu Asp Lys Arg Gly Arg Asp
625                 630                 635                 640

Pro Glu Met Gly Gly Lys Pro Arg Arg Lys Asn Pro Gln Glu Gly Leu
            645                 650                 655

Tyr Asn Glu Leu Gln Lys Asp Lys Met Ala Glu Ala Tyr Ser Glu Ile
            660                 665                 670

Gly Met Lys Gly Glu Arg Arg Arg Gly Lys Gly His Asp Gly Leu Tyr
            675                 680                 685

Gln Gly Leu Ser Thr Ala Thr Lys Asp Thr Tyr Asp Ala Leu His Met
            690                 695                 700

Gln Ala Leu Pro Pro Arg
705                 710

<210> SEQ ID NO 16
<211> LENGTH: 712
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of TN-OF-19

<400> SEQUENCE: 16

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Ser Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

Ser Asn Trp Pro Ile Thr Phe Gly Gln Gly Thr Arg Leu Glu Ile Lys
        115                 120                 125

Gly Ser Thr Ser Gly Gly Gly Ser Gly Gly Gly Ser Gly Gly Gly Gly
    130                 135                 140

Ser Ser Glu Val Gln Leu Val Glu Ser Gly Gly Gly Leu Val Gln Pro
145                 150                 155                 160

Gly Arg Ser Leu Arg Leu Ser Cys Ala Ala Ser Gly Phe Thr Phe Asn
                165                 170                 175

Asp Tyr Ala Met His Trp Val Arg Gln Ala Pro Gly Lys Gly Leu Glu
            180                 185                 190

Trp Val Ser Thr Ile Ser Trp Asn Ser Gly Ser Ile Gly Tyr Ala Asp
        195                 200                 205

Ser Val Lys Gly Arg Phe Thr Ile Ser Arg Asp Asn Ala Lys Lys Ser
    210                 215                 220

Leu Tyr Leu Gln Met Asn Ser Leu Arg Ala Glu Asp Thr Ala Leu Tyr
225                 230                 235                 240

Tyr Cys Ala Lys Asp Ile Gln Tyr Gly Asn Tyr Tyr Tyr Gly Met Asp
                245                 250                 255
```

```
Val Trp Gly Gln Gly Thr Thr Val Thr Val Ser Ser Gly Gly Gly
            260                 265                 270

Ser Glu Val Lys Leu Gln Glu Ser Gly Pro Gly Leu Val Ala Pro Ser
            275                 280                 285

Gln Ser Leu Ser Val Thr Cys Thr Val Ser Gly Val Ser Leu Pro Asp
            290                 295                 300

Tyr Gly Val Ser Trp Ile Arg Gln Pro Pro Arg Lys Gly Leu Glu Trp
305                 310                 315                 320

Leu Gly Val Ile Trp Gly Ser Glu Thr Thr Tyr Tyr Asn Ser Ala Leu
                325                 330                 335

Lys Ser Arg Leu Thr Ile Ile Lys Asp Asn Ser Lys Ser Gln Val Phe
            340                 345                 350

Leu Lys Met Asn Ser Leu Gln Thr Asp Asp Thr Ala Ile Tyr Tyr Cys
            355                 360                 365

Ala Lys His Tyr Tyr Tyr Gly Gly Ser Tyr Ala Met Asp Tyr Trp Gly
            370                 375                 380

Gln Gly Thr Ser Val Thr Val Ser Ser Gly Ser Thr Ser Gly Ser Gly
385                 390                 395                 400

Lys Pro Gly Ser Gly Glu Gly Ser Thr Lys Gly Asp Ile Gln Met Thr
                405                 410                 415

Gln Thr Thr Ser Ser Leu Ser Ala Ser Leu Gly Asp Arg Val Thr Ile
            420                 425                 430

Ser Cys Arg Ala Ser Gln Asp Ile Ser Lys Tyr Leu Asn Trp Tyr Gln
            435                 440                 445

Gln Lys Pro Asp Gly Thr Val Lys Leu Leu Ile Tyr His Thr Ser Arg
            450                 455                 460

Leu His Ser Gly Val Pro Ser Arg Phe Ser Gly Ser Gly Ser Gly Thr
465                 470                 475                 480

Asp Tyr Ser Leu Thr Ile Ser Asn Leu Glu Gln Glu Asp Ile Ala Thr
                485                 490                 495

Tyr Phe Cys Gln Gln Gly Asn Thr Leu Pro Tyr Thr Phe Gly Gly Gly
            500                 505                 510

Thr Lys Leu Glu Ile Thr Glu Ser Lys Tyr Gly Pro Pro Cys Pro Pro
            515                 520                 525

Cys Pro Met Phe Trp Val Leu Val Val Gly Gly Val Leu Ala Cys
            530                 535                 540

Tyr Ser Leu Leu Val Thr Val Ala Phe Ile Ile Phe Trp Val Lys Arg
545                 550                 555                 560

Gly Arg Lys Lys Leu Leu Tyr Ile Phe Lys Gln Pro Phe Met Arg Pro
                565                 570                 575

Val Gln Thr Thr Gln Glu Glu Asp Gly Cys Ser Cys Arg Phe Pro Glu
            580                 585                 590

Glu Glu Glu Gly Gly Cys Glu Leu Arg Val Lys Phe Ser Arg Ser Ala
            595                 600                 605

Asp Ala Pro Ala Tyr Gln Gln Gly Gln Asn Gln Leu Tyr Asn Glu Leu
            610                 615                 620

Asn Leu Gly Arg Arg Glu Glu Tyr Asp Val Leu Asp Lys Arg Arg Gly
625                 630                 635                 640

Arg Asp Pro Glu Met Gly Gly Lys Pro Arg Arg Lys Asn Pro Gln Glu
                645                 650                 655

Gly Leu Tyr Asn Glu Leu Gln Lys Asp Lys Met Ala Glu Ala Tyr Ser
            660                 665                 670
```

```
Glu Ile Gly Met Lys Gly Glu Arg Arg Gly Lys Gly His Asp Gly
            675                 680                 685

Leu Tyr Gln Gly Leu Ser Thr Ala Thr Lys Asp Thr Tyr Asp Ala Leu
        690                 695                 700

His Met Gln Ala Leu Pro Pro Arg
705                 710

<210> SEQ ID NO 17
<211> LENGTH: 2130
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Nucleic acid sequence of TN-LEU-19

<400> SEQUENCE: 17
atggagacag acacactcct gctatgggtg ctgctgctct gggttccagg ttccacaggt      60
gacattgtgc tgacccaatc tccagctatc ctgtctgcat ctccagggga gaaggtcaca     120
atgacttgca gggccagctc aagtgtaaat tacatggact ggtaccagaa gaagccagga     180
tcctccccca aacctggat ttatgccaca tccaacctgg cttctggagt ccctgctcgc      240
ttcagtggca gtgggtctgg gacctcttac tctctcacaa tcagcagagt ggaggctgaa     300
gatgctgcca cttattactg ccagcagtgg agttttaatc cacccacgtt cggaggggg      360 accaagctgg aaataaaagg cagtactagc ggtggtggct ccggggggcgg ttccggtggg    420 ggcggcagca gcgaggtgca gctgcagcag tctggggctg agctggtgaa gcctggggcc    480
tcagtgaaga tgtcctgcaa ggcttctggc tacacattta ccagttacaa tatgcactgg    540
gtaaagcaga cacctggaca gggcctggaa tggattggag ctatttatcc aggaaatggt    600
gatacttcct acaatcagaa gttcaaggc aaggccacat tgactgcaga caaatcctcc     660
agcacagcct acatgcagct cagcagcctg acatctgagg actctgcgga ctattactgt    720
gcaagatcta attattacgg tagtagctac tggttcttcg atgtctgggg cgcagggacc    780
acggtcaccg tctcctcagg aggtggtgga tccgaggtga agctgcagga aagcggccct   840
ggcctggtgg cccccagcca gagcctgagc gtgacctgca ccgtgagcgg cgtgagcctg    900
cccgactacg gcgtgagctg gatccggcag cccccaggga agggcctgga atggctgggc    960
gtgatctggg gcagcgagac cacctactac aacagcgccc tgaagagccg gctgaccatc   1020
atcaaggaca cagcaagag ccaggtgttc ctgaagatga acagcctgca gaccgacgac   1080
accgccatct actactgcgc caagcactac tactacggcg gcagctacgc catggactac   1140
tggggccagg gcaccagcgt gaccgtgagc agcggcagca cctccggcag cggcaagcct   1200
ggcagcggcg agggcagcac caagggcgac atccagatga cccagaccac ctccagcctg   1260
agcgccagcc tgggcgaccg ggtgaccatc agctgccggg ccagccagga catcagcaag   1320
tacctgaact ggtatcagca gaagcccgac ggcaccgtca agctgctgat ctaccacacc   1380
agccggctgc acagcggcgt gcccagccgg tttagcggca gcggctccgg caccgactac   1440
agcctgacca tctccaacct ggaacaggaa gatatcgcca cctactttg ccagcagggc   1500 aacacactgc cctacacctt ggcggcggga acaaagctgg aaatcaccga gagcaagtac   1560
ggaccgccct gccccccttg ccctatgttc tgggtgctgg tggtggtcgg aggcgtgctg   1620
gcctgctaca gcctgctggt caccgtgcc ttcatcatct ttgggtgaa acggggcaga   1680 aagaaactcc tgtatatatt caaacaacca tttatgagac cagtacaaac tactcaagag   1740
```

| | |
|---|---:|
| gaagatggct gtagctgccg atttccagaa gaagaagaag gaggatgtga actgcgggtg | 1800 |
| aagttcagca gaagcgccga cgcccctgcc taccagcagg gccagaatca gctgtacaac | 1860 |
| gagctgaacc tgggcagaag ggaagagtac gacgtcctgg ataagcggag aggccgggac | 1920 |
| cctgagatgg gcggcaagcc tcggcggaag aaccccagg aaggcctgta taacgaactg | 1980 |
| cagaaagaca agatggccga ggcctacagc gagatcggca tgaagggcga gcggaggcgg | 2040 |
| ggcaagggcc acgacggcct gtatcagggc ctgtccaccg ccaccaagga tacctacgac | 2100 |
| gccctgcaca tgcaggccct gccccccaagg | 2130 |

<210> SEQ ID NO 18
<211> LENGTH: 2136
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Nucleic acid sequence of TN-OF-19

<400> SEQUENCE: 18

| | |
|---|---:|
| atggccttac cagtgaccgc cttgctcctg ccgctggcct tgctgctcca cgccgccagg | 60 |
| ccggaaattg tgttgacaca gtctccagcc accctgtctt tgtctccagg ggaaagagcc | 120 |
| accctctcct gcagggccag tcagagtgtt agcagctact tagcctggta ccaacagaaa | 180 |
| cctggccagg ctcccaggct cctcatctat gatgcatcca acagggccac tggcatccca | 240 |
| gccaggttca gtggcagtgg gtctgggaca gacttcactc tcaccatcag cagcctagag | 300 |
| cctgaagatt ttgcagttta ttactgtcag cagcgtagca actggccgat caccttcggc | 360 |
| caagggacac gactggagat taaaggcagt actagcggtg gtggctccgg gggcggttcc | 420 |
| ggtggggcg gcagcagcga agtgcagctg gtggagtctg ggggaggctt ggtacagcct | 480 |
| ggcaggtccc tgagactctc ctgtgcagcc tctggattca cctttaatga ttatgccatg | 540 |
| cactgggtcc ggcaagctcc agggaagggc ctggagtggg tctcaactat tagttggaat | 600 |
| agtggttcca taggctatgc ggactctgtg aagggccgat tcaccatctc cagagacaac | 660 |
| gccaagaagt ccctgtatct gcaaatgaac agtctgagag ctgaggacac ggccttgtat | 720 |
| tactgtgcaa aagatataca gtacggcaac tactactacg gtatggacgt ctggggccaa | 780 |
| gggaccacgg tcaccgtctc ctcaggaggt ggtggatccg aggtgaagct gcaggaaagc | 840 |
| ggccctggcc tggtggcccc cagccagagc ctgagcgtga cctgcaccgt gagcggcgtg | 900 |
| agcctgcccg actacggcgt gagctggatc cggcagcccc caggaagggg cctggaatgg | 960 |
| ctgggcgtga tctggggcag cgagaccacc tactacaaca gcgccctgaa gagccggctg | 1020 |
| accatcatca aggacaacag caagagccag gtgttcctga gatgaacag cctgcagacc | 1080 |
| gacgacaccg ccatctacta ctgcgccaag cactactact acggcggcag ctacgccatg | 1140 |
| gactactggg gccagggcac cagcgtgacc gtgagcagcg gcagcacctc cggcagcggc | 1200 |
| aagcctggca cggcgaggg cagcaccaag ggcgacatcc agatgaccca gaccacctcc | 1260 |
| agcctgagcg ccagcctggg cgaccgggtg accatcagct gccgggccag ccaggacatc | 1320 |
| agcaagtacc tgaactggta tcagcagaag cccgacggca ccgtcaagct gctgatctac | 1380 |
| cacaccagcc ggctgcacag cggcgtgccc agcggttta gcggcagcgg ctccggcacc | 1440 |
| gactacagcc tgaccatctc caacctggaa caggaagata tcgccaccta cttttgccag | 1500 |
| cagggcaaca cactgcccta caccttggc ggcggaacaa agctggaaat caccgagagc | 1560 |

```
aagtacggac cgccctgccc cccttgccct atgttctggg tgctggtggt ggtcggaggc    1620
gtgctggcct gctacagcct gctggtcacc gtggccttca tcatcttttg ggtgaaacgg    1680
ggcagaaaga aactcctgta tatattcaaa caaccattta tgagaccagt acaaactact    1740
caagaggaag atggctgtag ctgccgattt ccagaagaag aagaaggagg atgtgaactg    1800
cgggtgaagt tcagcagaag cgccgacgcc cctgcctacc agcagggcca gaatcagctg    1860
tacaacgagc tgaacctggg cagaagggaa gagtacgacg tcctggataa gcggagaggc    1920
cgggaccctg agatgggcgg caagcctcgg cggaagaacc cccaggaagg cctgtataac    1980
gaactgcaga agacaagat ggccgaggcc tacagcgaga tcggcatgaa gggcgagcgg    2040
aggcggggca agggccacga cggcctgtat cagggcctgt ccaccgccac caaggatacc    2100
tacgacgccc tgcacatgca ggccctgccc ccaagg                              2136

<210> SEQ ID NO 19
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Amino acid sequence of flexible linker I

<400> SEQUENCE: 19

Gly Gly Gly Gly Ser Gly Gly Gly Gly Ser Gly Gly Gly Gly Ser
1               5                  10                  15

<210> SEQ ID NO 20
<211> LENGTH: 45
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Nucleic acid sequence of flexible linker I

<400> SEQUENCE: 20
ggtggcggtg gctcgggcgg tggtgggtcg ggtggcggcg gatct                     45

<210> SEQ ID NO 21
<211> LENGTH: 321
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Nucleotide sequence of the light chain of
      single-chain variable region (VL) derived from FMC63 antibody

<400> SEQUENCE: 21
gacatccaga tgacacagac tacatcctcc ctgtctgcct ctctgggaga cagagtcacc     60
atcagttgca gggcaagtca ggacattagt aaatatttaa attggtatca gcagaaacca    120
gatggaactg ttaaactcct gatctaccat acatcaagat tacactcagg agtcccatca    180
aggttcagtg gcagtgggtc tggaacagat tattctctca ccattagcaa cctggagcaa    240
gaagatattg ccacttactt ttgccaacag ggtaatacgc ttccgtacac gttcggaggg    300
gggaccaagc tggagatcac a                                              321
```

<210> SEQ ID NO 22
<211> LENGTH: 360
<212> TYPE: DNA
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Nucleotide sequence of the heavy chain of
     single-chain variable region (VH) derived from FMC63 antibody

<400> SEQUENCE: 22

```
gaggtgaaac tgcaggagtc aggacctggc ctggtggcgc cctcacagag cctgtccgtc    60
acatgcactg tctcaggggt ctcattaccc gactatggtg taagctggat tcgccagcct   120
ccacgaaagg gtctggagtg gctgggagta atatgggta gtgaaaccac atactataat   180
tcagctctca atccagact gaccatcatc aaggacaact ccaagagcca agttttctta   240
aaaatgaaca gtctgcaaac tgatgacaca gccatttact actgtgccaa acattattac   300
tacggtggta gctatgctat ggactactgg ggccaaggaa cctcagtcac cgtctcctca   360
```

<210> SEQ ID NO 23
<211> LENGTH: 472
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 23

```
Met Asp Ile Gln Leu Thr Gln Ser Pro Ala Ile Leu Ser Ala Ser Pro
1               5                   10                  15

Gly Glu Lys Val Thr Met Thr Cys Arg Ala Ser Ser Ser Leu Ser Phe
            20                  25                  30

Met His Trp Tyr Gln Gln Lys Pro Gly Ser Ser Pro Lys Pro Trp Ile
        35                  40                  45

Tyr Ala Thr Ser Asn Leu Ala Ser Gly Val Pro Ala Arg Phe Ser Gly
    50                  55                  60

Ser Gly Ser Gly Thr Ser Tyr Ser Leu Thr Ile Ser Thr Val Glu Ala
65                  70                  75                  80

Glu Asp Ala Ala Ser Tyr Phe Cys His Gln Trp Ser Ser Asn Pro Leu
                85                  90                  95

Thr Phe Gly Ala Gly Thr Lys Leu Glu Ile Ser Ser Gly Gly Gly Gly
            100                 105                 110

Ser Gly Gly Gly Gly Ser Gly Asp Val Met Gly Val Asp Ser Gly Gly
        115                 120                 125

Gly Leu Val Gln Pro Gly Gly Ser Arg Lys Leu Ser Cys Ala Ala Pro
    130                 135                 140

Gly Phe Thr Phe Ser Ser Phe Gly Met His Trp Val Arg Gln Ala Pro
145                 150                 155                 160

Glu Lys Gly Leu Glu Trp Val Ala Tyr Ile Ser Ser Pro Ser Ser Thr
                165                 170                 175

Leu His Tyr Ala Asp Arg Val Lys Gly Arg Phe Thr Ile Ser Arg Asp
            180                 185                 190

Asn Pro Lys Asn Thr Leu Phe Leu Gln Met Lys Leu Pro Ser Leu Cys
        195                 200                 205

Tyr Gly Leu Leu Gly Pro Arg Asp His Val His Arg Leu Leu Lys Thr
    210                 215                 220
```

```
Arg Leu Ser Asn Ser Ile Met Tyr Phe Ser His Phe Val Pro Val Phe
225                 230                 235                 240

Leu Pro Ala Lys Pro Thr Thr Thr Pro Ala Pro Arg Pro Pro Thr Pro
            245                 250                 255

Ala Pro Thr Ile Ala Ser Gln Pro Leu Ser Leu Arg Pro Glu Ala Cys
                260                 265                 270

Arg Pro Ala Ala Gly Gly Ala Val His Thr Arg Gly Leu Asp Phe Ala
            275                 280                 285

Cys Asp Ile Tyr Ile Trp Ala Pro Leu Ala Gly Thr Cys Gly Val Leu
290                 295                 300

Leu Leu Ser Leu Val Ile Thr Leu Tyr Cys Arg Ser Lys Arg Gly Arg
305                 310                 315                 320

Lys Lys Leu Leu Tyr Ile Phe Lys Gln Pro Phe Met Arg Pro Val Gln
            325                 330                 335

Thr Thr Gln Glu Glu Asp Gly Cys Ser Cys Arg Phe Pro Glu Glu Glu
                340                 345                 350

Glu Gly Gly Cys Glu Leu Glu Phe Arg Val Lys Phe Ser Arg Ser Ala
            355                 360                 365

Asp Ala Pro Ala Tyr Gln Gln Gly Gln Asn Gln Leu Tyr Asn Glu Leu
370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
            405                 410                 415

Gly Leu Tyr Asn Glu Leu Gln Lys Asp Lys Met Ala Glu Ala Tyr Ser
                420                 425                 430

Glu Ile Gly Met Lys Gly Glu Arg Arg Arg Gly Lys Gly His Asp Gly
            435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 24
<211> LENGTH: 492
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 24

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ala Ile Leu
            20                  25                  30

Ser Ala Ser Pro Gly Glu Lys Val Thr Met Thr Cys Arg Ala Ser Ser
        35                  40                  45

Ser Leu Ser Phe Met His Trp Tyr Gln Gln Lys Pro Gly Ser Ser Pro
    50                  55                  60

Lys Pro Trp Ile Tyr Ala Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95
```

Thr Val Glu Ala Glu Asp Ala Ala Ser Tyr Phe Cys His Gln Trp Ser
            100                 105                 110

Ser Asn Pro Leu Thr Phe Gly Ala Gly Thr Lys Leu Glu Ile Ser Ser
            115                 120                 125

Gly Gly Gly Gly Ser Gly Gly Gly Ser Gly Asp Val Met Gly Val
        130                 135                 140

Asp Ser Gly Gly Gly Leu Val Gln Pro Gly Ser Arg Lys Leu Ser
145                 150                 155                 160

Cys Ala Ala Pro Gly Phe Thr Phe Ser Ser Phe Gly Met His Trp Val
                165                 170                 175

Arg Gln Ala Pro Glu Lys Gly Leu Glu Trp Val Ala Tyr Ile Ser Ser
            180                 185                 190

Pro Ser Ser Thr Leu His Tyr Ala Asp Arg Val Lys Gly Arg Phe Thr
            195                 200                 205

Ile Ser Arg Asp Asn Pro Lys Asn Thr Leu Phe Leu Gln Met Lys Leu
        210                 215                 220

Pro Ser Leu Cys Tyr Gly Leu Gly Pro Arg Asp His Val His Arg
225                 230                 235                 240

Leu Leu Lys Thr Arg Leu Ser Asn Ser Ile Met Tyr Phe Ser His Phe
                245                 250                 255

Val Pro Val Phe Leu Pro Ala Lys Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Glu Phe Arg Val Lys Phe
        370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 25
<211> LENGTH: 377

-continued

```
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 25
```

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ala Ile Leu
            20                  25                  30

Ser Ala Ser Pro Gly Glu Lys Val Thr Met Thr Cys Arg Ala Ser Ser
        35                  40                  45

Ser Leu Ser Phe Met His Trp Tyr Gln Gln Lys Pro Gly Ser Ser Pro
    50                  55                  60

Lys Pro Trp Ile Tyr Ala Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Thr Val Glu Ala Glu Asp Ala Ala Ser Tyr Phe Cys His Gln Trp Ser
            100                 105                 110

Ser Asn Pro Leu Thr Phe Gly Ala Gly Thr Lys Leu Glu Ile Gly Gly
        115                 120                 125

Gly Gly Ser Gly Gly Gly Ser Gly Gly Gly Ser Asp Val Met
130                 135                 140

Gly Val Asp Ser Gly Gly Leu Val Gln Pro Gly Gly Ser Arg Lys
145                 150                 155                 160

Leu Ser Cys Ala Ala Pro Gly Phe Thr Phe Ser Ser Phe Gly Met His
                165                 170                 175

Trp Val Arg Gln Ala Pro Glu Lys Gly Leu Glu Trp Val Ala Tyr Ile
            180                 185                 190

Ser Ser Pro Ser Ser Thr Leu His Tyr Ala Asp Arg Val Lys Gly Arg
        195                 200                 205

Phe Thr Ile Ser Arg Asp Asn Pro Lys Asn Thr Leu Phe Leu Gln Met
    210                 215                 220

Lys Leu Pro Ser Leu Cys Tyr Gly Leu Leu Gly Pro Arg Asp His Val
225                 230                 235                 240

His Arg Leu Leu Thr Arg Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Arg Ser Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Glu Phe Glu Leu Gly Thr Phe Lys Thr
        355                 360                 365

Asn Asp Leu Gln Gly Ser Cys Arg Ser
    370                 375

<210> SEQ ID NO 26
<211> LENGTH: 377
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 26

Met Ala Leu Pro Val Thr Ala Leu Leu Leu Pro Leu Ala Leu Leu Leu
1               5                   10                  15

His Ala Ala Arg Pro Asp Val Met Gly Val Asp Ser Gly Gly Gly Leu
            20                  25                  30

Val Gln Pro Gly Gly Ser Arg Lys Leu Ser Cys Ala Ala Pro Gly Phe
        35                  40                  45

Thr Phe Ser Ser Phe Gly Met His Trp Val Arg Gln Ala Pro Glu Lys
    50                  55                  60

Gly Leu Glu Trp Val Ala Tyr Ile Ser Ser Pro Ser Ser Thr Leu His
65                  70                  75                  80

Tyr Ala Asp Arg Val Lys Gly Arg Phe Thr Ile Ser Arg Asp Asn Pro
                85                  90                  95

Lys Asn Thr Leu Phe Leu Gln Met Lys Leu Pro Ser Leu Cys Tyr Gly
            100                 105                 110

Leu Leu Gly Pro Arg Asp His Val His Arg Leu Leu Gly Gly Gly Gly
        115                 120                 125

Ser Gly Gly Gly Ser Gly Gly Gly Ser Asp Ile Gln Leu Thr
    130                 135                 140

Gln Ser Pro Ala Ile Leu Ser Ala Ser Pro Gly Glu Lys Val Thr Met
145                 150                 155                 160

Thr Cys Arg Ala Ser Ser Ser Leu Ser Phe Met His Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Thr Val Glu Ala Glu Asp Ala Ala Ser Tyr
    210                 215                 220

Phe Cys His Gln Trp Ser Ser Asn Pro Leu Thr Phe Gly Ala Gly Thr
225                 230                 235                 240

Lys Leu Glu Ile Thr Arg Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Arg Ser Lys Arg Gly
305                 310                 315                 320

Arg Lys Lys Leu Leu Tyr Ile Phe Lys Gln Pro Phe Met Arg Pro Val
                325                 330                 335

```
Gln Thr Thr Gln Glu Glu Asp Gly Cys Ser Cys Arg Phe Pro Glu Glu
                340                 345                 350

Glu Glu Gly Gly Cys Glu Leu Glu Phe Glu Leu Gly Thr Phe Lys Thr
        355                 360                 365

Asn Asp Leu Gln Gly Ser Cys Arg Ser
    370                 375

<210> SEQ ID NO 27
<211> LENGTH: 396
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 27

Met Ala Leu Pro Val Thr Ala Leu Leu Leu Pro Leu Ala Leu Leu Leu
1               5                   10                  15

His Ala Ala Arg Pro Gln Ile Val Leu Ser Gln Ser Pro Ala Ile Leu
                20                  25                  30

Ser Ala Ser Pro Gly Glu Lys Val Thr Met Thr Cys Arg Ala Ser Ser
            35                  40                  45

Ser Val Ser Tyr Ile His Trp Phe Gln Gln Lys Pro Gly Ser Ser Pro
    50                  55                  60

Lys Pro Trp Ile Tyr Ala Thr Ser Asn Leu Ala Ser Gly Val Pro Val
65                  70                  75                  80

Arg Phe Ser Gly Ser Gly Ser Gly Thr Ser Tyr Ser Leu Thr Ile Ser
                85                  90                  95

Arg Val Glu Ala Glu Asp Ala Ala Thr Tyr Tyr Cys Gln Gln Trp Thr
            100                 105                 110

Ser Asn Pro Pro Thr Phe Gly Gly Gly Thr Lys Leu Glu Ile Lys Gly
        115                 120                 125

Gly Gly Gly Ser Gly Gly Gly Gly Ser Gly Gly Gly Gly Ser Gln Val
    130                 135                 140

Gln Leu Gln Gln Pro Gly Ala Glu Leu Val Lys Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Gly Arg Gly Leu Glu Trp Ile Gly Ala
            180                 185                 190

Ile Tyr Pro Gly Asn Gly Asp Thr Ser Tyr Asn Gln Lys Phe Lys Gly
        195                 200                 205

Lys Ala Thr Leu Thr Ala Asp Lys Ser Ser Ser Thr Ala Tyr Met Gln
    210                 215                 220

Leu Ser Ser Leu Thr Ser Glu Asp Ser Ala Val Tyr Tyr Cys Ala Arg
225                 230                 235                 240

Ser Thr Tyr Tyr Gly Gly Asp Trp Tyr Phe Asn Val Trp Gly Ala Gly
                245                 250                 255

Thr Thr Val Thr Val Ser Ala Thr Arg Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300
```

```
Leu Asp Phe Ala Cys Asp Ile Tyr Ile Trp Ala Pro Leu Ala Gly Thr
305                 310                 315                 320

Cys Gly Val Leu Leu Ser Leu Val Ile Thr Leu Tyr Cys Arg Ser
            325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
            355                 360                 365

Pro Glu Glu Glu Gly Gly Cys Glu Leu Glu Phe Glu Leu Gly Thr
            370                 375                 380

Phe Lys Thr Asn Asp Leu Gln Gly Ser Cys Arg Ser
385                 390                 395
```

```
<210> SEQ ID NO 28
<211> LENGTH: 396
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 28

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Lys Pro Gly Ala Ser Val Lys Met Ser Cys Lys Ala Ser Gly Tyr
        35                  40                  45

Thr Phe Thr Ser Tyr Asn Met His Trp Val Lys Gln Thr Pro Gly Arg
    50                  55                  60

Gly Leu Glu Trp Ile Gly Ala Ile Tyr Pro Gly Asn Gly Asp Thr Ser
65                  70                  75                  80

Tyr Asn Gln Lys Phe Lys Gly Lys Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Arg Ser Thr Tyr Tyr Gly Gly Asp Trp Tyr
        115                 120                 125

Phe Asn Val Trp Gly Ala Gly Thr Thr Val Thr Val Ser Ala Gly Gly
    130                 135                 140

Gly Gly Ser Gly Gly Gly Gly Ser Gly Gly Gly Gly Ser Gln Ile Val
145                 150                 155                 160

Leu Ser Gln Ser Pro Ala Ile Leu Ser Ala Ser Pro Gly Glu Lys Val
                165                 170                 175

Thr Met Thr Cys Arg Ala Ser Ser Ser Val Ser Tyr Ile His Trp Phe
            180                 185                 190

Gln Gln Lys Pro Gly Ser Ser Pro Lys Pro Trp Ile Tyr Ala Thr Ser
        195                 200                 205

Asn Leu Ala Ser Gly Val Pro Val Arg Phe Ser Gly Ser Gly Ser Gly
    210                 215                 220

Thr Ser Tyr Ser Leu Thr Ile Ser Arg Val Glu Ala Glu Asp Ala Ala
225                 230                 235                 240

Thr Tyr Tyr Cys Gln Gln Trp Thr Ser Asn Pro Pro Thr Phe Gly Gly
                245                 250                 255
```

```
Gly Thr Lys Leu Glu Ile Lys Thr Arg Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Glu Phe Glu Leu Gly Thr
    370                 375                 380

Phe Lys Thr Asn Asp Leu Gln Gly Ser Cys Arg Ser
385                 390                 395
```

<210> SEQ ID NO 29
<211> LENGTH: 715
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 29

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
            20                  25                  30

Val Lys Pro Gly Ala Ser Val Lys Met Ser Cys Lys Ala Ser Gly Tyr
        35                  40                  45

Thr Phe Thr Ser Tyr Asn Met His Trp Val Lys Gln Thr Pro Gly Gln
    50                  55                  60

Gly Leu Glu Trp Ile Gly Ala Ile Tyr Pro Gly Asn Gly Asp Thr Ser
65                  70                  75                  80

Tyr Asn Gln Lys Phe Lys Gly Lys Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Asp Tyr Tyr Cys Ala Arg Ser Asn Tyr Tyr Gly Ser Ser Tyr Trp
        115                 120                 125

Phe Phe Asp Val Trp Gly Ala Gly Thr Thr Val Thr Val Ser Ser Gly
    130                 135                 140

Gly Gly Gly Ser Gly Gly Gly Gly Ser Gly Gly Gly Gly Ser Asp Ile
145                 150                 155                 160

Val Leu Thr Gln Ser Pro Ala Ile Leu Ser Ala Ser Pro Gly Glu Lys
                165                 170                 175

Val Thr Met Thr Cys Arg Ala Ser Ser Ser Val Asn Tyr Met Asp Trp
            180                 185                 190

Tyr Gln Lys Lys Pro Gly Ser Ser Pro Lys Pro Trp Ile Tyr Ala Thr
        195                 200                 205
```

-continued

Ser Asn Leu Ala Ser Gly Val Pro Ala Arg Phe Ser Gly Ser
210                215                220

Gly Thr Ser Tyr Ser Leu Thr Ile Ser Arg Val Glu Ala Glu Asp Ala
225                230                235                240

Ala Thr Tyr Tyr Cys Gln Gln Trp Ser Phe Asn Pro Pro Thr Phe Gly
                245                250                255

Gly Gly Thr Lys Leu Glu Ile Lys Glu Ser Lys Tyr Gly Pro Pro Cys
            260                265                270

Pro Pro Cys Pro Ala Pro Glu Phe Leu Gly Gly Pro Ser Val Phe Leu
        275                280                285

Phe Pro Pro Lys Pro Lys Asp Thr Leu Met Ile Ser Arg Thr Pro Glu
    290                295                300

Val Thr Cys Val Val Val Asp Val Ser Gln Glu Asp Pro Glu Val Gln
305                310                315                320

Phe Asn Trp Tyr Val Asp Gly Val Glu Val His Asn Ala Lys Thr Lys
                325                330                335

Pro Arg Glu Glu Gln Phe Asn Ser Thr Tyr Arg Val Val Ser Val Leu
            340                345                350

Thr Val Leu His Gln Asp Trp Leu Asn Gly Lys Glu Tyr Lys Cys Lys
        355                360                365

Val Ser Asn Lys Gly Leu Pro Ser Ser Ile Glu Lys Thr Ile Ser Lys
370                375                380

Ala Lys Gly Gln Pro Arg Glu Pro Gln Val Tyr Thr Leu Pro Pro Ser
385                390                395                400

Gln Glu Glu Met Thr Lys Asn Gln Val Ser Leu Thr Cys Leu Val Lys
                405                410                415

Gly Phe Tyr Pro Ser Asp Ile Ala Val Glu Trp Glu Ser Asn Gly Gln
            420                425                430

Pro Glu Asn Asn Tyr Lys Thr Thr Pro Pro Val Leu Asp Ser Asp Gly
        435                440                445

Ser Phe Phe Leu Tyr Ser Arg Leu Thr Val Asp Lys Ser Arg Trp Gln
    450                455                460

Glu Gly Asn Val Phe Ser Cys Ser Val Met His Glu Ala Leu His Asn
465                470                475                480

His Tyr Thr Gln Lys Ser Leu Ser Leu Ser Leu Gly Lys Phe Trp Val
                485                490                495

Leu Val Val Val Gly Gly Val Leu Ala Cys Tyr Ser Leu Leu Val Thr
            500                505                510

Val Ala Phe Ile Ile Phe Trp Val Arg Ser Lys Arg Ser Arg Leu Leu
        515                520                525

His Ser Asp Tyr Met Asn Met Thr Pro Arg Arg Pro Gly Pro Thr Arg
    530                535                540

Lys His Tyr Gln Pro Tyr Ala Pro Pro Arg Asp Phe Ala Ala Tyr Arg
545                550                555                560

Ser Lys Arg Gly Arg Lys Lys Leu Leu Tyr Ile Phe Lys Gln Pro Phe
                565                570                575

Met Arg Pro Val Gln Thr Thr Gln Glu Glu Asp Gly Cys Ser Cys Arg
            580                585                590

Phe Pro Glu Glu Glu Glu Gly Gly Cys Glu Leu Arg Val Lys Phe Ser
        595                600                605

Arg Ser Ala Asp Ala Pro Ala Tyr Lys Gln Gly Gln Asn Gln Leu Tyr
    610                615                620

Asn Glu Leu Asn Leu Gly Arg Arg Glu Glu Tyr Asp Val Leu Asp Lys

```
                    625                 630                 635                 640
Arg Arg Gly Arg Asp Pro Glu Met Gly Gly Lys Pro Arg Arg Lys Asn
                645                 650                 655

Pro Gln Glu Gly Leu Tyr Asn Glu Leu Gln Lys Asp Lys Met Ala Glu
                660                 665                 670

Ala Tyr Ser Glu Ile Gly Met Lys Gly Glu Arg Arg Arg Gly Lys Gly
                675                 680                 685

His Asp Gly Leu Tyr Gln Gly Leu Ser Thr Ala Thr Lys Asp Thr Tyr
                690                 695                 700

Asp Ala Leu His Met Gln Ala Leu Pro Pro Arg
705                 710                 715

<210> SEQ ID NO 30
<211> LENGTH: 715
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 30

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
                20                  25                  30

Val Lys Pro Gly Ala Ser Val Lys Met Ser Cys Lys Ala Ser Gly Tyr
            35                  40                  45

Thr Phe Thr Ser Tyr Asn Met His Trp Val Lys Gln Thr Pro Gly Gln
        50                  55                  60

Gly Leu Glu Trp Ile Gly Ala Ile Tyr Pro Gly Asn Gly Asp Thr Ser
65              70                  75                  80

Tyr Asn Gln Lys Phe Lys Gly Lys Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Asp Tyr Tyr Cys Ala Arg Ser Asn Tyr Tyr Gly Ser Ser Tyr Trp
        115                 120                 125

Phe Phe Asp Val Trp Gly Ala Gly Thr Thr Val Thr Val Ser Ser Gly
    130                 135                 140

Gly Gly Gly Ser Gly Gly Gly Gly Ser Gly Gly Gly Gly Ser Asp Ile
145                 150                 155                 160

Val Leu Thr Gln Ser Pro Ala Ile Leu Ser Ala Ser Pro Gly Glu Lys
                165                 170                 175

Val Thr Met Thr Cys Arg Ala Ser Ser Ser Val Asn Tyr Met Asp Trp
            180                 185                 190

Tyr Gln Lys Lys Pro Gly Ser Ser Pro Lys Pro Trp Ile Tyr Ala Thr
        195                 200                 205

Ser Asn Leu Ala Ser Gly Val Pro Ala Arg Phe Ser Gly Ser Gly Ser
    210                 215                 220

Gly Thr Ser Tyr Ser Leu Thr Ile Ser Arg Val Glu Ala Glu Asp Ala
225                 230                 235                 240

Ala Thr Tyr Tyr Cys Gln Gln Trp Ser Phe Asn Pro Pro Thr Phe Gly
                245                 250                 255

Gly Gly Thr Lys Leu Glu Ile Lys Glu Ser Lys Tyr Gly Pro Pro Cys
```

-continued

```
                260                 265                 270
Pro Pro Cys Pro Ala Pro Glu Phe Leu Gly Pro Ser Val Phe Leu
            275                 280                 285
Phe Pro Pro Lys Pro Lys Asp Thr Leu Met Ile Ser Arg Thr Pro Glu
        290                 295                 300
Val Thr Cys Val Val Val Asp Val Ser Gln Glu Asp Pro Glu Val Gln
305                 310                 315                 320
Phe Asn Trp Tyr Val Asp Gly Val Glu Val His Asn Ala Lys Thr Lys
                325                 330                 335
Pro Arg Glu Glu Gln Phe Asn Ser Thr Tyr Arg Val Val Ser Val Leu
            340                 345                 350
Thr Val Leu His Gln Asp Trp Leu Asn Gly Lys Glu Tyr Lys Cys Lys
        355                 360                 365
Val Ser Asn Lys Gly Leu Pro Ser Ser Ile Glu Lys Thr Ile Ser Lys
        370                 375                 380
Ala Lys Gly Gln Pro Arg Glu Pro Gln Val Tyr Thr Leu Pro Pro Ser
385                 390                 395                 400
Gln Glu Glu Met Thr Lys Asn Gln Val Ser Leu Thr Cys Leu Val Lys
                405                 410                 415
Gly Phe Tyr Pro Ser Asp Ile Ala Val Glu Trp Glu Ser Asn Gly Gln
            420                 425                 430
Pro Glu Asn Asn Tyr Lys Thr Thr Pro Pro Val Leu Asp Ser Asp Gly
        435                 440                 445
Ser Phe Phe Leu Tyr Ser Arg Leu Thr Val Asp Lys Ser Arg Trp Gln
        450                 455                 460
Glu Gly Asn Val Phe Ser Cys Ser Val Met His Glu Ala Leu His Asn
465                 470                 475                 480
His Tyr Thr Gln Lys Ser Leu Ser Leu Ser Leu Gly Lys Phe Trp Val
                485                 490                 495
Leu Val Val Val Gly Val Leu Ala Cys Tyr Ser Leu Leu Val Thr
            500                 505                 510
Val Ala Phe Ile Ile Phe Trp Val Arg Ser Lys Arg Ser Arg Leu Leu
        515                 520                 525
His Ser Asp Tyr Met Asn Met Thr Pro Arg Arg Pro Gly Pro Thr Arg
        530                 535                 540
Lys His Tyr Gln Pro Tyr Ala Pro Pro Arg Asp Phe Ala Ala Tyr Arg
545                 550                 555                 560
Ser Lys Arg Gly Arg Lys Lys Leu Leu Tyr Ile Phe Lys Gln Pro Phe
                565                 570                 575
Met Arg Pro Val Gln Thr Thr Gln Glu Glu Asp Gly Cys Ser Cys Arg
            580                 585                 590
Phe Pro Glu Glu Glu Glu Gly Gly Cys Glu Leu Arg Val Lys Phe Ser
        595                 600                 605
Arg Ser Ala Asp Ala Pro Ala Tyr Lys Gln Gly Gln Asn Gln Leu Tyr
        610                 615                 620
Asn Glu Leu Asn Leu Gly Arg Arg Glu Glu Tyr Asp Val Leu Asp Lys
625                 630                 635                 640
Arg Arg Gly Arg Asp Pro Glu Met Gly Gly Lys Pro Arg Arg Lys Asn
                645                 650                 655
Pro Gln Glu Gly Leu Tyr Asn Glu Leu Gln Lys Asp Lys Met Ala Glu
            660                 665                 670
Ala Tyr Ser Glu Ile Gly Met Lys Gly Glu Arg Arg Arg Gly Lys Gly
        675                 680                 685
```

```
His Asp Gly Leu Tyr Gln Gly Leu Ser Thr Ala Thr Lys Asp Thr Tyr
            690                 695                 700

Asp Ala Leu His Met Gln Ala Leu Pro Pro Arg
705                 710                 715

<210> SEQ ID NO 31
<211> LENGTH: 671
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 31

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ile Leu
            20                  25                  30

Ser Ala Ser Pro Gly Glu Lys Val Thr Met Thr Cys Arg Ala Ser Ser
        35                  40                  45

Ser Val Asn Tyr Met Asp Trp Tyr Gln Lys Lys Pro Gly Ser Ser Pro
50                  55                  60

Lys Pro Trp Ile Tyr Ala Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Arg Val Glu Ala Glu Asp Ala Ala Thr Tyr Tyr Cys Gln Gln Trp Ser
            100                 105                 110

Phe Asn Pro Pro Thr Phe Gly Gly Gly Thr Lys Leu Glu Ile Lys Gly
        115                 120                 125

Gly Gly Gly Ser Gly Gly Gly Gly Ser Gly Gly Gly Gly Ser Glu Val
130                 135                 140

Gln Leu Gln Gln Ser Gly Ala Glu Leu Val Lys Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Gly Gln Gly Leu Glu Trp Ile Gly Ala
            180                 185                 190

Ile Tyr Pro Gly Asn Gly Asp Thr Ser Tyr Asn Gln Lys Phe Lys Gly
        195                 200                 205

Lys Ala Thr Leu Thr Ala Asp Lys Ser Ser Thr Ala Tyr Met Gln
210                 215                 220

Leu Ser Ser Leu Thr Ser Glu Asp Ser Ala Asp Tyr Tyr Cys Ala Arg
225                 230                 235                 240

Ser Asn Tyr Tyr Gly Ser Ser Tyr Trp Phe Phe Asp Val Trp Gly Ala
                245                 250                 255

Gly Thr Thr Val Thr Val Ser Ser Glu Ser Lys Tyr Gly Pro Pro Cys
            260                 265                 270

Pro Pro Cys Pro Ala Pro Glu Phe Leu Gly Gly Pro Ser Val Phe Leu
        275                 280                 285

Phe Pro Pro Lys Pro Lys Asp Thr Leu Met Ile Ser Arg Thr Pro Glu
290                 295                 300

Val Thr Cys Val Val Val Asp Val Ser Gln Glu Asp Pro Glu Val Gln
305                 310                 315                 320
```

Phe Asn Trp Tyr Val Asp Gly Val Glu Val His Asn Ala Lys Thr Lys
            325                 330                 335

Pro Arg Glu Glu Gln Phe Asn Ser Thr Tyr Arg Val Val Ser Val Leu
        340                 345                 350

Thr Val Leu His Gln Asp Trp Leu Asn Gly Lys Glu Tyr Lys Cys Lys
        355                 360                 365

Val Ser Asn Lys Gly Leu Pro Ser Ser Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
            405                 410                 415

Gly Phe Tyr Pro Ser Asp Ile Ala Val Glu Trp Glu Ser Asn Gly Gln
        420                 425                 430

Pro Glu Asn Asn Tyr Lys Thr Thr Pro Pro Val Leu Asp Ser Asp Gly
        435                 440                 445

Ser Phe Phe Leu Tyr Ser Arg Leu Thr Val Asp Lys Ser Arg Trp Gln
450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys Ile Tyr Ile
            485                 490                 495

Trp Ala Pro Leu Ala Gly Thr Cys Gly Val Leu Leu Leu Ser Leu Val
        500                 505                 510

Ile Thr Leu Tyr Cys Lys Arg Gly Arg Lys Lys Leu Leu Tyr Ile Phe
        515                 520                 525

Lys Gln Pro Phe Met Arg Pro Val Gln Thr Thr Gln Glu Glu Asp Gly
530                 535                 540

Cys Ser Cys Arg Phe Pro Glu Glu Glu Glu Gly Gly Cys Glu Leu Arg
545                 550                 555                 560

Val Lys Phe Ser Arg Ser Ala Asp Ala Pro Ala Tyr Lys Gln Gly Gln
            565                 570                 575

Asn Gln Leu Tyr Asn Glu Leu Asn Leu Gly Arg Arg Glu Glu Tyr Asp
        580                 585                 590

Val Leu Asp Lys Arg Arg Gly Arg Asp Pro Glu Met Gly Gly Lys Pro
        595                 600                 605

Arg Arg Lys Asn Pro Gln Glu Gly Leu Tyr Asn Glu Leu Gln Lys Asp
610                 615                 620

Lys Met Ala Glu Ala Tyr Ser Glu Ile Gly Met Lys Gly Glu Arg Arg
625                 630                 635                 640

Arg Gly Lys Gly His Asp Gly Leu Tyr Gln Gly Leu Ser Thr Ala Thr
            645                 650                 655

Lys Asp Thr Tyr Asp Ala Leu His Met Gln Ala Leu Pro Pro Arg
        660                 665                 670

<210> SEQ ID NO 32
<211> LENGTH: 671
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 32

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
            20                  25                  30

Val Lys Pro Gly Ala Ser Val Lys Met Ser Cys Lys Ala Ser Gly Tyr
        35                  40                  45

Thr Phe Thr Ser Tyr Asn Met His Trp Val Lys Gln Thr Pro Gly Gln
    50                  55                  60

Gly Leu Glu Trp Ile Gly Ala Ile Tyr Pro Gly Asn Gly Asp Thr Ser
65                  70                  75                  80

Tyr Asn Gln Lys Phe Lys Gly Lys Ala Thr Leu Thr Ala Asp Lys Ser
                85                  90                  95

Ser Ser Thr Ala Tyr Met Gln Leu Ser Ser Leu Thr Ser Glu Asp Ser
                100                 105                 110

Ala Asp Tyr Tyr Cys Ala Arg Ser Asn Tyr Tyr Gly Ser Ser Tyr Trp
            115                 120                 125

Phe Phe Asp Val Trp Gly Ala Gly Thr Thr Val Thr Val Ser Ser Gly
    130                 135                 140

Gly Gly Gly Ser Gly Gly Gly Ser Gly Gly Gly Ser Asp Ile
145                 150                 155                 160

Val Leu Thr Gln Ser Pro Ala Ile Leu Ser Ala Ser Pro Gly Glu Lys
            165                 170                 175

Val Thr Met Thr Cys Arg Ala Ser Ser Ser Val Asn Tyr Met Asp Trp
            180                 185                 190

Tyr Gln Lys Lys Pro Gly Ser Ser Pro Lys Pro Trp Ile Tyr Ala Thr
        195                 200                 205

Ser Asn Leu Ala Ser Gly Val Pro Ala Arg Phe Ser Gly Ser Gly Ser
    210                 215                 220

Gly Thr Ser Tyr Ser Leu Thr Ile Ser Arg Val Glu Ala Glu Asp Ala
225                 230                 235                 240

Ala Thr Tyr Tyr Cys Gln Gln Trp Ser Phe Asn Pro Pro Thr Phe Gly
                245                 250                 255

Gly Gly Thr Lys Leu Glu Ile Lys Glu Ser Lys Tyr Gly Pro Pro Cys
            260                 265                 270

Pro Pro Cys Pro Ala Pro Glu Phe Leu Gly Gly Pro Ser Val Phe Leu
    275                 280                 285

Phe Pro Pro Lys Pro Lys Asp Thr Leu Met Ile Ser Arg Thr Pro Glu
    290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Gly Leu Pro Ser Ser Ile Glu Lys Thr Ile Ser Lys
        370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
                405                 410                 415
```

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Arg Leu Thr Val Asp Lys Ser Arg Trp Gln
450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys Ile Tyr Ile
                485                 490                 495

Trp Ala Pro Leu Ala Gly Thr Cys Gly Val Leu Leu Leu Ser Leu Val
            500                 505                 510

Ile Thr Leu Tyr Cys Lys Arg Gly Arg Lys Lys Leu Leu Tyr Ile Phe
        515                 520                 525

Lys Gln Pro Phe Met Arg Pro Val Gln Thr Thr Gln Glu Glu Asp Gly
530                 535                 540

Cys Ser Cys Arg Phe Pro Glu Glu Glu Glu Gly Gly Cys Glu Leu Arg
545                 550                 555                 560

Val Lys Phe Ser Arg Ser Ala Asp Ala Pro Ala Tyr Lys Gln Gly Gln
                565                 570                 575

Asn Gln Leu Tyr Asn Glu Leu Asn Leu Gly Arg Arg Glu Glu Tyr Asp
            580                 585                 590

Val Leu Asp Lys Arg Arg Gly Arg Asp Pro Glu Met Gly Gly Lys Pro
        595                 600                 605

Arg Arg Lys Asn Pro Gln Glu Gly Leu Tyr Asn Glu Leu Gln Lys Asp
610                 615                 620

Lys Met Ala Glu Ala Tyr Ser Glu Ile Gly Met Lys Gly Glu Arg Arg
625                 630                 635                 640

Arg Gly Lys Gly His Asp Gly Leu Tyr Gln Gly Leu Ser Thr Ala Thr
                645                 650                 655

Lys Asp Thr Tyr Asp Ala Leu His Met Gln Ala Leu Pro Pro Arg
            660                 665                 670

<210> SEQ ID NO 33
<211> LENGTH: 677
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 33

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Tyr
        35                  40                  45

Ala Phe Ser Tyr Ser Trp Ile Asn Trp Val Arg Gln Ala Pro Gly Gln
    50                  55                  60

Gly Leu Glu Trp Met Gly Arg Ile Phe Pro Gly Asp Gly Asp Thr Asp
65                  70                  75                  80

Tyr Asn Gly Lys Phe Lys Gly Arg Val Thr Ile Thr Ala Asp Lys Ser
                85                  90                  95

```
Thr Ser Thr Ala Tyr Met Glu Leu Ser Ser Leu Arg Ser Glu Asp Thr
            100                 105                 110
Ala Val Tyr Tyr Cys Ala Arg Asn Val Phe Asp Gly Tyr Trp Leu Val
        115                 120                 125
Tyr Trp Gly Gln Gly Thr Leu Val Thr Val Ser Ser Gly Gly Gly Gly
    130                 135                 140
Ser Gly Gly Gly Gly Ser Gly Gly Gly Gly Ser Asp Ile Val Met Thr
145                 150                 155                 160
Gln Thr Pro Leu Ser Leu Pro Val Thr Pro Gly Glu Pro Ala Ser Ile
                165                 170                 175
Ser Cys Arg Ser Ser Lys Ser Leu Leu His Ser Asn Gly Ile Thr Tyr
            180                 185                 190
Leu Tyr Trp Tyr Leu Gln Lys Pro Gly Gln Ser Pro Gln Leu Leu Ile
        195                 200                 205
Tyr Gln Met Ser Asn Leu Val Ser Gly Val Pro Asp Arg Phe Ser Gly
    210                 215                 220
Ser Gly Ser Gly Thr Asp Phe Thr Leu Lys Ile Ser Arg Val Glu Ala
225                 230                 235                 240
Glu Asp Val Gly Val Tyr Tyr Cys Ala Gln Asn Leu Glu Leu Pro Tyr
                245                 250                 255
Thr Phe Gly Gly Gly Thr Lys Val Glu Ile Lys Arg Thr Val Glu Ser
            260                 265                 270
Lys Tyr Gly Pro Pro Cys Pro Pro Cys Pro Ala Pro Glu Phe Leu Gly
        275                 280                 285
Gly Pro Ser Val Phe Leu Phe Pro Pro Lys Pro Lys Asp Thr Leu Met
    290                 295                 300
Ile Ser Arg Thr Pro Glu Val Thr Cys Val Val Val Asp Val Ser Gln
305                 310                 315                 320
Glu Asp Pro Glu Val Gln Phe Asn Trp Tyr Val Asp Gly Val Glu Val
                325                 330                 335
His Asn Ala Lys Thr Lys Pro Arg Glu Glu Gln Phe Asn Ser Thr Tyr
            340                 345                 350
Arg Val Val Ser Val Leu Thr Val Leu His Gln Asp Trp Leu Asn Gly
        355                 360                 365
Lys Glu Tyr Lys Cys Lys Val Ser Asn Lys Gly Leu Pro Ser Ser Ile
    370                 375                 380
Glu Lys Thr Ile Ser Lys Ala Lys Gly Gln Pro Arg Glu Pro Gln Val
385                 390                 395                 400
Tyr Thr Leu Pro Pro Ser Gln Glu Glu Met Thr Lys Asn Gln Val Ser
                405                 410                 415
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
        435                 440                 445
Val Leu Asp Ser Asp Gly Ser Phe Phe Leu Tyr Ser Arg Leu Thr Val
    450                 455                 460
Asp Lys Ser Arg Trp Gln Glu Gly Asn Val Phe Ser Cys Ser Val Met
465                 470                 475                 480
His Glu Ala Leu His Asn His Tyr Thr Gln Lys Ser Leu Ser Leu Ser
                485                 490                 495
Leu Gly Lys Ile Tyr Ile Trp Ala Pro Leu Ala Gly Thr Cys Gly Val
            500                 505                 510
Leu Leu Leu Ser Leu Val Ile Thr Leu Tyr Cys Lys Arg Gly Arg Lys
```

```
              515                 520                 525
Lys Leu Leu Tyr Ile Phe Lys Gln Pro Phe Met Arg Pro Val Gln Thr
        530                 535                 540

Thr Gln Glu Glu Asp Gly Cys Ser Cys Arg Phe Pro Glu Glu Glu Glu
545                 550                 555                 560

Gly Gly Cys Glu Leu Arg Val Lys Phe Ser Arg Ser Ala Asp Ala Pro
                565                 570                 575

Ala Tyr Lys Gln Gly Gln Asn Gln Leu Tyr Asn Glu Leu Asn Leu Gly
            580                 585                 590

Arg Arg Glu Glu Tyr Asp Val Leu Asp Lys Arg Arg Gly Arg Asp Pro
        595                 600                 605

Glu Met Gly Gly Lys Pro Arg Arg Lys Asn Pro Gln Glu Gly Leu Tyr
    610                 615                 620

Asn Glu Leu Gln Lys Asp Lys Met Ala Glu Ala Tyr Ser Glu Ile Gly
625                 630                 635                 640

Met Lys Gly Glu Arg Arg Arg Gly Lys Gly His Asp Gly Leu Tyr Gln
                645                 650                 655

Gly Leu Ser Thr Ala Thr Lys Asp Thr Tyr Asp Ala Leu His Met Gln
            660                 665                 670

Ala Leu Pro Pro Arg
            675

<210> SEQ ID NO 34
<211> LENGTH: 672
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 34

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asn Asp Tyr Ala Met His Trp Val Arg Gln Ala Pro Gly Lys
    50                  55                  60

Gly Leu Glu Trp Val Ser Thr Ile Ser Trp Asn Ser Gly Ser Ile Gly
65                  70                  75                  80

Tyr Ala Asp Ser Val Lys Gly Arg Phe Thr Ile Ser Arg Asp Asn Ala
                85                  90                  95

Lys Lys Ser Leu Tyr Leu Gln Met Asn Ser Leu Arg Ala Glu Asp Thr
            100                 105                 110

Ala Leu Tyr Tyr Cys Ala Lys Asp Ile Gln Tyr Gly Asn Tyr Tyr Tyr
        115                 120                 125

Gly Met Asp Val Trp Gly Gln Gly Thr Thr Val Thr Val Ser Ser Gly
    130                 135                 140

Gly Gly Gly Ser Gly Gly Gly Gly Ser Gly Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Ser Tyr Leu Ala
```

```
                    180                 185                 190
Trp Tyr Gln Gln Lys Pro Gly Gln Ala Pro Arg Leu Leu Ile Tyr Asp
            195                 200                 205

Ala Ser Asn Arg Ala Thr Gly Ile Pro Ala Arg Phe Ser Gly Ser Gly
        210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Ser Asn Trp Pro Ile Thr Phe
                245                 250                 255

Gly Gln Gly Thr Arg Leu Glu Ile Lys Glu Ser Lys Tyr Gly Pro Pro
            260                 265                 270

Cys Pro Pro Cys Pro Ala Pro Glu Phe Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser Gln Glu Asp Pro Glu Val
305                 310                 315                 320

Gln Phe Asn Trp Tyr Val Asp Gly Val Glu Val His Asn Ala Lys Thr
                325                 330                 335

Lys Pro Arg Glu Glu Gln Phe Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Gly Leu Pro Ser Ser Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Gln Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Arg Leu Thr Val Asp Lys Ser Arg Trp
    450                 455                 460

Gln Glu Gly Asn Val Phe Ser Cys Ser Val Met His Glu Ala Leu His
465                 470                 475                 480

Asn His Tyr Thr Gln Lys Ser Leu Ser Leu Ser Leu Gly Lys Ile Tyr
                485                 490                 495

Ile Trp Ala Pro Leu Ala Gly Thr Cys Gly Val Leu Leu Leu Ser Leu
            500                 505                 510

Val Ile Thr Leu Tyr Cys Lys Arg Gly Arg Lys Lys Leu Leu Tyr Ile
        515                 520                 525

Phe Lys Gln Pro Phe Met Arg Pro Val Gln Thr Thr Gln Glu Glu Asp
    530                 535                 540

Gly Cys Ser Cys Arg Phe Pro Glu Glu Glu Glu Gly Gly Cys Glu Leu
545                 550                 555                 560

Arg Val Lys Phe Ser Arg Ser Ala Asp Ala Pro Ala Tyr Lys Gln Gly
                565                 570                 575

Gln Asn Gln Leu Tyr Asn Glu Leu Asn Leu Gly Arg Arg Glu Glu Tyr
            580                 585                 590

Asp Val Leu Asp Lys Arg Arg Gly Arg Asp Pro Glu Met Gly Gly Lys
        595                 600                 605
```

```
Pro Arg Arg Lys Asn Pro Gln Glu Gly Leu Tyr Asn Glu Leu Gln Lys
        610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
        660                 665                 670

<210> SEQ ID NO 35
<211> LENGTH: 653
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 35

Met Ala Leu Pro Val Thr Ala Leu Leu Leu Pro Leu Ala Leu Leu Leu
1                 5                   10                  15

His Ala Ala Arg Pro Gly Asp Val Met Gly Val Asp Ser Gly Gly Gly
                20                  25                  30

Leu Val Gln Pro Gly Gly Ser Arg Lys Leu Ser Cys Ala Ala Pro Gly
            35                  40                  45

Phe Thr Phe Ser Ser Phe Gly Met His Trp Val Arg Gln Ala Pro Glu
        50                  55                  60

Lys Gly Leu Glu Trp Val Ala Tyr Ile Ser Ser Pro Ser Ser Thr Leu
65                  70                  75                  80

His Tyr Ala Asp Arg Val Lys Gly Arg Phe Thr Ile Ser Arg Asp Asn
                85                  90                  95

Pro Lys Asn Thr Leu Phe Leu Gln Met Lys Leu Pro Ser Leu Cys Tyr
            100                 105                 110

Gly Leu Leu Gly Pro Arg Asp His Val His Arg Leu Leu Lys Gly Gly
        115                 120                 125

Gly Gly Ser Gly Gly Gly Ser Gly Gly Gly Gly Ser Asp Ile Gln
        130                 135                 140

Leu Thr Gln Ser Pro Ala Ile Leu Ser Ala Ser Pro Gly Glu Lys Val
145                 150                 155                 160

Thr Met Thr Cys Arg Ala Ser Ser Ser Leu Ser Phe Met His Trp Tyr
                165                 170                 175

Gln Gln Lys Pro Gly Ser Ser Pro Lys Pro Trp Ile Tyr Ala Thr Ser
            180                 185                 190

Asn Leu Ala Ser Gly Val Pro Ala Arg Phe Ser Gly Ser Gly Ser Gly
        195                 200                 205

Thr Ser Tyr Ser Leu Thr Ile Ser Thr Val Glu Ala Glu Asp Ala Ala
        210                 215                 220

Ser Tyr Phe Cys His Gln Trp Ser Ser Asn Pro Leu Thr Phe Gly Ala
225                 230                 235                 240

Gly Thr Lys Leu Glu Ile Glu Ser Lys Tyr Gly Pro Pro Cys Pro Pro
                245                 250                 255

Cys Pro Ala Pro Glu Phe Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285
```

Cys Val Val Asp Val Ser Gln Glu Asp Pro Glu Val Gln Phe Asn
            290                 295                 300

Trp Tyr Val Asp Gly Val Glu Val His Asn Ala Lys Thr Lys Pro Arg
305                 310                 315                 320

Glu Glu Gln Phe Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Gly Leu Pro Ser Ser Ile Glu Lys Thr Ile Ser Lys Ala Lys
            355                 360                 365

Gly Gln Pro Arg Glu Pro Gln Val Tyr Thr Leu Pro Pro Ser Gln Glu
370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Arg Leu Thr Val Asp Lys Ser Arg Trp Gln Glu Gly
            435                 440                 445

Asn Val Phe Ser Cys Ser Val Met His Glu Ala Leu His Asn His Tyr
450                 455                 460

Thr Gln Lys Ser Leu Ser Leu Ser Leu Gly Lys Ile Tyr Ile Trp Ala
465                 470                 475                 480

Pro Leu Ala Gly Thr Cys Gly Val Leu Leu Leu Ser Leu Val Ile Thr
                485                 490                 495

Leu Tyr Cys Lys Arg Gly Arg Lys Lys Leu Leu Tyr Ile Phe Lys Gln
            500                 505                 510

Pro Phe Met Arg Pro Val Gln Thr Thr Gln Glu Glu Asp Gly Cys Ser
            515                 520                 525

Cys Arg Phe Pro Glu Glu Glu Gly Gly Cys Glu Leu Arg Val Lys
530                 535                 540

Phe Ser Arg Ser Ala Asp Ala Pro Ala Tyr Lys Gln Gly Gln Asn Gln
545                 550                 555                 560

Leu Tyr Asn Glu Leu Asn Leu Gly Arg Arg Glu Glu Tyr Asp Val Leu
                565                 570                 575

Asp Lys Arg Arg Gly Arg Asp Pro Glu Met Gly Gly Lys Pro Arg Arg
            580                 585                 590

Lys Asn Pro Gln Glu Gly Leu Tyr Asn Glu Leu Gln Lys Asp Lys Met
            595                 600                 605

Ala Glu Ala Tyr Ser Glu Ile Gly Met Lys Gly Glu Arg Arg Arg Gly
610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650

<210> SEQ ID NO 36
<211> LENGTH: 670
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 36

```
Met Ala Leu Pro Val Thr Ala Leu Leu Leu Pro Leu Ala Leu Leu Leu
1               5                   10                  15
His Ala Ala Arg Pro Gln Val Gln Leu Gln Gln Pro Gly Ala Glu Leu
            20                  25                  30
Val Lys Pro Gly Ala Ser Val Lys Met Ser Cys Lys Ala Ser Gly Tyr
        35                  40                  45
Thr Phe Thr Ser Tyr Asn Met His Trp Val Lys Gln Thr Pro Gly Arg
    50                  55                  60
Gly Leu Glu Trp Ile Gly Ala Ile Tyr Pro Gly Asn Gly Asp Thr Ser
65                  70                  75                  80
Tyr Asn Gln Lys Phe Lys Gly Lys Ala Thr Leu Thr Ala Asp Lys Ser
                85                  90                  95
Ser Ser Thr Ala Tyr Met Gln Leu Ser Ser Leu Thr Ser Glu Asp Ser
            100                 105                 110
Ala Val Tyr Tyr Cys Ala Arg Ser Thr Tyr Tyr Gly Gly Asp Trp Tyr
        115                 120                 125
Phe Asn Val Trp Gly Ala Gly Thr Thr Val Thr Val Ser Ala Gly Gly
    130                 135                 140
Gly Gly Ser Gly Gly Gly Gly Ser Gly Gly Gly Gly Ser Gln Ile Val
145                 150                 155                 160
Leu Ser Gln Ser Pro Ala Ile Leu Ser Ala Ser Pro Gly Glu Lys Val
                165                 170                 175
Thr Met Thr Cys Arg Ala Ser Ser Ser Val Ser Tyr Ile His Trp Phe
            180                 185                 190
Gln Gln Lys Pro Gly Ser Ser Pro Lys Pro Trp Ile Tyr Ala Thr Ser
        195                 200                 205
Asn Leu Ala Ser Gly Val Pro Val Arg Phe Ser Gly Ser Gly Ser Gly
    210                 215                 220
Thr Ser Tyr Ser Leu Thr Ile Ser Arg Val Glu Ala Glu Asp Ala Ala
225                 230                 235                 240
Thr Tyr Tyr Cys Gln Gln Trp Thr Ser Asn Pro Pro Thr Phe Gly Gly
                245                 250                 255
Gly Thr Lys Leu Glu Ile Lys Glu Ser Lys Tyr Gly Pro Pro Cys Pro
            260                 265                 270
Pro Cys Pro Ala Pro Glu Phe Leu Gly Gly Pro Ser Val Phe Leu Phe
        275                 280                 285
Pro Pro Lys Pro Lys Asp Thr Leu Met Ile Ser Arg Thr Pro Glu Val
    290                 295                 300
Thr Cys Val Val Val Asp Val Ser Gln Glu Asp Pro Glu Val Gln Phe
305                 310                 315                 320
Asn Trp Tyr Val Asp Gly Val Glu Val His Asn Ala Lys Thr Lys Pro
                325                 330                 335
Arg Glu Glu Gln Phe Asn Ser Thr Tyr Arg Val Val Ser Val Leu Thr
            340                 345                 350
Val Leu His Gln Asp Trp Leu Asn Gly Lys Glu Tyr Lys Cys Lys Val
        355                 360                 365
Ser Asn Lys Gly Leu Pro Ser Ser Ile Glu Lys Thr Ile Ser Lys Ala
    370                 375                 380
Lys Gly Gln Pro Arg Glu Pro Gln Val Tyr Thr Leu Pro Pro Ser Gln
385                 390                 395                 400
```

```
Glu Glu Met Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Arg Leu Thr Val Asp Lys Ser Arg Trp Gln Glu
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Leu Gly Lys Ile Tyr Ile Trp
                485                 490                 495

Ala Pro Leu Ala Gly Thr Cys Gly Val Leu Leu Leu Ser Leu Val Ile
            500                 505                 510

Thr Leu Tyr Cys Lys Arg Gly Arg Lys Lys Leu Leu Tyr Ile Phe Lys
        515                 520                 525

Gln Pro Phe Met Arg Pro Val Gln Thr Thr Gln Glu Glu Asp Gly Cys
    530                 535                 540

Ser Cys Arg Phe Pro Glu Glu Glu Glu Gly Gly Cys Glu Leu Arg Val
545                 550                 555                 560

Lys Phe Ser Arg Ser Ala Asp Ala Pro Ala Tyr Lys Gln Gly Gln Asn
                565                 570                 575

Gln Leu Tyr Asn Glu Leu Asn Leu Gly Arg Arg Glu Glu Tyr Asp Val
            580                 585                 590

Leu Asp Lys Arg Arg Gly Arg Asp Pro Glu Met Gly Gly Lys Pro Arg
        595                 600                 605

Arg Lys Asn Pro Gln Glu Gly Leu Tyr Asn Glu Leu Gln Lys Asp Lys
    610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
            660                 665                 670

<210> SEQ ID NO 37
<211> LENGTH: 715
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 37

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
                20                  25                  30

Val Lys Pro Gly Ala Ser Val Lys Met Ser Cys Lys Ala Ser Gly Tyr
            35                  40                  45

Thr Phe Thr Ser Tyr Asn Met His Trp Val Lys Gln Thr Pro Gly Gln
        50                  55                  60

Gly Leu Glu Trp Ile Gly Ala Ile Tyr Pro Gly Asn Gly Asp Thr Ser
65                  70                  75                  80
```

```
Tyr Asn Gln Lys Phe Lys Gly Lys Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Asp Tyr Tyr Cys Ala Arg Ser Asn Tyr Tyr Gly Ser Ser Tyr Trp
        115                 120                 125

Phe Phe Asp Val Trp Gly Ala Gly Thr Thr Val Thr Val Ser Ser Gly
    130                 135                 140

Gly Gly Gly Ser Gly Gly Gly Ser Gly Gly Gly Ser Gly Asp Ile
145                 150                 155                 160

Val Leu Thr Gln Ser Pro Ala Ile Leu Ser Ala Ser Pro Gly Glu Lys
                165                 170                 175

Val Thr Met Thr Cys Arg Ala Ser Ser Ser Val Asn Tyr Met Asp Trp
            180                 185                 190

Tyr Gln Lys Lys Pro Gly Ser Ser Pro Lys Pro Trp Ile Tyr Ala Thr
        195                 200                 205

Ser Asn Leu Ala Ser Gly Val Pro Ala Arg Phe Ser Gly Ser Gly Ser
    210                 215                 220

Gly Thr Ser Tyr Ser Leu Thr Ile Ser Arg Val Glu Ala Glu Asp Ala
225                 230                 235                 240

Ala Thr Tyr Tyr Cys Gln Gln Trp Ser Phe Asn Pro Pro Thr Phe Gly
                245                 250                 255

Gly Gly Thr Lys Leu Glu Ile Lys Glu Ser Lys Tyr Gly Pro Pro Cys
            260                 265                 270

Pro Pro Cys Pro Ala Pro Glu Phe Glu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Gln Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Gly Leu Pro Ser Ser Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Arg Leu Thr Val Asp Lys Ser Arg Trp Gln
    450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys Phe Trp Val
                485                 490                 495

Leu Val Val Val Gly Gly Val Leu Ala Cys Tyr Ser Leu Leu Val Thr
```

```
                      500                 505                 510
Val Ala Phe Ile Ile Phe Trp Val Arg Ser Lys Arg Ser Arg Leu Leu
                  515                 520                 525

His Ser Asp Tyr Met Asn Met Thr Pro Arg Arg Pro Gly Pro Thr Arg
              530                 535                 540

Lys His Tyr Gln Pro Tyr Ala Pro Pro Arg Asp Phe Ala Ala Tyr Arg
545                 550                 555                 560

Ser Lys Arg Gly Arg Lys Lys Leu Leu Tyr Ile Phe Lys Gln Pro Phe
                  565                 570                 575

Met Arg Pro Val Gln Thr Thr Gln Glu Glu Asp Gly Cys Ser Cys Arg
              580                 585                 590

Phe Pro Glu Glu Glu Glu Gly Gly Cys Glu Leu Arg Val Lys Phe Ser
              595                 600                 605

Arg Ser Ala Asp Ala Pro Ala Tyr Lys Gln Gly Gln Asn Gln Leu Tyr
              610                 615                 620

Asn Glu Leu Asn Leu Gly Arg Arg Glu Glu Tyr Asp Val Leu Asp Lys
625                 630                 635                 640

Arg Arg Gly Arg Asp Pro Glu Met Gly Gly Lys Pro Arg Arg Lys Asn
                  645                 650                 655

Pro Gln Glu Gly Leu Tyr Asn Glu Leu Gln Lys Asp Lys Met Ala Glu
              660                 665                 670

Ala Tyr Ser Glu Ile Gly Met Lys Gly Glu Arg Arg Arg Gly Lys Gly
              675                 680                 685

His Asp Gly Leu Tyr Gln Gly Leu Ser Thr Ala Thr Lys Asp Thr Tyr
              690                 695                 700

Asp Ala Leu His Met Gln Ala Leu Pro Pro Arg
705                 710                 715

<210> SEQ ID NO 38
<211> LENGTH: 660
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 38

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
              20                  25                  30

Val Lys Pro Gly Ala Ser Val Lys Met Ser Cys Lys Ala Ser Gly Tyr
          35                  40                  45

Thr Phe Thr Ser Tyr Asn Met His Trp Val Lys Gln Thr Pro Gly Gln
     50                  55                  60

Gly Leu Glu Trp Ile Gly Ala Ile Tyr Pro Gly Asn Gly Asp Thr Ser
65                  70                  75                  80

Tyr Asn Gln Lys Phe Lys Gly Lys Ala Thr Leu Thr Ala Asp Lys Ser
                  85                  90                  95

Ser Ser Thr Ala Tyr Met Gln Leu Ser Ser Leu Thr Ser Glu Asp Ser
              100                 105                 110

Ala Asp Tyr Tyr Cys Ala Arg Ser Asn Tyr Tyr Gly Ser Ser Tyr Trp
          115                 120                 125

Phe Phe Asp Val Trp Gly Ala Gly Thr Thr Val Thr Val Ser Ser Gly
```

```
            130                 135                 140
Gly Gly Gly Ser Gly Gly Gly Ser Gly Gly Gly Ser Asp Ile
145                 150                 155                 160

Val Leu Thr Gln Ser Pro Ala Ile Leu Ser Ala Ser Pro Gly Glu Lys
                    165                 170                 175

Val Thr Met Thr Cys Arg Ala Ser Ser Ser Val Asn Tyr Met Asp Trp
                180                 185                 190

Tyr Gln Lys Lys Pro Gly Ser Ser Pro Lys Pro Trp Ile Tyr Ala Thr
            195                 200                 205

Ser Asn Leu Ala Ser Gly Val Pro Ala Arg Phe Ser Gly Ser Gly Ser
        210                 215                 220

Gly Thr Ser Tyr Ser Leu Thr Ile Ser Arg Val Glu Ala Glu Asp Ala
225                 230                 235                 240

Ala Thr Tyr Tyr Cys Gln Gln Trp Ser Phe Asn Pro Pro Thr Phe Gly
                245                 250                 255

Gly Gly Thr Lys Leu Glu Ile Lys Glu Ser Lys Tyr Gly Pro Pro Cys
            260                 265                 270

Pro Pro Cys Pro Ala Pro Glu Phe Glu Gly Gly Pro Ser Val Phe Leu
        275                 280                 285

Phe Pro Pro Lys Pro Lys Asp Thr Leu Met Ile Ser Arg Thr Pro Glu
290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Gln Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Gly Leu Pro Ser Ser Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Arg Leu Thr Val Asp Lys Ser Arg Trp Gln
    450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys Ile Tyr Ile
                485                 490                 495

Trp Ala Pro Leu Ala Gly Thr Cys Gly Val Leu Leu Leu Ser Leu Val
            500                 505                 510

Ile Thr Leu Tyr Cys Lys Arg Gly Arg Lys Lys Leu Leu Tyr Ile Phe
        515                 520                 525

Lys Gln Pro Phe Met Arg Pro Val Gln Thr Thr Gln Glu Glu Asp Gly
    530                 535                 540

Cys Ser Cys Arg Phe Pro Glu Glu Glu Glu Gly Gly Cys Glu Leu Arg
545                 550                 555                 560
```

-continued

Val Lys Phe Ser Arg Ser Ala Asp Ala Pro Ala Tyr Lys Gln Gly Gln
            565                 570                 575

Asn Gln Leu Tyr Asn Glu Leu Asn Leu Gly Arg Arg Glu Glu Tyr Asp
            580                 585                 590

Val Leu Asp Lys Arg Arg Gly Arg Asp Pro Glu Met Gly Gly Lys Pro
595                 600                 605

Arg Arg Lys Asn Pro Gln Glu Gly Leu Tyr Asn Glu Leu Gln Lys Asp
        610                 615                 620

Lys Met Ala Glu Ala Tyr Ser Glu Ile Gly Met Lys Gly Glu Arg Arg
625                 630                 635                 640

Arg Gly Lys Gly His Asp Gly Leu Tyr Gln Gly Leu Ser Thr Ala Thr
            645                 650                 655

Lys Asp Thr Tyr
            660

<210> SEQ ID NO 39
<211> LENGTH: 672
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: Chimeric antigen receptor

<400> SEQUENCE: 39

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Ser Cys Ala Ala Ser Gly Phe
        35                  40                  45

Thr Phe Asn Asp Tyr Ala Met His Trp Val Arg Gln Ala Pro Gly Lys
    50                  55                  60

Gly Leu Glu Trp Val Ser Thr Ile Ser Trp Asn Ser Gly Ser Ile Gly
65                  70                  75                  80

Tyr Ala Asp Ser Val Lys Gly Arg Phe Thr Ile Ser Arg Asp Asn Ala
                85                  90                  95

Lys Lys Ser Leu Tyr Leu Gln Met Asn Ser Leu Arg Ala Glu Asp Thr
            100                 105                 110

Ala Leu Tyr Tyr Cys Ala Lys Asp Ile Gln Tyr Gly Asn Tyr Tyr Tyr
        115                 120                 125

Gly Met Asp Val Trp Gly Gln Gly Thr Thr Val Thr Val Ser Ser Gly
    130                 135                 140

Gly Gly Gly Ser Gly Gly Gly Gly Ser Gly Gly Gly Gly Ser Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Ser Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Ser Asn Trp Pro Ile Thr Phe
                245                 250                 255

Gly Gln Gly Thr Arg Leu Glu Ile Lys Glu Ser Lys Tyr Gly Pro Pro
            260                 265                 270

Cys Pro Pro Cys Pro Ala Pro Glu Phe Glu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser Gln Glu Asp Pro Glu Val
305                 310                 315                 320

Gln Phe Asn Trp Tyr Val Asp Gly Val Glu Val His Asn Ala Lys Thr
                325                 330                 335

Lys Pro Arg Glu Glu Gln Phe Gln Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Gly Leu Pro Ser Ser Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Gln Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Arg Leu Thr Val Asp Lys Ser Arg Trp
    450                 455                 460

Gln Glu Gly Asn Val Phe Ser Cys Ser Val Met His Glu Ala Leu His
465                 470                 475                 480

Asn His Tyr Thr Gln Lys Ser Leu Ser Leu Ser Leu Gly Lys Ile Tyr
                485                 490                 495

Ile Trp Ala Pro Leu Ala Gly Thr Cys Gly Val Leu Leu Leu Ser Leu
            500                 505                 510

Val Ile Thr Leu Tyr Cys Lys Arg Gly Arg Lys Lys Leu Leu Tyr Ile
        515                 520                 525

Phe Lys Gln Pro Phe Met Arg Pro Val Gln Thr Thr Gln Glu Glu Asp
    530                 535                 540

Gly Cys Ser Cys Arg Phe Pro Glu Glu Glu Glu Gly Gly Cys Glu Leu
545                 550                 555                 560

Arg Val Lys Phe Ser Arg Ser Ala Asp Ala Pro Ala Tyr Lys Gln Gly
                565                 570                 575

Gln Asn Gln Leu Tyr Asn Glu Leu Asn Leu Gly Arg Arg Glu Glu Tyr
            580                 585                 590

Asp Val Leu Asp Lys Arg Arg Gly Arg Asp Pro Glu Met Gly Gly Lys
        595                 600                 605

Pro Arg Arg Lys Asn Pro Gln Glu Gly Leu Tyr Asn Glu Leu Gln Lys
    610                 615                 620

Asp Lys Met Ala Glu Ala Tyr Ser Glu Ile Gly Met Lys Gly Glu Arg
625                 630                 635                 640

-continued

```
Arg Arg Gly Lys Gly His Asp Gly Leu Tyr Gln Gly Leu Ser Thr Ala
            645                 650                 655

Thr Lys Asp Thr Tyr Asp Ala Leu His Met Gln Ala Leu Pro Pro Arg
            660                 665                 670
```